US008563527B2

(12) United States Patent
Castillo et al.

(10) Patent No.: US 8,563,527 B2
(45) Date of Patent: Oct. 22, 2013

(54) OLIGONUCLEOTIDE CORE CARRIER COMPOSITIONS FOR DELIVERY OF NUCLEIC ACID-CONTAINING THERAPEUTIC AGENTS, METHODS OF MAKING AND USING THE SAME

(75) Inventors: Gerardo M. Castillo, Bothell, WA (US); Elijah M. Bolotin, Bothell, WA (US); Alexei A. Bogdanov, Jr., Westborough, MA (US)

(73) Assignee: Pharmain Corporation, Bothell, WA (US)

( * ) Notice: Subject to any disclaimer, the term of this patent is extended or adjusted under 35 U.S.C. 154(b) by 0 days.

(21) Appl. No.: 12/194,144

(22) Filed: Aug. 19, 2008

(65) Prior Publication Data

US 2009/0053169 A1    Feb. 26, 2009

Related U.S. Application Data

(60) Provisional application No. 60/956,916, filed on Aug. 20, 2007.

(51) Int. Cl.
*A61K 48/00* (2006.01)

(52) U.S. Cl.
USPC .......................... 514/44 R; 977/704; 977/705

(58) Field of Classification Search
None
See application file for complete search history.

(56) References Cited

U.S. PATENT DOCUMENTS

| | | |
|---|---|---|
| 3,998,795 A | 12/1976 | Sarantakis |
| 4,801,580 A | 1/1989 | Kitaura et al. |
| 4,857,311 A | 8/1989 | Domb et al. |
| 5,019,383 A | 5/1991 | Hopp |
| 5,118,666 A | 6/1992 | Habener |
| 5,120,712 A | 6/1992 | Habener |
| 5,527,524 A | 6/1996 | Tomalia et al. |
| 5,554,388 A | 9/1996 | Illum |
| 5,593,658 A | 1/1997 | Bogdanov et al. |
| 5,605,672 A | 2/1997 | Bogdanov et al. |
| 5,614,492 A | 3/1997 | Habener |
| 5,631,018 A | 5/1997 | Zalipsky et al. |
| 5,661,025 A | 8/1997 | Szoka, Jr. et al. |
| 5,663,387 A | 9/1997 | Singh |
| 5,681,544 A | 10/1997 | Schmitt-Willich et al. |
| 5,714,166 A | 2/1998 | Tomalia et al. |
| 5,744,166 A | 4/1998 | Illum |
| 5,753,611 A | 5/1998 | Franssen et al. |
| 5,763,585 A | 6/1998 | Nag |
| 5,837,747 A | 11/1998 | Soon-Shiong et al. |
| 5,871,710 A | 2/1999 | Bogdanov et al. |
| 5,891,418 A | 4/1999 | Sharma |
| 5,958,909 A | 9/1999 | Habener |
| 5,977,084 A | 11/1999 | Szoka, Jr. et al. |
| 5,990,273 A | 11/1999 | Andersson et al. |
| 6,006,753 A | 12/1999 | Efendic |
| 6,051,549 A | 4/2000 | Roberts et al. |
| 6,113,946 A | 9/2000 | Szoka, Jr. et al. |
| 6,124,273 A | 9/2000 | Drohan et al. |
| 6,162,462 A | 12/2000 | Bolotin et al. |
| 6,177,274 B1 | 1/2001 | Park et al. |
| 6,232,366 B1 | 5/2001 | Wang et al. |
| 6,274,175 B1 | 8/2001 | Gombotz et al. |
| 6,284,727 B1 | 9/2001 | Kim et al. |
| 6,338,859 B1 | 1/2002 | Leroux et al. |
| 6,348,069 B1 | 2/2002 | Vacanti et al. |
| 6,365,173 B1 | 4/2002 | Domb et al. |
| 6,395,299 B1 | 5/2002 | Babich et al. |
| 6,443,898 B1 | 9/2002 | Unger et al. |
| 6,447,753 B2 | 9/2002 | Edwards et al. |
| 6,458,373 B1 | 10/2002 | Lambert et al. |
| 6,468,532 B1 | 10/2002 | Hsei et al. |
| 6,475,779 B2 | 11/2002 | Mathiowitz et al. |
| 6,492,560 B2 | 12/2002 | Wilbur et al. |
| 6,509,323 B1 | 1/2003 | Davis et al. |
| 6,521,211 B1 | 2/2003 | Unger et al. |
| 6,521,736 B2 | 2/2003 | Watterson et al. |
| 6,576,254 B1 | 6/2003 | Uchegbu |
| 6,579,851 B2 | 6/2003 | Goeke et al. |
| 6,583,111 B1 | 6/2003 | DiMarchi et al. |
| 6,586,524 B2 | 7/2003 | Sagara et al. |
| 6,589,549 B2 | 7/2003 | Shih et al. |
| 6,627,228 B1 | 9/2003 | Milstein et al. |
| 6,703,037 B1 | 3/2004 | Hubbell et al. |
| 6,703,359 B1 | 3/2004 | Young et al. |
| 6,706,689 B2 | 3/2004 | Coolidge et al. |
| 6,747,006 B2 | 6/2004 | Efendic |

(Continued)

FOREIGN PATENT DOCUMENTS

| | | |
|---|---|---|
| EP | 0381446 B1 | 8/1994 |
| JP | 10158195 | 6/1998 |

(Continued)

OTHER PUBLICATIONS

Ahren, et al. Improved glucose tolerance and insulin secretion by inhibition of dipeptidyl peptidase IV in mice. Eur J Pharmacol. Sep. 15, 2000;404(1-2):239-45.

Aigner, A. Applications of RNA interference: current state and prospects for siRNA-based strategies in vivo. Appl Microbiol Biotechnol. Aug. 2007;76(1):9-21.

Baigude, et al. Design and creation of new nanomaterials for therapeutic RNAi. ACS Chem Biol. Apr. 24, 2007;2(4):237-41.

Bogdanov, et al. A new macromolecule as a contrast agent for MR angiography: preparation, properties, and animal studies. Radiology. Jun. 1993;187(3):701-6.

Bogdanov, et al. Long-circulating blood pool imaging agents. Advanced Drug Delivery Reviews. 1995; 335-348.

(Continued)

*Primary Examiner* — Doug Schultz
(74) *Attorney, Agent, or Firm* — Wilson Sonsini Goodrich & Rosati

(57) ABSTRACT

The present invention relates, in part, to an oligonucleotide-core carrier comprising a carrier, and oligonucleotide groups covalently linked to the carrier. The oligonucleotide groups are capable of dissociably linking load molecules such as therapeutic agents. The oligonucleotide-core carrier may also comprise protective side chains, and targeting molecules.

18 Claims, 20 Drawing Sheets

(56) References Cited

U.S. PATENT DOCUMENTS

| | | | |
|---|---|---|---|
| 6,828,303 B2 | 12/2004 | Kim et al. | |
| 6,849,708 B1 | 2/2005 | Habener | |
| 6,884,628 B2 | 4/2005 | Hubbell et al. | |
| 6,894,024 B2 | 5/2005 | Coolidge et al. | |
| 6,899,883 B2 | 5/2005 | Dupre | |
| 6,982,248 B2 | 1/2006 | Coolidge et al. | |
| 6,992,060 B2 | 1/2006 | Brand | |
| 6,998,137 B2 | 2/2006 | Shih et al. | |
| 7,049,284 B2 | 5/2006 | Drucker | |
| 7,101,843 B2 | 9/2006 | Glaesner et al. | |
| 7,138,105 B2 | 11/2006 | Bolotin | |
| 7,138,486 B2 | 11/2006 | Habener | |
| 7,144,863 B2 | 12/2006 | DeFelippis et al. | |
| 7,199,217 B2 | 4/2007 | DiMarchi et al. | |
| 7,259,233 B2 | 8/2007 | Dodd et al. | |
| 7,319,000 B1 | 1/2008 | Sastry et al. | |
| 7,534,449 B2 | 5/2009 | Saltzman et al. | |
| 2001/0006817 A1 | 7/2001 | Pack et al. | |
| 2002/0015737 A1 | 2/2002 | Shih et al. | |
| 2002/0132254 A1 | 9/2002 | Twu | |
| 2003/0050237 A1 | 3/2003 | Kim et al. | |
| 2003/0119734 A1 | 6/2003 | Flink et al. | |
| 2003/0138407 A1 | 7/2003 | Lu et al. | |
| 2003/0220251 A1 | 11/2003 | Knudsen et al. | |
| 2003/0224974 A1 | 12/2003 | Bolotin | |
| 2003/0229034 A1 | 12/2003 | Waugh et al. | |
| 2003/0232968 A1 | 12/2003 | Li et al. | |
| 2004/0018176 A1 | 1/2004 | Tolentino et al. | |
| 2004/0077840 A1 | 4/2004 | Granoff et al. | |
| 2004/0092432 A1 | 5/2004 | During et al. | |
| 2004/0106589 A1 | 6/2004 | Webb et al. | |
| 2004/0162241 A1 | 8/2004 | Efendic | |
| 2004/0197369 A1 | 10/2004 | Hubbell et al. | |
| 2004/0209803 A1 | 10/2004 | Baron et al. | |
| 2004/0220105 A1 | 11/2004 | Jensen et al. | |
| 2004/0235726 A1 | 11/2004 | Jakubowski et al. | |
| 2004/0266683 A1 | 12/2004 | Hathaway et al. | |
| 2005/0008661 A1 | 1/2005 | Fereira et al. | |
| 2005/0014681 A1 | 1/2005 | Minamitake et al. | |
| 2005/0037075 A1 | 2/2005 | Farokhzad et al. | |
| 2005/0143303 A1 | 6/2005 | Quay et al. | |
| 2005/0148497 A1 | 7/2005 | Khan et al. | |
| 2005/0153913 A1* | 7/2005 | Kosak | 514/44 |
| 2005/0159356 A1 | 7/2005 | Dong et al. | |
| 2005/0215475 A1 | 9/2005 | Ong et al. | |
| 2005/0239705 A1 | 10/2005 | Dake et al. | |
| 2005/0260259 A1 | 11/2005 | Bolotin | |
| 2006/0003935 A1 | 1/2006 | Pan et al. | |
| 2006/0014695 A1 | 1/2006 | Ghandehari et al. | |
| 2006/0019874 A1 | 1/2006 | Radhakrishnan et al. | |
| 2006/0030838 A1 | 2/2006 | Gonnelli | |
| 2006/0035815 A1* | 2/2006 | Chen et al. | 514/7 |
| 2006/0040879 A1* | 2/2006 | Kosak | 514/44 |
| 2006/0057137 A1 | 3/2006 | Steiness | |
| 2006/0074025 A1 | 4/2006 | Quay et al. | |
| 2006/0093660 A1 | 5/2006 | Bolotin | |
| 2006/0128627 A1 | 6/2006 | Goke et al. | |
| 2006/0172001 A1 | 8/2006 | Ong et al. | |
| 2006/0172003 A1 | 8/2006 | Meers et al. | |
| 2006/0178304 A1 | 8/2006 | Juul-Mortensen et al. | |
| 2006/0183682 A1 | 8/2006 | Juul-Mortensen | |
| 2006/0199763 A1 | 9/2006 | Knudsen et al. | |
| 2006/0233857 A1 | 10/2006 | Amsden et al. | |
| 2006/0239924 A1 | 10/2006 | Bolotin | |
| 2006/0247167 A1 | 11/2006 | Schlein et al. | |
| 2006/0286129 A1 | 12/2006 | Sarubbi | |
| 2007/0036806 A1 | 2/2007 | Glaesner et al. | |
| 2007/0041951 A1 | 2/2007 | Egan et al. | |
| 2007/0141006 A1 | 6/2007 | Livoreil et al. | |
| 2007/0141145 A1 | 6/2007 | Castillo et al. | |
| 2007/0219118 A1 | 9/2007 | Lu et al. | |
| 2007/0225213 A1* | 9/2007 | Kosak | 514/7 |
| 2007/0244296 A1 | 10/2007 | Tomalia et al. | |
| 2007/0298006 A1 | 12/2007 | Tomalia et al. | |
| 2008/0015263 A1 | 1/2008 | Bolotin et al. | |
| 2008/0026995 A1 | 1/2008 | Tosi et al. | |
| 2008/0159992 A1 | 7/2008 | Rotman et al. | |
| 2008/0312174 A1 | 12/2008 | Yu et al. | |
| 2009/0088387 A1 | 4/2009 | Castillo et al. | |
| 2009/0156459 A1 | 6/2009 | Castillo et al. | |
| 2010/0233084 A1* | 9/2010 | Narasimhaswamy et al. | 424/9.1 |
| 2010/0234279 A1 | 9/2010 | Castillo et al. | |
| 2011/0207662 A1 | 8/2011 | Castillo et al. | |

FOREIGN PATENT DOCUMENTS

| | | |
|---|---|---|
| WO | WO 94/05203 A1 | 3/1994 |
| WO | WO 97/33552 A1 | 9/1997 |
| WO | WO 98/42383 A1 | 10/1998 |
| WO | WO 01/28569 A1 | 4/2001 |
| WO | WO 01/39815 A2 | 6/2001 |
| WO | WO 01/39815 A3 | 1/2002 |
| WO | WO 02/24213 A2 | 3/2002 |
| WO | WO 02/24213 A3 | 6/2002 |
| WO | WO 03/070749 A2 | 8/2003 |
| WO | WO 03/072143 A1 | 9/2003 |
| WO | WO 2004/014451 A1 | 2/2004 |
| WO | WO 2004/022004 A2 | 3/2004 |
| WO | WO 03/070749 A3 | 4/2004 |
| WO | WO 2004/022004 A3 | 12/2004 |
| WO | WO 2005/076998 A2 | 8/2005 |
| WO | WO 2005/084180 A2 | 9/2005 |
| WO | WO 2005/084180 A3 | 12/2005 |
| WO | WO 2005/076998 A3 | 1/2006 |
| WO | WO 2006/062398 A2 | 6/2006 |
| WO | WO 2006/062398 A3 | 10/2006 |
| WO | WO 2007/024899 A2 | 3/2007 |
| WO | WO 2007/030706 A1 | 3/2007 |
| WO | WO 2007/048190 A1 | 5/2007 |
| WO | WO 2007/056681 A2 | 5/2007 |
| WO | WO 2007/082331 A1 | 7/2007 |
| WO | WO 2007/024899 A3 | 11/2007 |
| WO | WO 2007/056681 A3 | 4/2008 |

OTHER PUBLICATIONS

Bogdanov, Jr, et al. Merging molecular imaging and RNA interference: early experience in live animals. J Cell Biochem. Jul. 1, 2008;104(4):1113-23.

Bonner-Weir, et al. Imaging the Pancreatic Beta Cell. JDFI Workshop. Apr. 1999.

Brand, et al. Pharmacological treatment of chronic diabetes by stimulating pancreatic beta-cell regeneration with systemic co-administration of EGF and gastrin. Pharmacol Toxicol. Dec. 2002;91(6):414-20.

Bulotta, et al. Cultured pancreatic ductal cells undergo cell cycle re-distribution and beta-cell-like differentiation in response to glucagon-like peptide-1. J Mol Endocrinol. Dec. 2002;29(3):347-60.

Buteau, et al. Glucagon-like peptide-1 promotes DNA synthesis, activates phosphatidylinositol 3-kinase and increases transcription factor pancreatic and duodenal homeobox gene 1 (PDX-1) DNA binding activity in beta (INS-1)-cells. Diabetologia. Jul. 1999;42(7):856-64.

Cadranel, et al. Omeprazole efficacy and tolerance in 20 patients with longstanding Zollinger-Ellison syndrome. Gastroenterol Clin Biol. 1989; 13(8-9):654-62. (in French with English Summary).

Caliceti, et al. Pharmacokinetic and biodistribution properties of poly(ethylene glycol)-protein conjugates. Adv Drug Deliv Rev. Sep. 26, 2003;55(10):1261-77.

Callahan, et al. Preclinical evaluation and phase I clinical trial of a 99mTc-labeled synthetic polymer used in blood pool imaging. AJR Am J Roentgenol. Jul. 1998;171(1):137-43.

Chen, et al. A novel gene delivery system using EGF receptor-mediated endocytosis. FEBS Lett. Jan. 31, 1994;338(2):167-9.

Chowdhury, et al. Fate of DNA targeted to the liver by asialoglycoprotein receptor-mediated endocytosis in vivo. Prolonged persistence in cytoplasmic vesicles after partial hepatectomy. J Biol Chem. May 25, 1993;268(15):11265-71.

Clark, et al. Guide for the Care and Use of Laboratory Animals. Institute of Laboratory Animal Resources. National Academy Press. Washington, D.C. 1996.

(56) References Cited

OTHER PUBLICATIONS

Cras-Meneur, et al. Epidermal growth factor increases undifferentiated pancreatic embryonic cells in vitro: a balance between proliferation and differentiation. Diabetes 2001; 50(7):1571-1579.

Creutzfeldt, et al. Is Hypergastrinaemia dangerous to man? Scand J Gastroenterol Suppl. 1991; 180:179-191.

Cunningham, et al. Dimerization of human growth hormone by zinc. Science. Aug. 2, 1991;253(5019):545-8.

Dash, et al. Synthetic polymers for vectorial delivery of DNA: characterisation of polymer-DNA complexes by photon correlation spectroscopy and stability to nuclease degradation and disruption by polyanions in vitro. Journal of Controlled Release. 1997; 48: 269-276.

De Fougerolles, et al. Delivery vehicles for small interfering RNA in vivo. Hum Gene Ther. Feb. 2008;19(2):125-32.

Drucker, et al. Enhancing incretin action for the treatment of type 2 diabetes. Diabetes Care. Oct. 2003:26(10):2929-40.

Eckstein, F. Small non-coding RNAs as magic bullets. Trends Biochem Sci. Aug. 2005;30(8):445-52.

Erbacher, et al. The reduction of the positive charges of polylysine by partial gluconoylation increases the transfection efficiency of polylysine/DNA complexes. Biochim Biophys Acta. 1997; 1324(1):27-36.

O'Brien, et al. Terlipressin for norepinephrine-resistant septic shock. Lancet. 2002; 359(9313):1209-10. (abstract only).

Eto, et al. Regulation of insulin gene transcription by the immediate-early growth response gene Egr-1. Endocrinology. Jun. 2006;147(6):2923-35.

Ettaro, et al. Cost-of-illness studies in diabetes mellitus. Pharmacoeconomics. 2004;22(3):149-64.

Farilla, et al. Glucagon-like peptide 1 inhibits cell apoptosis and improves glucose responsiveness of freshly isolated human islets. Endocrinology. Dec. 2003;144(12):5149-58.

Feng, et al. Tissue distribution and plasma clearance of heparin-binding EGF-like growth factor (HB-EGF) in adult and newborn rats. Peptides. 2005.

Filipowicz, W. RNAi: the nuts and bolts of the RISC machine. Cell. Jul. 15, 2005;122(1):17-20.

Gappa, et al. The effect of zinc-crystallized glucagon-like peptide-1 on insulin secretion of macroencapsulated pancreatic islets. Tissue Eng. Feb. 2001;7(1):35-44.

Giammona, et al. Coupling of the antiviral agent zidovudine to polyaspartamide and in vitro drug release studies. J Control Release. Aug. 14, 1998;54(3):321-31.

Greene, et al. Protection for the amino group. In Protecive Groups in Organic Synthesis. Wiley, John, & Sons. 2nd ed. New York, 1991; 309-405.

Grmec, et al. Vasopressin improves outcome in out-of-hospital cardiopulmonary resuscitation of ventricular fibrillation and pulseless ventricular tachycardia: a observational cohort study. Crit Care. Feb. 2006;10(1):R13 (7 pages).

Gupta, et al. Inflammation: imaging with methoxy poly(ethylene glycol)-poly-L-lysine-DTPA, a long-circulating graft copolymer. Radiology. Dec. 1995;197(3):665-9.

Hakanson, et al. Evidence that gastrin enhances 45Ca uptake into bone through release of a gastric hormone. Regul Pept. 1990; 28(1):107-118.

Halter, et al Effect of acid inhibition on the growth of parital cells. Scand J Gastroenterol Suppl. 1986; 125:9-13.

Hansen, et al. Pharmcokinetics and organ metabolism of carboxyamidated and glycine-extended gastrins in pigs. Am J Physiol. 1996; 271:G156-163.

Heidel, et al. Administration in non-human primates of escalating intravenous doses of targeted nanoparticles containing ribonucleotide reductase subunit M2 siRNA. Proc Natl Acad Sci U S A. Apr. 3, 2007;104(14):5715-21.

Hrkach, et al. Synthesis of Poly(L-lactic acid-L-lycine) Graft Copolymers. Macromolecules. 1995; 4736-4739.

Hudecz, et al. Influence of carrier on biodistribution and in vitro cytotoxicity of methotrexate-branched polypeptide conjugates. Bioconjug Chem. 1993; 4(1):25-33.

Hui, et al. Glucagon-Like Peptide 1 Induces Differentiation of Islet Duodenal Homeobox-1-Positive Pancreatic Ductal Cells Into Insulin-Secreting Cells. Diabetes. 2001; 785-796.

Huotari, et al. Growth factor-mediated proliferation and differentiation of insulin-producing INS-1and PINm5F cells: identification of betacellulin as a novel beta-cellmitogen. Endocrinology. 1998; 139(4):1494-1499.

Im, et al. Irreversible inactiviation of rat gastric (H+-K+)-ATPase in vivo by omeprazole. Biochem Biophys Res Commun. 1985; 126(1): 78-82.

Keeling, et al. Studies on the mechanism of action of omeprazole. Biochem Pharmacol. 1985; 34(16):2967-2973.

Klinkenberg-Knol, E. The role of omeprazole in healing and prevention of reflux disease. Hepatogastroenterology. 1992; 39:27-30.

Kollen, et al. Gluconoylated and glycosylated polylysines as vectors for gene transfer into cystic fibrosis airway epithelial cells. Hum Gene Ther. 1996; 7(13):1577-86.

Koop, et al. Serum Gastrin levels during long-term omeprazole treatment. Aliment Pharmacol Ther. 1990; 4(2):131-138.

Kubo, et al. Chemically modified symmetric and asymmetric duplex RNAs: an enhanced stability to nuclease degradation and gene silencing effect. Biochem Biophys Res Commun. Jan. 4, 2008;365(1):54-61.

Lamberts, et al. Long-term omeprazole treatment in man: effects on gastric endocrine cell populations. Digestion. 1988; 39(2): 126-135.

Lapidot, et al. Use of esters of N-hydroxysuccinimide in the synthesis of N-acylamino acids. J Lipid Res. Mar. 1967;8(2):142-5.

Larson, et al. Omeprazole-induced hypergastrinemia: role of gastric acidity. J Surg Res. 1986; 40(5):504-509.

Larson, et al. Relationship of omeprazole-induced hypergastrinemia to gastric pH. Surgery. 1986; 100(2):175-180.

Leonard, et al. Trimethylene Bridges as Synthetic Spacers for the Detection of Intramolecular Interactions. Americal Chemical Society. 1979; 423-429.

Lev-Ran, et al. Origin of urinary epidermal growth factor in humans: excretion of endogenous EGF and infused [131I]-human EGF and kidney histochemistry. Clin Exp Pharmacol Physiol. 1992; 19(10):667-673.

March. Quantitative Treatments of the Effect of Structure on Reactivity. Advanced Organic Chemistry. MeGraw Hill Book Company. New York, 1977; 251-259.

Nielsen, et al. Pharmacology of exenatide (synthetic exendin-4) for the treatment of type 2 diabetes. Curr Opin Investig Drugs. Apr. 2003;4(4):401-5.

Nimesh, et al. Novel polyallylamine-dextran sulfate-DNA nanoplexes: highly efficient non-viral vector for gene delivery. Int J Pharm. Aug. 31, 2006;320(1-2):143-9.

Oliveira, et al. Targeted Delivery of siRNA. J Biomed Biotechnol. 2006;1-9.

Otto, et al. Recognition and separation of isoenzymes by metal chelates: Immobilized metal ion affinity partitioning of lactate dehydrogenase isoenzymes. Journal of Chromatography. 1993; 644: 25-33.

Patel, et al. Cell penetrating peptides: intracellular pathways and pharmaceutical perspectives. Pharm Res. Nov. 2007;24(11):1977-92.

Perry, et al. The glucagon-like peptides: a double-edged therapeutic sword? Trends Pharmacol Sci. Jul. 2003;24(7):377-83.

Prosser, et al. Novel chelate-induced magnetic alignment of biological membranes. Biophys J. Nov. 1998;75(5):2163-9.

Rostin, et al. B-Domain deleted recombinant coagulation factor VIII modified with monomethoxy polyethylene glycol. Bioconjug Chem. May-Jun. 2000;11(3):387-96.

Schentag, et al. Pharmacokinetics and pharmacodynamics of acid-suppressive agents in patents with gastroesophageal reflux disease. Am J Hosp Pharm. 1993; 50:S7-10.

Schiffelers, et al. Cancer siRNA therapy by tumor selective delivery with ligand-targeted sterically stabilized nanoparticle. Nucleic Acids Res. Nov. 1, 2004;32(19):e149.

(56) References Cited

OTHER PUBLICATIONS

Scrocchi, et al. Identification of glucagon-like peptide 1 (GLP-1) actions essential for glucose homeostasis in mice with disruption of GLP-1 receptor signaling. Diabetes. Apr. 1998;47(4):632-9.
Senekowitsch-Schmidtke, et al. In vivo evaluation of epidermal growth factor (EGF) receptor density on human tumor xenografts using radiolabeled EGF and anti-(EGF receptor) mAb 425. Cancer Immunol Immunother. 1996; 42(2): 108-114.
Shapiro, et al. Clinical islet transplant: current and future directions towards tolerance. Immunol Rev. Dec. 2003;196:219-36.
Simeoni, et al. Insight into the mechanism of the peptide-based gene delivery system MPG: implications for delivery of siRNA into mammalian cells. Nucleic Acids Res. Jun. 1, 2003;31(11):2717-24.
Song, et al. Expansion of Pdx1-expressing pancreatic epithelium and islet neogenesis in transgenix mice overexpression transforming growth factor alpha. Gastroenterology. 1999; 117(6):1416-1426.
Sontheimer, et al. Silence from within: endogenous siRNAs and miRNAs. Cell. Jul. 15, 2005;122(1):9-12.
Sparado, et al. A convenient manual trinitrobenzenesulfonic acid method for monitoring amino acids and peptides in chromatographic column effluents. Anal Biochem. 1979; 96:317-321.
Suarez-Pinzon, et al. Combination therapy with epidermal growth factors and gastrin increses beta-cells mass and reverses hyperglycemia in diabetic NOD mice. Diabetes. 2005; 54(9):2596-2601.
Suginoshita, et al. Liver targeting of human interferon-beta with pullulan based on metal coordination. J Control Release. Sep. 18, 2002;83(1):75-88.
Suginoshita, et al. Liver targeting of interferon-beta with a liver-affinity polysaccharide based on metal coordination in mice. J Pharmacol Exp Ther. Aug. 2001;298(2):805-11.
Tabata, et al. Growth factor release from amylopectin hydrogel based on copper coordination. J Control Release. Dec. 4, 1998;56(1-3):135-48.
Tabata, et al. Targeting of tumor necrosis factor to tumor by use of dextran and metal coordination. J Control Release. May 20, 1999;59(2):187-96.
Terpe, K. Overview of tag protein fusions: from molecular and biochemical fundamentals to commercial systems. Appl Microbiol Biotechnol. Jan. 2003;60(5):523-33.
Tourrel, et al. Glucagon-like peptide-1 and exendin-4 stimulate beta-cell neogenesis in streptozotocin-treated newborn rats resulting in persistently improved glucose homeostasis at adult age. Diabetes. Jul. 2001;50(7):1562-70.
Urusova, et al. GLP-1 inhibition of pancreatic islet cell apoptosis. Trends Endocrinol Metab. Jan.-Feb. 2004;15(1):27-33.
Van Broekhoven, et al. A novel system for convenient detection of low-affinity receptor-ligand interactions: chelator-lipid liposomes engrafted with recombinant CD4 bind to cells expressing MHC class II. Immunol Cell Biol. Jun. 2001;79(3):274-84.
Van Nieuwenhove, et al. Gastrin stimulates epithelial cell proliferation in the oesophagus of rats. Virchows Arch. 1998; 432(4): 371-375.
Wagner. Delivery of drugs, protein and genes into cells using transferrin as a ligand for receptor-mediated endocytosis. Advanced drug delivery reviews. 1994; 14: 113-135.
Weast, R. Periodic Table of Elements. Handbook of Chemistry and Physics. CAS Version. 67th Ed. Boca Raton, FL. CRC Press. 1986-1987; inside cover.
Wenzel, et al. A Comparison of Vasopressin and Epinephrine for Out-of-Hospital Cardiopulmonary Resuscitation. N Engl J Med 2004;350:105-113.
Wiedeman, et al. Dipeptidyl peptidase IV inhibitors for the treatment of impaired glucose tolerance and type 2 diabetes. Curr Opin Investig Drugs. Apr. 2003;4(4):412-20.
Wolfrum, et al. Mechanisms and optimization of in vivo delivery of lipophilic siRNAs. Nat Biotechnol. Oct. 2007;25(10):1149-57.
Xu, et al. Exendin-4 stimulates both beta-cell replication and neogenesis, resulting in increased beta-cell mass and improved glucose tolerance in diabetic rats. Diabetes. Dec. 1999;48(12):2270-6.
Yamamoto, et al. Recombinant human betacellulin promotes the neogenesis of beta-cells and ameliorates glucos intolerance in mice with diabetes induced by selective alloxan perfusion. Diabetes. 2000; 49(12): 2021-2027.
Yu, et al. Pharmacokinetic and pharmacodynamic evaluation of a novel proton pump inhibitor, YH1885, in healthy volunteer. J Clin Pharmacol. 2004; 44(1):73-82.
Zhou, et al. DNA transfection mediated by cationic liposomes containing lipopolylysine: characterization and mechanism of action. Biochim Biophys Acta. 1994; 1189(2):195-203.
Zhou, et al. Lipophilic polylysines mediate efficient DNA transfection in mammalian cells. Biochim Biophys Acta. 1991; 1065(1):8-14.
International search report dated Jan. 6, 2009 for PCT Application No. US2008/72148.
International search report dated Feb. 26, 2009 for PCT Application No. US2008/83687.
Porath, et al. Metal chelate affinity chromatography, a new approach to protein fractionation. Nature. Dec. 18, 1975;258(5536):598-9.
Office action dated Dec. 15, 2009 for U.S. Appl. No. 11/613,183.
Office action dated Jul. 20, 2009 for U.S. Appl. No. 11/428,803.
PharmaIn—Enabling and improving human therapeutics. PharmaIn Introduction. Oct. 2009. Available at http://www.pharmain.com/PDF/PharmaIN%20BD%20Presentation%20Slides__16OCT09.pdf. Accessed Mar. 24, 2010.
Behlke, M. Progress towards in vivo use of siRNAs. Mol Ther. Apr. 2006;13(4):644-70.
Chollet, et al. Side-effects of a systemic injection of linear polyethylenimine-DNA complexes. J Gene Med. Jan.-Feb. 2002;4(1):84-91.
Kim, et al. PEG conjugated VEGF siRNA for anti-angiogenic gene therapy. J Control Release. Nov. 28, 2006;116(2):123-9.
Paramonov, et al. Self-assembly of peptide-amphiphile nanofibers: the roles of hydrogen bonding and amphiphilic packing. J Am Chem Soc. Jun. 7, 2006;128(22):7291-8.
Holm, et al. Side-chain and backbone amide bond requirements for glycopeptide stimulation of T-cells obtained in a mouse model for rheumatoid arthritis. Bioorg Med Chem. Sep. 1, 2006;14(17):5921-32. Epub Jun. 9, 2006.
Office action dated Feb. 14, 2011 for U.S. Appl. No. 12/184,186.
Office action dated Mar. 11, 2011 for U.S. Appl. No. 12/271,732.
Office action dated Apr. 8, 2010 for U.S. Appl. No. 12/271,732.
Office action dated Oct. 8, 2010 for U.S. Appl. No. 12/184,186.
Office action dated Nov. 15, 2010 for U.S. Appl. No. 12/271,732.
Office action dated Nov. 9, 2012 for U.S. Appl. No. 13/095,753.

\* cited by examiner isothiocyanate        thiourea

Succinimidyl ester        carboxamide

Sulfonyl Chloride    sulfonamide

∿∿ Oligonucleotide group

⇔ Carrier

⊙∿∿ Oligonucleotide or Oligonucleotide containing load molecule

∿∿∿ Oligonucleotide group

⇐⇒ Carrier

∘∿∿∿ Oligonucleotide or Oligonucleotide containing load molecule

⬤━━━ Protective Chain

⊃ Targeting Molecule

OLIGONUCLEOTIDE CORE CARRIER COMPOSITIONS FOR DELIVERY OF NUCLEIC ACID-CONTAINING THERAPEUTIC AGENTS, METHODS OF MAKING AND USING THE SAME

RELATED APPLICATION INFORMATION

This application claims the benefit of priority under 35 U.S.C. 119(e) to U.S. Provisional Application No. 60/956,916 filed Aug. 20, 2007.

BACKGROUND OF THE INVENTION

The development of new oligonucleotide drug formulations and other systems for administration of physiologically active oligonucleotides, such as RNA and DNA, or physiologically active peptides and proteins is driven by the need to achieve the desirable physiological effects. With respect to RNA oligonucleotides, many of them have been observed to be unstable in biological environment due to abundance of RNAses. Therefore they need to be stabilized or protected and/or delivered via systemic circulation either by infusion or repeated injection. In addition, oligonucleotides that have low molecular masses are expected to have short biological half-life due to their efficient removal from systemic circulation via kidneys. In addition, a fraction of these oligonucleotides are expected to be removed via reticuloendothelial uptake due to recognition by monocyte/macrophages or as a result of opsonization by complement components.

In part to circumvent rapid oligonucleotide degradation, either repeated injection or a continuous systemic infusion of oligonucleotides via a pump can be employed. Infusion strategy can be effective but may be impractical for outpatients requiring high levels of mobility, associated disadvantages of quality of life and potential intravenous (I.V.) line infections. Another approach is deliver oligonucleotides using implantable pump comprised of a capsule with a membrane allowing diffusion of the oligonucleotides, for example, at a desirable release rate. Due to lack of protection after release from these capsules, oligonucleotides will have difficulty reaching the target tissue before being degraded by RNAses or DNAses, taken up by non-target cells such as monocyte/macrophages or as a result of opsonization by complement components. Oligonucloetides can also be released into the extracellular space and distributed and degraded in the lymphatics. Overall concentration of oligonucleotides may be affected by local lymph node activity and the efficacy of lymph node drainage of the implantation site. There is also a potential of host reaction to capsule material but in general, this side effect is expected to be infrequent. The oligonucleotide release system can also be made biodegradable as a result of encapsulation or inclusion into degradable drug delivery vehicles or carriers, e.g. polymeric matrices, particles or membrane vesicles (liposomes). These delivery systems can be either implantable or injectable. Implantable oligonucleotide delivery systems can be placed under the epidermis where the components of the system are usually slowly degraded as a result of biological activity of surrounding cells (i.e. as a result of the release of enzymes degrading chemical bonds that hold these implants together).

U.S. Pat. No. 5,871,710 to Bogdanov et al. which hereby incorporated by reference discloses a biocompatible graft co-polymer adduct including a polymeric carrier, a protective chain linked to the polymeric carrier, a reporter group linked to the carrier or to the carrier and protective chain, and a reversibly linked Pt(II) compound for therapeutics. In Bogdanov et. al., the linkage between the reporter group and platinum is coordinate binding. However, Bogdanov et al. did not disclose an oligonucleotide delivery composition wherein the oligonucleotide to be delivered is hydrogen bonded to a complementary oligonucleotide covalently linked to the carrier and has a means of adjusting the release rates by varying the number of hydrogen bonding. As for example the hydrogen bonding of a U.S. Pat. No. 7,138,105 to Bolotin which hereby incorporated by reference discloses a biocompatible graft co-polymer comprising of a metal bridge flanked by two metal binding molecule wherein one of the metal binding molecule is part of or covalently linked to the therapeutic agent. The bridge provides a link between the carrier and therapeutic agent capable of binding metals. The linkage is by coordinate bonding and not by hydrogen bonding as in oligonucleotide binding to its complement, which is the subject of the present invention.

It has been over a decade since oligonucleotide such as siRNA and antisense RNA and DNA was discovered. However their therapeutic potential remains unrealized due to their rapid degradation and instability in vivo. In order, for oligonucleotide to be effective in inhibiting translation of specific genes, large doses are required which often induces toxicity to the organism being treated. The toxicity is not related to inhibition of translation of target genes but due to the overwhelming amount of materials being used (over 10 mg/kg). For over 10 years now, there is a long felt need to stabilized oligonucleotide in biological fluid to realize the promised potential of oligonucleotide therapies. There exists a need for a sustained release oligonucleotide delivery system that works for a wide range of oligonucleotides and where the release rate is readily controlled. The instant application discloses a biocompatible composition comprising of an oligonucleotide core that can reversibly bind an essentially complementary oligonucleotide, wherein the number of bases in the complementary oligonucleotide core can be altered to control the release rate of the reversibly bound oligonucleotide by increasing or decreasing the number of bases and thus the number of hydrogen bonds. The type and number of complementing bases determine the association constant (Ka) or dissociation constant (Kd) which then determines the amount of free oligonucleotide at any given condition. The concentration of free oligonucleotide and the further release of oligonucleotide from the carrier when the concentration of free oligonucleotide goes down is the result of the desire of the system to achieve the equilibrium constant (Ka or Kd).

SUMMARY OF THE INVENTION

It is an object of the present invention to provide a sustained release therapeutic agent delivery system that is safe, biocompatible, readily prepared from known chemistries and compounds, amenable to a wide variety of oligonucleotides or oligonucleotide containing therapeutic agents, and where the release rate can be readily adjusted by simple mechanisms of altering the number of bases in the oligonucleotide core of the delivery system.

It is a further object of the present invention that the sustained release delivery system includes a targeting moiety for efficient delivery of the oligonucleotide agent to a site in need thereof. Such site can be a specific location or organ in mammals such as human.

It is another object of the present invention to provide a method of treating a disorder by delivering an oligonucleotide agent to a patient in need thereof in a controlled manner and at a release rate that is safe and effective and readily adjusted to be so.

The subject invention results from the realization that the number of hydrogen bonding interactions between the oligonucleotide in the carrier systems of the present invention and the complementary oligonucleotide may be readily adjusted to control the release of the complementary oligonucleotide, or in a broader sense, a "load molecule." Carriers that are safe and non-immunogenic or made non-immunogenic by the presence of "protective chains" may be easily prepared to contain plurality of oligonucleotide. The carrier can be made to have both high loading capacity and adjustable release rates for the load oligonucleotide containing molecule by controlling the number of hydrogen bonding or length of complementary oligonucleotide core within the carrier.

In part, the present invention is directed towards novel oligonucleotide delivery systems, and methods of making and using the same.

The present invention is primarily directed to an oligonucleotide-core carrier composition comprising oligonucleotides covalently attached to a carrier and an essentially complementary oligonucleotide agent of interest (load molecule) bound to the oligonucleotide of the carrier by hydrogen bonding.

In one embodiment, the present invention relates to a biocompatible oligonucleotide-core carrier composition comprising: (i) a polymeric carrier comprising a backbone wherein the carrier is polylysine, polyaspartic acid, polyglutamic acid, polyserine, polythreonine, polycysteine, polyglycerol, polyethyleneimines, polyallylamine, chitosan, natural saccharides, aminated polysaccharides, aminated oligosaccharides, polyamidoamine, polyacrylic acids, polyalcohols, sulfonated polysaccharides, sulfonated oligosaccharides, carboxylated polysaccharides, carboxylated oligosaccharides, aminocarboxylated polysaccharides, aminocarboxylated oligosaccharides, carboxymethylated polysaccharides, or carboxymethylated oligosaccharides; and (ii) a plurality of oligonucleotides covalently linked to the polymeric carrier, wherein each oligonucleotide has 2 to 100 bases in length, wherein the oligonucleotide group is essentially complementary to the (or a portion) of the oligonucleotide-containing molecule or siRNA to be delivered.

In another embodiment, the present invention relates to a biocompatible oligonucleotide-core carrier composition comprising (i) a carrier comprising a backbone; (ii) a plurality of oligonucleotide groups covalently linked to the carrier, and each has 2 to 100 bases in length; and (iii) a plurality of polymeric protective side chains, wherein each protective side chain is covalently linked to the carrier and each has a molecular weight between about 400 and 20,000 Daltons independent of the carrier weight. In a further embodiment, the aforementioned composition further comprises a second set of oligonucleotide groups with covalently linked protective side chains, wherein the oligonucleotide group has a first and second end, the first end is covalently linked to the carrier, the second end is covalently linked to the protective side chain; the oligonucleotide group is 2-100 bases in length; and the protective side chain linked to the oligonucleotide group has a molecular weight between 400 and 20,000 Daltons independent of the oligonucleotide group weight.

In another embodiment, the present invention relates to a biocompatible oligonucleotide-core carrier composition comprising (i) a carrier comprising a backbone; (ii) a plurality of oligonucleotide groups covalently linked, to the carrier, and each has a 2 to 100 bases in length; and (iii) a second set of oligonucleotide groups with a covalently linked protective side chain, wherein each of the oligonucleotide in the second set has a first and second end, the first end is covalently linked to the carrier, the second end is covalently linked to the protective side chain; the oligonucleotide group is 2 to 100 bases in length; and the protective side chain linked to the oligonucleotide group has a molecular weight between 400 and 20,000 Daltons independent of the oligonucleotide group weight.

In another embodiment, the present invention relates to a biocompatible oligonucleotide-core carrier composition, comprising: (i) a carrier comprising a backbone; and (ii) a plurality of oligonucleotide groups with a covalently linked protective side chain, wherein the oligonucleotide group has a first and second end; the first end is covalently linked to the carrier, the second end is covalently linked to the protective side chain; the oligonucleotide group has 2 to 100 bases length, and; the protective side chain has a molecular weight between about 400 and 20,000 Daltons independent of the carrier and oligonucleotide group weights.

In a further embodiment the present invention relates to any of the aforementioned compositions, wherein the oligonucleotide group comprises DNA or RNA. In a further embodiment, the oligonucleotide group comprises methoxylated DNA or RNA.

In another embodiment, the present invention relates to any of the aforementioned compositions with protective chain, wherein the protective side chain comprises anyone from a group consisting of polyethyleneglycol, polypropylene glycol, a co-polymer of polyethyleneglycol and polypropyleneglycol, methoxypolyethyleneglycol, methoxypolypropyleneglycol, or a co-polymer of methoxypolyethyleneglycol and methoxypolypropyleneglycol. In a further embodiment, the protective side chain comprises a co-polymer of polyethyleneglycol including a monoester of a dicarboxylic acid. In a further embodiment, the protective side chain comprises a sialic acid chain. In a further embodiment, the protective side chain has a molecular weight of 500-20,000 Daltons. In a further embodiment, the protective side chain comprises a monoesterified derivative thereof, preferably methoxypolyethyleneglycol-ester, methoxypolypropyleneglycol-ester, or a co-polymer of methoxypolyethyleneglycol and methoxypolypropyleneglycol-ester. In a further embodiment, the protective side chain comprises anyone of; polyethyleneglycol monoamine, methoxypolyethyleneglycol monoamine, polypropyleneglycol monoamine, methoxypolypropyleneglycol monoamine, polyethyleneglycol hydrazine, methoxypolyethyleneglycol hydrazine, polypropyleneglycol hydrazine, methoxypolypropyleneglycol hydrazine, polyethyleneglycol imidazolide, methoxypolyethyleneglycol imidazolide, polypropyleneglycol imidazolide, methoxypolypropyleneglycol imidazolide, polyethyleneglycol diacid, methoxypolyethyleneglycol diacid, polypropyleneglycol diacid, methoxypolypropyleneglycol diacid, wherein the terminal amine, hydrazine, imidazolide, or acid is used to attached to the carrier, oligonucleotide group, or targeting molecule. In a further embodiment, the protective side chain is linked to the carrier or oligonucleotide group of the carrier (not load oligonucleotide) by preferably a single linkage.

In another embodiment, the present invention relates to anyone of the aforementioned compositions with protective chain and carrier, wherein the carrier comprises anyone of the group consisting of; solid support, nanoparticle, and microparticle. In a further embodiment the carrier comprises a block co-polymer. In a further embodiment the carrier comprises a polymeric carrier. In a further embodiment, the polymeric carrier is selected from the group consisting of polyamino acids, polyethyleneimines, polyallyamine, chitosan, natural saccharides, aminated polysaccharides, aminated oligosaccharides, polyamidoamine, polyacrylic acids, polyalcohols, sulfonated polysaccharides, sulfonated oligosaccharides, carboxylated polysaccharides, carboxylated oligosaccharides, aminocarboxylated polysaccharides, aminocarboxylated oligosaccharides, carboxymethylated polysaccharides, and carboxymethylated oligosaccharides. In a further embodiment, the polymeric carrier is a polyamino acid having 2 to 560 amino acid units. In a further embodiment, the polymeric carrier is a polyamino acid having a molecular weight of 1,000-100,000 Daltons. In a further embodiment the polymeric carrier is a polyamino acid consisting of a single species of amino acid. In a further embodiment, the polymeric carrier is a polyamino acid comprising of at least two different species of amino acids. In a further embodiment the polymeric carrier is a polyamino acid and wherein the polyamino acid is a block co-polymer. In a further embodiment the polymeric carrier is a polyamino acid and wherein the polyamino acid comprises polyamino acid fragments linked by cleavable bonds. In a further embodiment the cleavable bonds are S—S bonds. In a further embodiment the polymeric carrier is a polyamino acid selected from the group consisting of poly-L-lysine, poly-D-lysine, poly-alpha,beta-(2-aminoethyl)-D,L aspartamide, poly-L-aspartic acid, poly-D-aspartic acid, poly-L-glutamic acid, poly-D-glutamic acid, poly-L-serine, poly-D-serine, poly-L-threonine, poly-D-threonine, poly-L-tyrosine, or poly-D-tyrosine. In a further embodiment the polymeric carrier is a polyamino acid and the polyamino acid is non-proteinaceous.

In another embodiment, the present invention relates to any of the aforementioned compositions further comprising of targeting molecules covalently attached to the protective chains, oligonucleotide groups or the carrier. In a further embodiment, the present invention relates to any of the aforementioned compositions with targeting molecule, wherein the targeting molecule is selected from the group consisting of an antibody, fragment of an antibody, chimeric antibody, enzyme, quasi-substrate of enzymes, lectin, saccharide ligand, peptide, protein, receptor ligand, cell surface binding protein, cell surface binding peptide, cell surface binding compound, extracellular matrix binding peptide, extracellular matrix binding protein, extracellular matrix binding compounds.

In another embodiment, the present invention relates to any of the aforementioned compositions further comprising load molecule, wherein load molecule is any molecule containing oligonucleotide sequence complementary to the oligonucleotide sequence covalently bonded to any of the aforementioned compositions. In a further embodiment, the present invention relates to any of the aforementioned compositions further comprising any combination of load molecules dissociably linked to the oligonucleotide groups, targeting molecules, orienting molecules, and/or protective side chains. In a further embodiment, the load molecule is an oligonucleotide imaging agent. In a further embodiment, the load molecule is an oligonucleotide containing therapeutic agent. In a further embodiment, the oligonucleotide containing therapeutic agent is cytokine, lymphokine, hormone, hormone agonist, hormone antagonist, antibiotic, analgesic, toxin, photo-toxin, cytostatic agent, cytotoxic agent, psychotropic agent, steroidal anti-inflammatory agent, non-steroidal anti-inflammatory agent, immunosuppressive agent, anti-bacterial agent, anti-viral drug, anti-fungal drug, chelator, vitamin, protease inhibitor, pesticide, aminoglycoside, polymyxin, ACE inhibitor, peptide, protein, antibody, antibody fragment, recombinant peptide, peptide isolated from plants, peptide isolated from fungi, peptide isolated from animals, peptide isolated from bacteria, peptide isolated from viruses, peptides isolated from cells in culture, synthetic peptide, peptidomimetic compound, organic compound, synthetic organic compound, organic compound isolated from plants, organic compound isolated from fungi, organic compound isolated from animals, organic compound isolated from bacteria, organic compound isolated from viruses, organic compound isolated from cells in culture, organometallic compound, deoxyribonucleic acid, ribonucleic acid, small interfering ribonucleic acid (siRNA), oligonucleotide, nucleic acid derivative, oligosaccharide, carbohydrate; lipid; photo-sensitive organic compound, and proteoglycan. Oligonucleotide can be attached to those load molecules above that does not naturally contain oligonucleotide.

In another embodiment, the present invention relates to any of the aforementioned compositions with load molecule, wherein the load molecule is an oligonucleotide-containing therapeutic agent selected from the group consisting of siRNA, antisense-DNA, antisense-RNA, glucagon-like-peptide, glucagon-like-peptide derivatives, exenatide, glucagon-like-peptide-1, glucagon-like-peptide-2, leptin fragment, Gastric inhibitory polypeptide(GIP), Epidermal Growth Factor (EGF) receptor ligand, EGF, Tranforming Growth Factor alpha (TGF-alpha), Betacellulin, Gastrin/Cholecystokinin receptor ligand, Gastrin, Cholecystokinin, lysostaphin, interferon, interferon gamma, interferon beta, interferon alpha, interleukin-1, interleukin-2, interleukin-4, interleukin-6, interleukin-8, interleukin-10, interleukin-12, tumor necrosis factor, tumor necrosis factor alpha, tumor necrosis factor beta, auristatin, nisin, insulin, insulin-like growth factor, growth hormone, growth hormone releasing hormone (GHRH), nerve growth factor, brain-derived neurotrophic factor, enzymes, endostatin, angiostatin, trombospondin, urokinase, streptokinase, blood clotting factor VII, blood dotting factor VIII, granulucyte-macrophage colony-stimulating factor (GM-CSF), granulucyte colony-stimulating factor (G-CSF), thrombopoetin, calcitonin, parathyroid hormone (PTH) and its fragments, erythropoietin, atrial natriuretic factor, monoclonal antibodies, monoclonal antibody fragments, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastin, prostaglandins, epoprostenol, prostacyclin, cyclosporine, vasopressin, terlipressin, desmopressin, cromolyn sodium (sodium or disodium chromoglycate), vasoactive intestinal peptide (VIP), vancomycin, antimicrobials, polymyxin b, anti-fungal agents, anti-viral agents, enfuvirtide, doxorubicin, etoposide, fentanyl, ketamine, and vitamins. In a further embodiment, the therapeutic agent is oligonucleotide-containing glucagon-like-peptde-1. In a further embodiment, the therapeutic agent is oligonucleotide-containing glucagon-like-peptide-2. In a further embodiment, the therapeutic agent is oligonucleotide-containing interferon. In a further embodiment, the therapeutic agent is oligonucleotide-containing interferon alpha. In a further embodiment, the therapeutic agent is oligonucleotide-containing interferon beta. In a further embodiment, the therapeutic agent is oligonucleotde-containing interferon gamma. In a further embodiment, the therapeutic agent is oligonucleotide-containing nisin. In a further embodiment, the therapeutic agent is oligonucleotide-containing Epidermal Growth Factor (EGF) receptor ligand. In a further embodiment, the therapeutic agent is oligonucleotide-containing EGF. In a further embodiment, the therapeutic agent is oligonucleotide-containing Tranforming Growth Factor alpha (TGF-alpha). In a further embodiment, the therapeutic agent is oligonucleotide-containing betacellulin. In a further embodiment, the therapeutic agent is oligonucleotide-containing Gastrin/Cholecystokinin receptor ligand. In a further embodiment, the therapeutic agent is oligonucleotide-containing Gastrin. In a further embodiment, the therapeutic agent is oligonucleotide-containing Cholecystokinin.

In another embodiment the present invention relates to a method of treating a patent for an infection comprising administering to the patient in need thereof a therapeutically effective amount of any of the oligonucleotide-core carrier compositions described above, wherein the load molecule is siRNA.

These embodiments of the present invention, other embodiments, and their features and characteristics, will be apparent from the description, drawings and claims that follow.

BRIEF DESCRIPTION OF DRAWINGS

FIG. 12. This shows that PLPEG based polymeric carrier (C18-20PLPEG5-55; this is a 20 kDa polylysine where 55% of the amino groups were reacted with PEG succinate of 5 kDa molecular weight and the remaining aminogroups were reacted with stearic acid or C18) binds peptides (e.g. GLP-1) with 4-5 sites with Kd in nanomolar range (249 nM). Other sites have lower affinity with two sites with Kd of 2.7 uM and another 2 sites with Kd of 33 uM. In this experiment 10 mg of carrier was loaded (as described in FIG. 34, acetone method) with varying amounts of GLP1. Each loaded carrier was dissolved in 1 ml PBS and allowed to equilibrate for 2 hours. Each solution containing free and bound GLP1 was filtered through 100 kDa molecular cut off filter and each filtrate containing free GLP1 was quantified by reverse phase HPLC. The bound GLP1 from each solution was released by 70% acetonitrile and similarly quantified by HPLC. This method can be used for the determination of Kd between oligonucleotide-containing carrier and the load molecule with complementary oligonucleotide-sequence.

Figure 13:
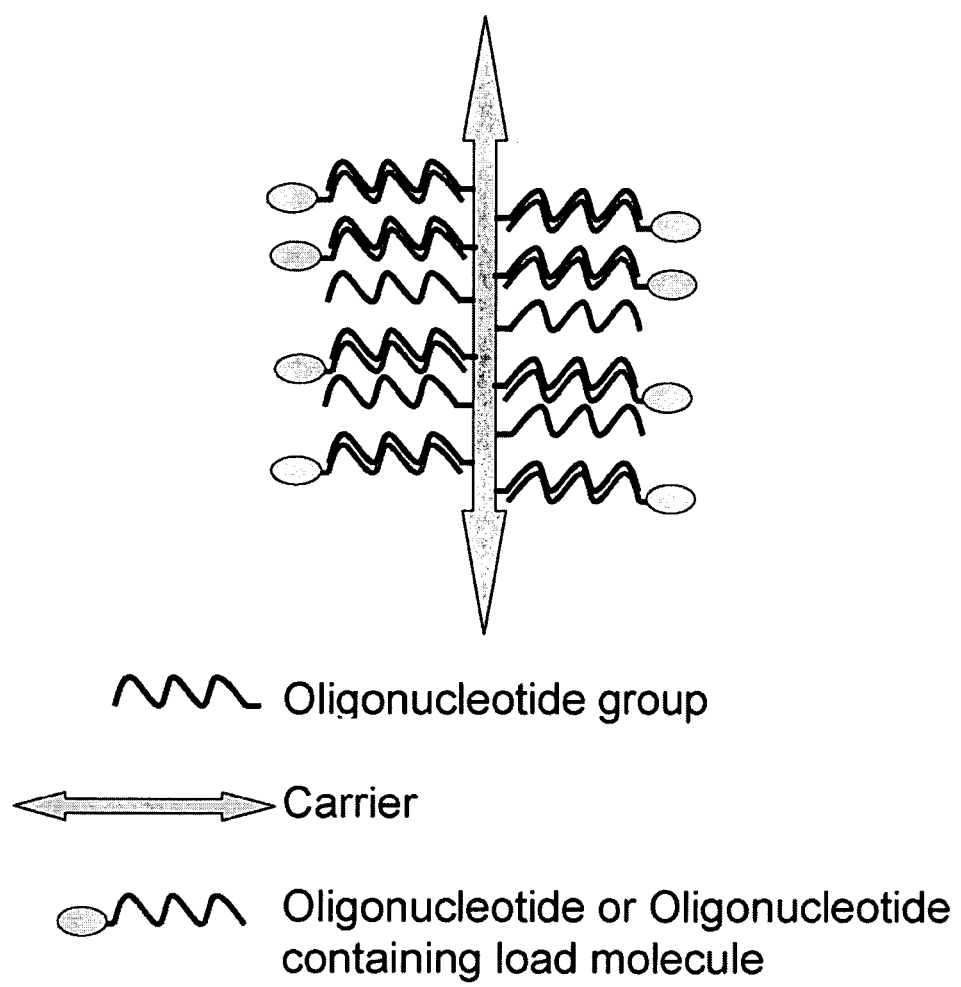

FIG. 13 depicts a diagram of one embodiment of the oligonucleotide-core composition of the present invention comprising; a carrier, an oligonucleotide group covalently linked to the carrier, and a load molecule which is either oligonucleotide or oligonucleotide-containing load molecule wherein the load oligonucleotide sequence is essentially complementary to the sequence oligonucleotide linked to the carrier.

Figure 14:
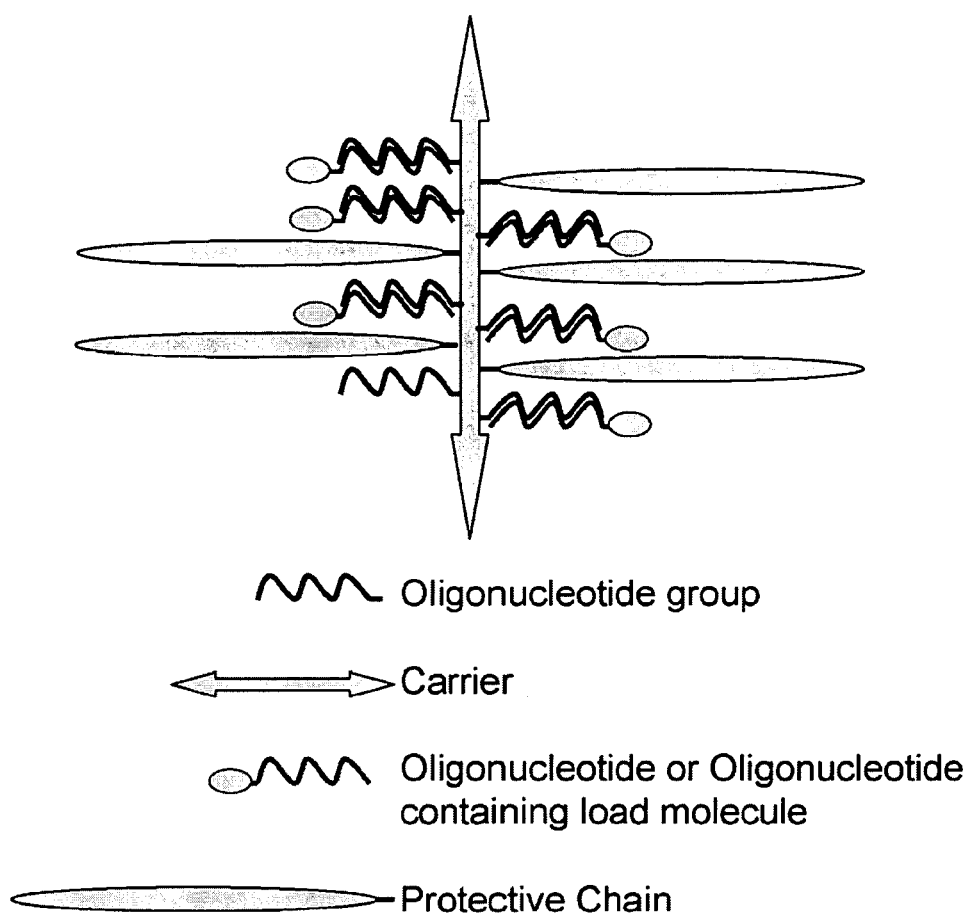

FIG. 14 depicts a diagram of one embodiment of the oligonucleotide-core composition of the present invention comprising; a carrier, an oligonucleotide group covalently linked to the carrier, a protective chain covalently linked to the carrier, and a load molecule which is either oligonucleotide or oligonucleotide-containing load molecule wherein the load oligonucleotide sequence is essentially complementary to the sequence oligonucleotide linked to the carrier.

Figure 15:
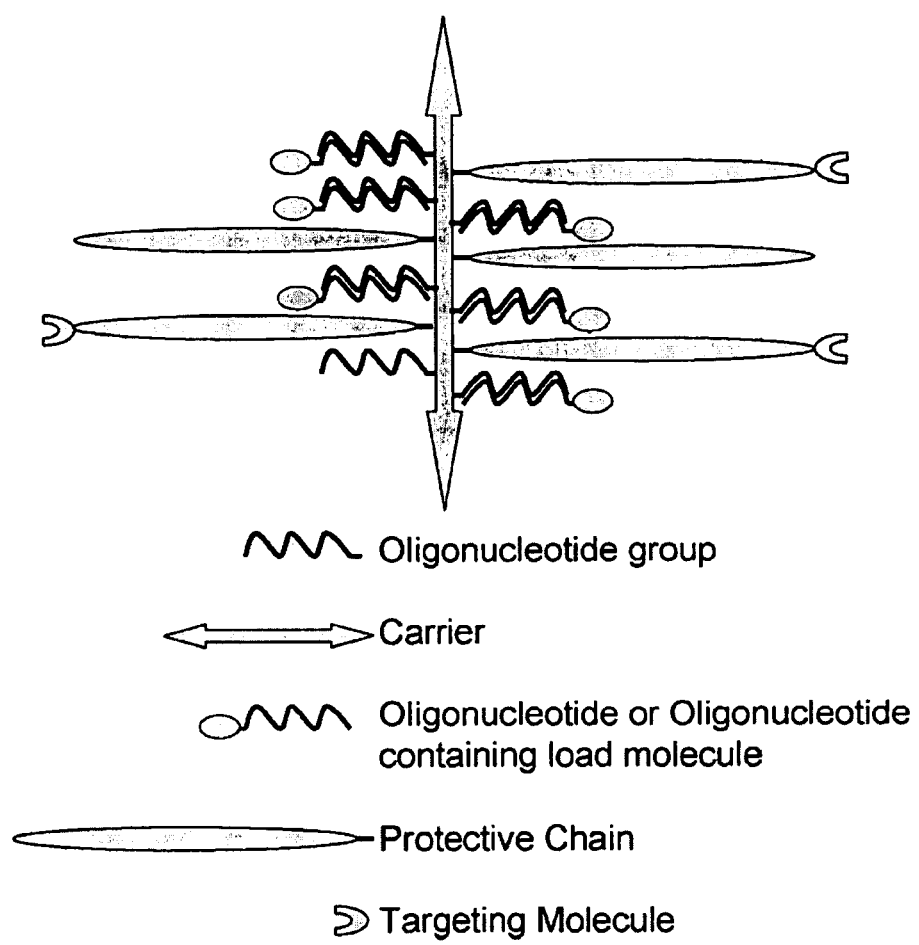

FIG. 15 depicts a diagram of one embodiment of the oligonucleotide-core compositions of the present invention comprising; a carrier, an oligonucleotide group covalently linked to the carrier, a protective chain covalently linked to the carrier, a targeting moiety covalently linked to the protective chain, and a load molecule which is either oligonucleotide or oligonucleotide-containing load molecule wherein the load oligonucleotide sequence is essentially complementary to the sequence oligonucleotide linked to the carrier.

Figure 16:
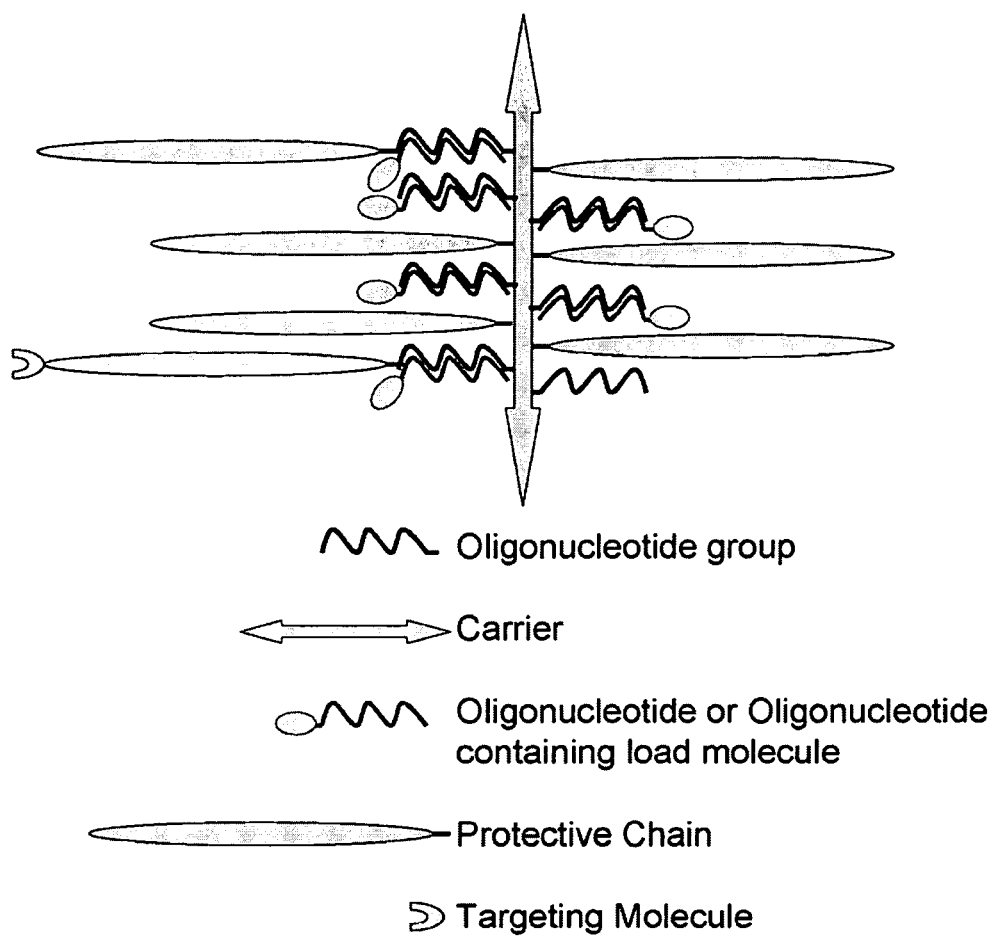

FIG. 16 depicts a diagram of one embodiment of the oligonucleotide-core compositions of the present invention comprising; a carrier, an oligonucleotide group covalently linked to the carrier, protective chains covalently linked to the carrier and/or oligonucleotide group, a targeting moiety covalently linked to oligonucleotide-linked protective chains, and a load molecule which is either oligonucleotide or oligonucleotide-containing load molecule wherein the load oligonucleotide sequence is essentially complementary to the sequence oligonucleotide linked to the carrier.

Figure 17:
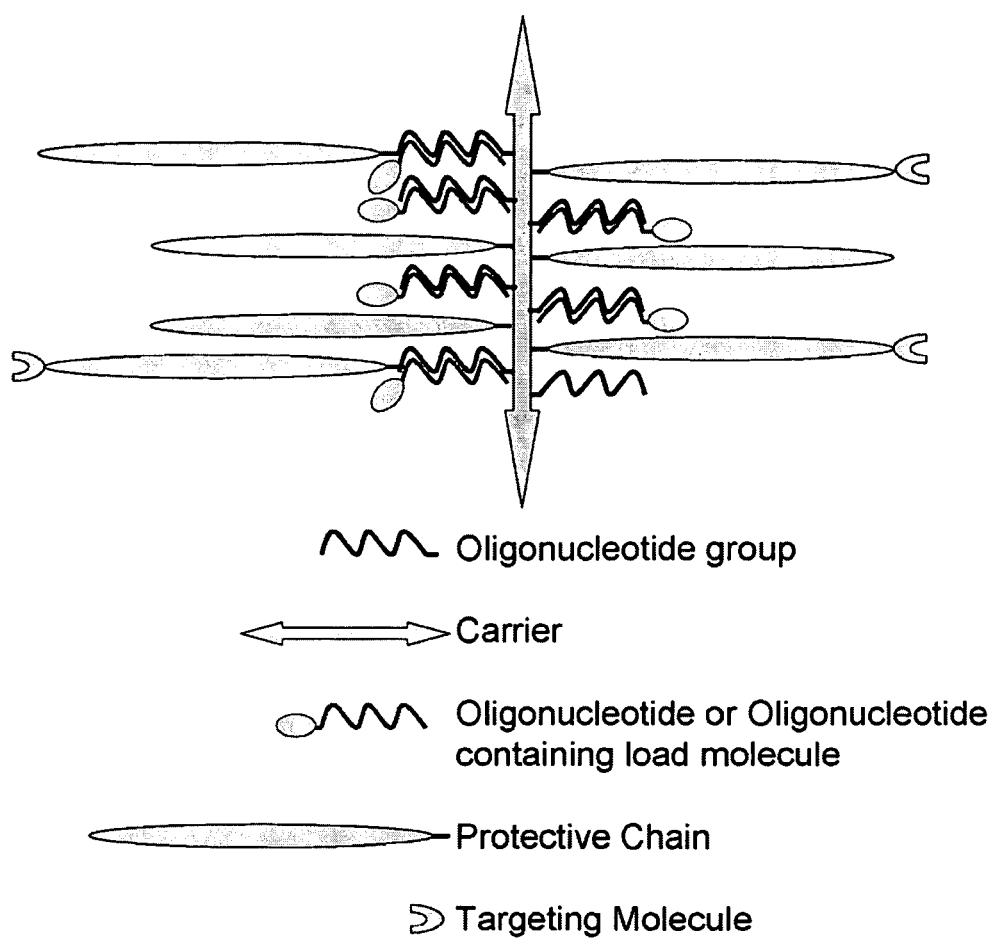

FIG. 17 depicts a diagram of one embodiment of the oligonucleotide-core compositions of the present invention comprising; a carrier, an oligonucleotide group covalently linked to the carrier, protective chains covalently linked to the carrier and/or oligonucleotide group, targeting moieties covalently linked to some of the protective chains, and a load molecule which is either oligonucleotide or oligonucleotide-containing load molecule wherein the load oligonucleotide sequence is essentially complementary to the sequence oligonucleotide linked to the carrier.

Figure 18:
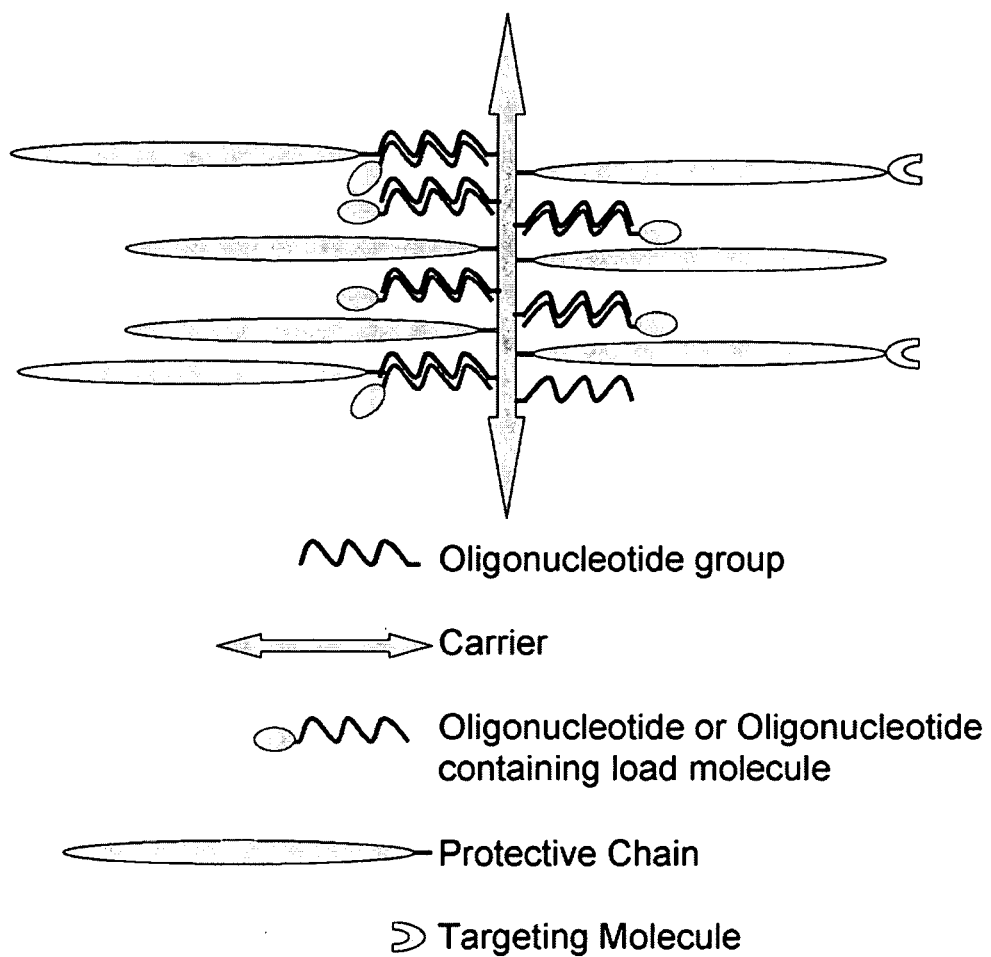

FIG. 18 depicts a diagram of one embodiment of the oligonucleotide-core compositions of the present invention comprising; a carrier, an oligonucleotide group covalently linked to the carrier, protective chains covalently linked to the carrier and/or oligonucleotide group, a targeting moiety covalently linked to carrier-linked protective chain, and a load molecule which is either oligonucleotide or oligonucleotide-containing load molecule wherein the load oligonucleotide sequence is essentially complementary to the sequence oligonucleotide linked to the carrier.

Figure 19:
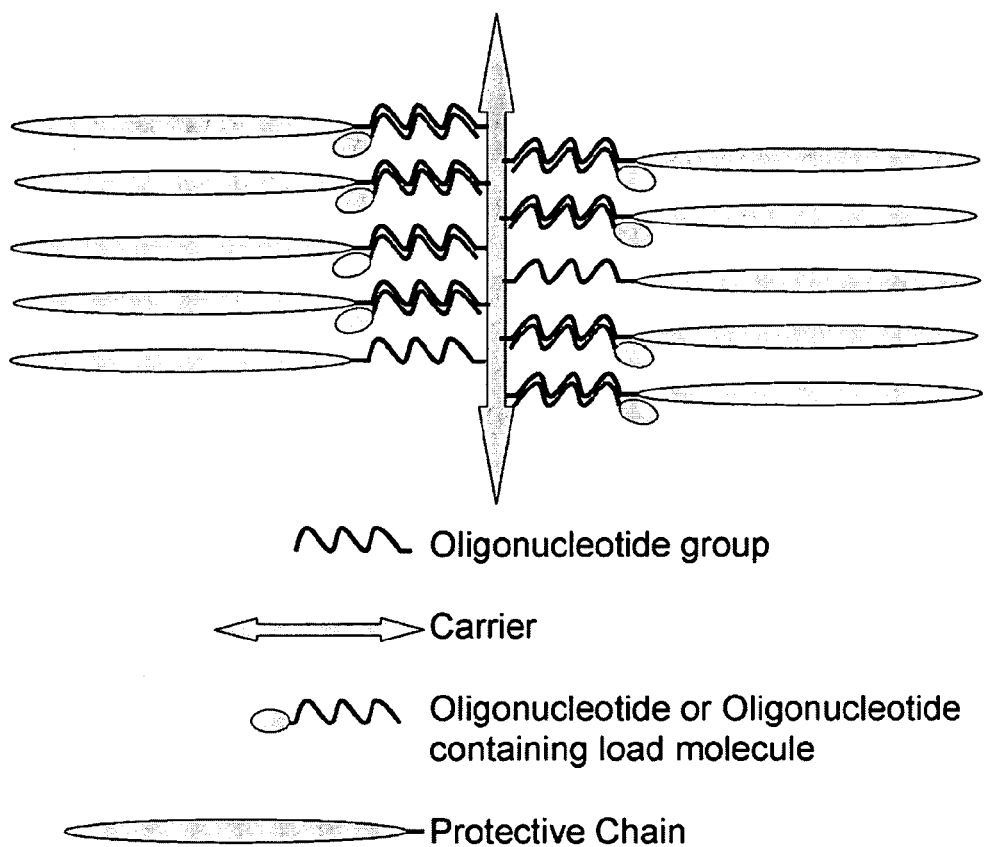

FIG. 19 depicts a diagram of one embodiment of the oligonucleotide-core compositions of the present invention comprising; a carrier, an oligonucleotide group covalently linked to the carrier, a protective chain covalently linked to oligonucleotide group of the carrier, and a load molecule which is either oligonucleotide or oligonucleotide-containing load molecule wherein the load oligonucleotide sequence is essentially complementary to the sequence oligonucleotide linked to the carrier.

Figure 20:
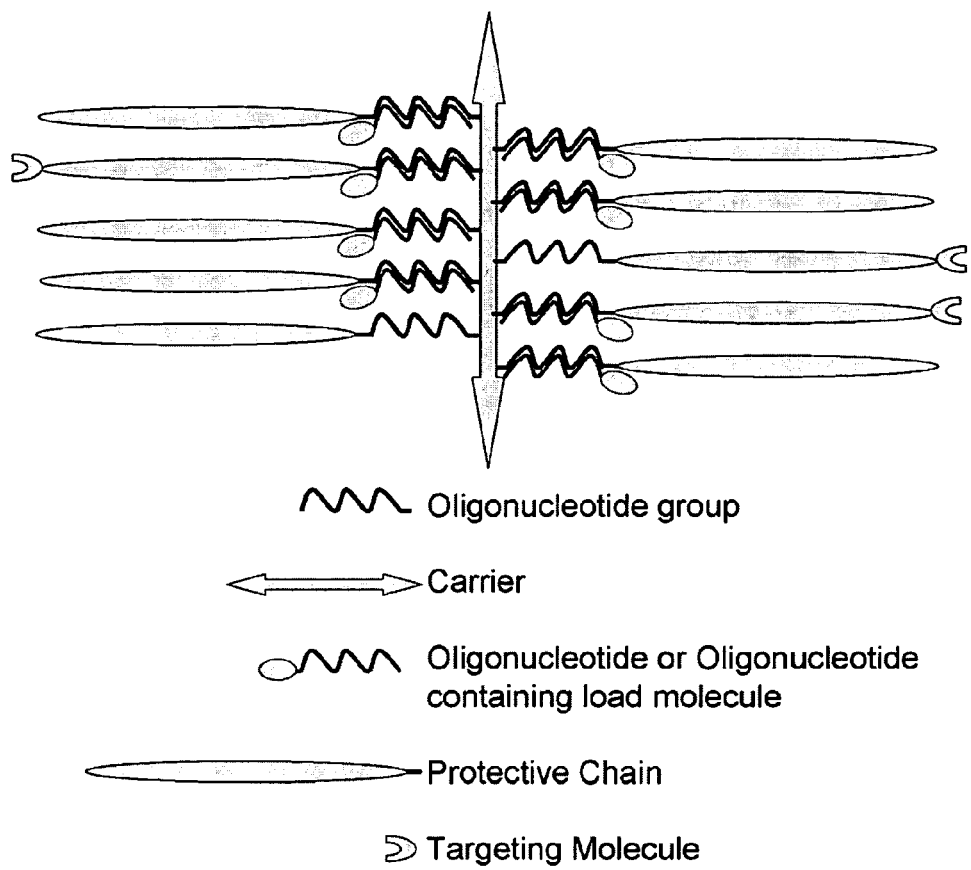

FIG. 20 depicts a diagram of one embodiment of the oligonucleotide-core compositions of the present invention comprising; a carrier, an oligonucleotide group covalently linked to the carrier, a protective chain covalently linked to oligonucleotide group of the carrier, and a targeting moiety covalently linked to the protective chain, and a load molecule which is either oligonucleotide or oligonucleotide-containing load molecule wherein the load oligonucleotide sequence is essentially complementary to the sequence of oligonucleotide linked to the carrier.

DETAILED DESCRIPTION OF THE INVENTION

Definitions

For convenience, before further description of the present invention, certain terms employed in the specification, examples and appended claims are collected here. These definitions should be read in light of the remainder of the disclosure and understood as by a person of skill in the art Unless defined otherwise, all technical and scientific terms used herein have the same meaning as commonly understood by a person of ordinary skill in the art.

The articles "a" and "an" are used to refer to one or to more than one (i.e., to at least one) of the grammatical object of the article. By way of example, "an element" means one element or more than one element.

The term "aminated" as used herein refers to molecules including linked amino groups.

The term "aptamer" means oligonucleic acid or peptide molecules that bind a specific target molecule through specific folding. One of the embodiments of the present invention is to deliver nucleic acid aptamers by providing carrier with oligonucleotide sequence complementary to the nucleic acid aptamer sequence. Aptamers are usually created by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications. RNA and DNA aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers offer the utility for biotechnological and therapeutic applications as they offer molecular recognition properties that rival that of the commonly used biomolecule, antibodies. This is possible through specific folding to create recognition sites. Although this folding can be interrupted by binding to complementary sequence such as that present in the carrier, upon release from the carrier re-folding will occur to provide aptamers that has the right folding to be biologically or therapeutically active. In addition to their discriminate recognition, aptamers offer advantages over antibodies as they can be engineered completely in a test tube, are readily produced by chemical synthesis, possess desirable storage properties, and elicit little or no immunogenicity in therapeutic applications. There is no systematic difference between RNA and DNA aptamers, except for the greater intrinsic chemical stability of DNA. Non-modified aptamers are cleared rapidly from the bloodstream, with a half-life of minutes to hours, mainly due to nuclease degradation and clearance from the body by the kidneys, a result of the aptamer's inherently low molecular weight. Several modifications, such as 2'-fluorine-substituted pyrimidines, polyethylene glycol (PEG) linkage, etc. (both of which are used in Macugen, an FDA-approved aptamer) are available to scientists with which to increase the half-life of aptamers easily to the day or even week time scale. The present invention is designed to deliver unmodified nucleic acid aptamers by providing carrier with oligonucleotide complementary to the nucleic acid. Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). The variable loop length is typically comprised of 10 to 20 amino acids, and the scaffold may be any protein which has good solubility and compacity properties. Currently, the bacterial protein Thioredoxin-A is the most used scaffold protein, the variable loop being inserted within the reducing active site, which is a -Cys-Gly-Pro-Cys-loop in the wild protein, the two Cysteines lateral chains being able to form a disulfide bridge. Peptide aptamer selection can be made using different systems, but the most used is currently the yeast two-hybrid system. Selection of Ligand Regulated Peptide Aptamers (LiRPAs) has been demonstrated. By displaying 7 amino acid peptides from a novel scaffold protein based on the trimeric FKBP-rapamycin-FRB structure, interaction between the randomized peptide and target molecule can be controlled by the small molecule Rapamycin or non-immunosuppressive analogs. These peptide aptamers can be made to contain oligonucleotide sequences complementary to the sequences present in the carrier of the present invention.

The term "carrier" of the present invention may be any substance capable of supporting or covalently linking oligonucleotide groups which in turn can interact by hydrogen bonding to the complementary oligonucleotide group of the load molecule. These are substance with plurality of modifiable functional groups. Non-limiting examples of carriers include polymers, co-polymers, amphipathic molecules, nanoparticles, and microparticles. Microparticle includes particles with diameter of 100 nm or more, whereas nanoparticles are particles with less than 100 nm in diameter. In one aspect, the carrier is biocompatible.

The term "derivative" or "analog" as used herein refers to a compound whose core structure is the same as, or closely resembles that of, a parent compound, but which has a chemical or physical modification, such as a different or additional groups; the term includes co-polymers of parent compounds that can be linked to other atoms or molecules. The term also includes a peptide with at least 50% sequence identity with the parent peptide. The term also includes a peptide with additional groups attached to it, such as oligonucleotides and/or additional amino acids, compared to the parent peptide. The term also includes a polymer with additional group attached to it, such as alkoxy group, compared to the parent polymer. The term also includes methoxylated oligonucleotides with additional methoxy group(s) attached to it compared to the parent oligonucleotide chain. The term also includes hydroxylated oligonucleotides with additional hydroxy group(s) attached to it compared to the parent oligonucleotide chains.

The term "diagnostic" or "diagnostic agent" is any chemical moiety that may be used for diagnosis or imaging a patient and linked to oligonucleotide with sequence complementary to the sequence of the oligonucleotide of the carrier. For example, diagnostic agents include imaging agents containing radioisotopes such as indium or technetium; contrasting agents containing iodine, technetium, or gadolinium; enzymes such as horse radish peroxidase, GFP, alkaline phosphatase, or beta-galactosidase; fluorescent substances such as fluorescein, rhodamine and europium derivatives; luminescent substances such as N-methylacrydium derivatives or the like.

The term "load molecule" as used herein encompasses any molecule containing oligonucleotide with sequence essentially (50-100%) complementary to the oligonucleotide covalently linked to the carrier allowing it to be loaded in to the oligonucleotide-core composition of the present invention. These load molecules included oligonucleotide or oligonucleotide-containing imaging/diagnostic agents and oligonucleotide-containing therapeutic agents, which is designated in the present application as "imaging/diagnostic agent" and "therapeutic agent" respectively.

The term "locked nucleic acid" or LNA, refers to a modified RNA with nucleotide that is inaccessible. Ribose moiety of LNA nucleotide is modified with an extra bridge connecting 2' and 4' carbons. The bridge "locks" the ribose in 3'-endo structural conformation, which is often found in A-form of DNA or RNA. LNA nucleotides can be mixed with DNA or RNA bases in the oligonucleotide whenever desired. Such oligomers are commercially available. The locked ribose conformation enhances base stacking and backbone pre-organization. This increases significantly the thermal stability (melting temperature) of oligonucleotides.

The term "MicroRNA" or "miRNA" are a related class of gene regulatory small RNAs, typically 21-23 nt in length. They typically differ from siRNA because they are processed from single stranded RNA precursors and show only partial complementarity to mRNA targets. They have been implicated in a wide range of functions such as cell growth and apoptosis, development, neuronal plasticity and remodeling, and even insulin secretion. miRNAs have also been implicated in disease: e.g. an overabundance of miRNA has been reported in cases of Fragile X Mental Retardation, while some cancers are associated with up- and downregulation of certain miRNA genes. Initial studies have indicated that miRNAs regulate gene expression post-transcriptionally at the level of translational inhibition at P-bodies in the cytoplasm. However, miRNAs may also guide mRNA cleavage similar to siRNAs. This is often the case in plants where the target sites are typically highly complementary to the miRNA. While target sites in plant mRNAs can be found in the 5'UTR, open-reading frames and 3'UTR, in animals it is the 3' UTR that is the main target. This difference between plants and animals may be explained by their different modes of gene silencing. miRNAs are first transcribed as part of a primary microRNA (pri-miRNA). This is then processed by the Drosha with the help of Pasha/DGCR8 (=Microprocessor complex) into pre-miRNAs. The ~75 nt pre-miRNA is then exported to the cytoplasm by exportin-5, where it is then diced into 21-23 nt siRNA-like molecules by Dicer. In some cases, multiple miRNAs can be found on the pri-miRNA. Some of these miRNA can be used as therapeutic agent.

The term "non-proteinaceous polyamino acid" as used herein refers to a polyaminoacid that is not naturally made by a living organism unless recombinantly engineered by human. Non-limiting examples of these are poly-(L and/or D)-lysine, poly-(L and/or D)-glutamate, poly-(L and/or D)-glutamate, poly-(L and/or D)-aspartate, poly-(L and/or D)-serine, poly-(L and/or D)-threonine, poly-(L and/or D)-tyrosine, and poly-(L and/or D)-arginine. The non-proteinaceous polyamino acid also includes polyamino acids with R-groups that are not naturally occurring but contains carboxyl, amino, hydroxyl, or thiol groups that can provide repeating functional groups that are modifiable for the attachment of protective groups and/or oligonucleotides.

The term "oligonucleotide" means short sequences of nucleotides such as oligoribonucleotides (ribonucleic acid (RNA) or oligodeoxyribonucleotides (deoxyribonucleic acid (DNA), typically with twenty or fewer bases (or nucleotide units) but can be up to up to 160 to 200 bases. Each nucleotide monomer is made up of 3 components covalently linked to each other: a nitrogenous base (purine or pyrimidine), a five-carbon sugar and, a phosphate group. Frequently the term nucleotide unit is also called base because each nucleotide unit has one nitrogenous base. Oligonucleotides can easily be made synthetically and the length of a synthesized oligomer is usually denoted by 'mer' (from 'Greek' meros "part"). For example, a fragment of 25 bases would be called a 25-mer. Oligonucleotides are often used as probes for detecting complementary DNA or RNA because they bind readily to their complements. Oligonucleotides have never been use for the purpose of loading nanocarrier of the present invention, especially in the presence of protective chains. Oligonucleotides are sometimes referred to as oligos. Antisense oligonucleotides are single strands of DNA or RNA that are complementary to a chosen sequence. In the case of antisense RNA they prevent translation of complementary RNA strands by binding to it. Antisense DNA can be used to target a specific, complementary (coding or non-coding) RNA. If binding takes places this DNA/RNA hybrid can be degraded by the enzyme RNase H. Synthesis of oligonucleotide is well known to those skilled in the art and some of these methods are outlined below. Oligonucleotide may comprise of several nucleotides linked together where each nucleotide can be anyone of 2'-deoxyribonucleotide, ribonucleotide, 2'-O-methylribonucleotide, locked ribonucleotide, N-(2-ethylamino) glycine nucleotide and morpholino nucleotide. Each nucleotide can be linked to another by 3'-5' or 2'-5' linkage, wherein the linkage can be phosphodiester, phosphorothio, phosphotriester, phosphorodiamidate and a peptide. The base in each nucleotide of oligonucleotide can be anyone of the typical bases found in nucleic acid such as adenine, thymidine, guanine, cytosine, and uracil or it can also be anyone of the atypical bases such as inosine, thioinosine, thiouridine, xanthosine, pseudouridine, or orotidine The term "oligonucleotide group of the carrier" means oligonucleotide covalently linked or covalently bonded to the carrier.

The term "oligonucleotde group of the therapeutic agent" means the oligonucleotide covalently linked or covalently bonded to the therapeutic agent. Oligonucleotide alone may also be the therapeutic agent.

The term "oligonucleotide group of the imaging/diagnostic agent" means the oligonucleotide covalently linked or covalently bonded to the imaging/diagnostic agent.

The term "polymeric carrier" as used herein refers to a molecule comprised of several repeating and linked chemical units, and serve as sites where oligonucleotides and/or protective chains are linked.

The term "protective side chain" as used herein refers to a molecule(s) which protects a carrier molecule, an oligonucleotide group, and load molecule from contact with other macromolecules due to extensive linking or binding of water to the chains. Because of this extensive binding with water molecules the protective chain also increases water solubility of the composition. This also means that protective chain provides hydrophilic property to the composition. The term "protective side chain" is used interchangeably with the terms "hydrophilic chain", "protective group" and "protective chain."

The term "Small interfering RNA" or "siRNA", sometimes known as short interfering RNA or silencing RNA, are a class of 20-25 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome; the complexity of these pathways is only now being elucidated. SiRNAs have a well defined structure: a short (usually 21-nucleoytide) double-strand of RNA (dsRNA) with 2-nucleotide 3' overhangs on either end: Each strand has a 5' phosphate group and a 3' hydroxyl (—OH) group. This structure is the result of processing by dicer, an enzyme that converts either long dsRNAs or small hairpin RNAs into siRNAs (Bernstein et. al. 2001 Nature 409 (6818): 363-6). SiRNAs can also be exogenously (artificially) introduced into cells by various transfection methods to bring about the specific knockdown of a gene of interest. Essentially any gene of which the sequence is known can thus be targeted based on sequence complementarity with an appropriately tailored siRNA. This has made siRNAs an important tool for gene function and drug target validation studies in the post-genomic era. Transfection of an exogenous siRNA can be problematic, since the gene knockdown effect is only transient, particularly in rapidly dividing cells. The present invention is designed to overcome this and satisfy the long felt need to provide a sustained inhibition that remains non-permanent.

The term "Spacer" refers to a covalently linked chain of atoms that provide space of 3 Angstroms to 50 Angstroms, inclusive, between the oligonucleotide and the carrier or the oligonucleotide and the protective group or chains. Before incorporation of the spacer the terminals of the spacer will have a chemically reactive group that facilitate covalent attachment to any one of oligonucleotide, carrier, or protective chains. Example of spacer is one that incorporates to the terminal phosphate group of the oligonucleotide at one end by phosphoester linkage (a linkage well known in the art and can be done by those skilled in the art) and has amino group at the other end that can be attached to the carrier or a protective chain. The distance between the phoshoester link and the amino group can be flanked by alkyl group, preferably linear, containing 3 to 50 carbon atoms. This flanking group is not limited to alkyl group but can also be polyethylene glycol chain containing 2 to 25 ethylene units or derivative thereof. There type linkers can have variable length for use in different applications but generally to provide aminogroup and sometimes called aminolinks. Aminolinks can be coupled to both the 5'- and the 3'-end of the oligonucleotide. Modifications at the 3'-terminus of oligonucleotides make them more resistant against exonuclease digestion. Furthermore, it can be useful to link an aminogroup inside the oligonucleotide. For this purpose, a thymidine nucleotide's C5 methyl group can be easily replaced by a C6 linker with an amino group at its end. Thus the interaction between the amino group and the DNA is reduced as far as possible so that the modified oligonucleotide behaves in hybridisation comparable to a respective unmodified one. The linker can also be similar to the above aminolink except that instead of amino group at one end it contains carboxyl group which can easily be activated or already activated (either by NHS (N-hydroxy succinimidyl) or sulfo NHSS (N-hydroxy-sulfosuccinimidyl) to attached to amino group of the carrier or protective chain. The linker can also be similar to aminolink except that instead of amino group at one end it contains thiol group which can easily be attached to the carrier or protective chain.

The term "targeting moiety," "targeting molecules," or "targeting group" refers to any molecular structure which assists the construct of the composition in localizing at a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, peptides, and proteins may serve as targeting moieties.

A "target" is a site to which targeted constructs or the oligonucleotide core compositions bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatibs) and pathogenic fungi (*Candida sp.*). In still other embodiments, a target may refer to a molecular structure to which a targeting moiety binds, such as a hapten epitope, receptor, dsDNA fragment, carbohydrate or enzyme. Additionally, a target may be a type of tissue, e.g., neuronal tissue, intestinal tissue, pancreatic tissue etc.

The term "therapeutic agents" as used herein refer to any chemical moiety that is a biologically, physiologically, or pharmacologically active and act locally or systemically in a subject. For the purpose of the present invention, therapeutic agent loaded into the carrier is understood to be oligonucleotide or have oligonucleotide group modification. Examples of therapeutic agents (also referred to as "drugs") in which oligonucleotides may be linked to facilitate loading into oligonucleotide-core carrier of the present invention, are glucagon-like-peptide, glucagon-like-peptide derivatives, exenatide, glucagon-like-peptide-1, glucagon-like-peptide-2, leptin fragment, Gastric inhibitory polypeptide(GIP), Epidermal Growth Factor (EGF) receptor ligand, EGF, Transforming Growth Factor alpha (TGF-alpha), Betacellulin, Gastrin/Cholecystokinin receptor ligand, Gastrin, Cholecystokinin, lysostaphin, interferon, interferon gamma, interferon beta, interferon alpha, interleukin-1, interleukin-2, interleukin-4, interleukin-6, interleukin-8, interleukin-10, interleukin-12, auristafin, nisin, insulin, insulin-like growth factor 1, growth hormone, growth hormone releasing hormone (GHRH), nerve growth factor, brain-derived neurotrophic factor, enzymes, endostatin, angiostatin, trombospondin, urokinase, streptokinase, blood clotting factor VII, blood clotting factor VIII, granulucyte-macrophage colony-stimulating factor (GM-CSF), granulucyte colony-stimulating factor (G-CSF), thrombopoetin, calcitonin, parathyroid hormone (PTH) and its fragments, erythropoietin, atrial natriuretic factor, monoclonal antibodies, monoclonal antibody fragments, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastin, prostaglandins, epoprostenol, prostacyclin, cyclosporine, vasopressin, terlipressin, desmopressin, cromolyn sodium (sodium or disodium chromoglycate), vasoactive intestinal peptide (VIP), vancomycin, antimicrobials, polymyxin b, anti-fungal agents, anti-viral agents, enfuvirtide, doxorubicin, etoposide, fentanyl, ketamine, and vitamins. Oligonucleotide with sequence complementary to the oligonucleotide sequence in the carrier may be attached to the above therapeutic agents to facilitate loading into the carrier. The oligonucleotide attached to the therapeutic agent can be RNA or DNA or their analogs. It is preferable to attach RNA as anchoring agent as once released from protective carrier, RNA will rapidly be removed by endogenous RNAses leaving the native unaltered therapeutic agent. In most cases, the therapeutic agents are natural peptides that are non-immunogenic but are susceptible to breakdown and elimination without the protection of the carrier. Altering them to contain RNA as anchoring agent is ideal as when the anchoring function is fulfilled, RNA is rapidly removed to give a native non-immunogenic therapeutic agent.

Further examples of therapeutic agents in which oligonucleotide groups can be linked, also referred to as "drugs", are described in well-known literature references such as the Merck Index, the Merck manual of diagnosis and therapy, the Physicians Desk Reference, and The Pharmacological Basis of Therapeutics, and they include, without limitation, proteins, peptides, medicaments; vitamins; mineral supplements; substances used for the treatment, prevention, diagnosis, cure or mitigation of a disease or illness; substances which affect the structure or function of the body; or prodrugs, which become biologically active or more active after they have been placed in a physiological environment. Various forms of a therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplabn), hormone antagonists (e.g., tamoxifen), non-specific (non-antibody) proteins (e.g., sugar oligomers), peptides, proteins, antibodies, photodynamic agents (e.g., rhodamine 123), radionuclides (e.g., 1-131, Re-186, Re-188, Y-90, Bi-212, At-211, Sr-89, Ho-166, Sm-153, Cu-67 and Cu-64), toxins (e.g., ricin) will require mode of attachment to oligonucleotide-core. Therapeutic agents also include oligonucleotides that do not need further modifications to complement to the oligonucleotide core of the carrier such as antisense oligonucleotides, aptamers, and siRNA that bind to a target nucleic acid sequence (e.g., mRNA sequence)) and siRNA.

The term "therapeutically effective amount" as used herein refers to the amount of composition that will provide a therapeutic benefit to the patient. In certain embodiments, the term refers to an amount of the therapeutic agent that, when loaded to the oligonucleotide-core carrier composition of the present invention and administered to the patient, produces some desired effect at a reasonable benefit/risk ratio applicable to any medical treatment. In certain embodiments, the term refers to that amount necessary or sufficient to eliminate, reduce or maintain (e.g., prevent the spread on a tumor or other target of a particular therapeutic regimen. The effective amount may vary depending on such factors as the disease or condition being treated, the particular constructs being administered, the size of the subject and/or the severity of the disease or condition. One of ordinary skill in the art may empirically determine the therapeutically effective amount of a particular compound without necessitating undue experimentation. In certain embodiments, the term refers to that amount necessary or sufficient for a use of the subject compositions described herein. In the treatment of obesity, the therapeutically effective amount is the amount of composition of the present invention with corresponding load molecule(s) such as, but not limited to, anti-ghrelin siRNA that will reduce ghrelin, appetite, and weight. In the treatment of obesity, the therapeutically effective amount is the amount of composition of the present invention with corresponding load molecule(s) such as, but not limited to, anti-NeuropeptideY (NPY) siRNA that will reduce NPY, appetite, and weight. In the treatment of obesity, the therapeutically effective amount is the amount of composition of the present invention with corresponding load molecule(s) such as, but not limited to, RNA-oligonucleotidelinked leptin that will increase leptin, decrease appetite and weight. In the treatment of obesity, the therapeutically effective amount is the amount of composition of the present invention with corresponding load molecule(s) such as, but not limited to, RNA-oligonucleotide-linked PYY that will increase PYY, decrease appetite and weight. In the treatment of insulin-insufficient diabetes, the therapeutically effective amount is the amount of composition of the present invention with corresponding load molecule(s) that will improve glucose homeostasis or normalize blood glucose level of the patient and/or regenerate the beta-islet cells in the pancreas. The regeneration of the beta-islet cells the can be indirectly measured by monitoring blood glucose level, Hemoglobin Alc level, C-peptide level, or insulin level in the blood.

Introduction

In part, the present invention relates to a composition comprising (i) a carrier, (ii) oligonucleotide groups covalently attached to the carrier, (iii) protective side chains covalently attached to the carrier or oligonucleotide groups, and (iv) a load molecule bound to the oligonucleotide group of the carrier. By way of a further embodiment, the carrier may optionally contain a targeting molecule covalently attached to the protective side chains.

The carrier compositions of the present invention include polymers and co-polymers of linear or branched structure or conjugates, where the polymer(s) may self organize in supra molecular structures. The carrier composition also includes amphipathic molecules, micelles, liposomes, and emulsions. One of the functional compositions of the present invention includes a polymeric backbone comprising covalently bound oligonucleotide groups where the groups comprise DNA or RNA. The oligonucleotide portion of the carrier and the oligonucleotide portion of the load molecules interact with each other to form hydrogen bonds in aqueous or predominantly aqueous media such as biological fluids. It may be the case that the oligonucleotide groups comprise more than one kind of DNA-oligomer and/or RNA-oligomer covalently attached to the carrier. It may also be the case that the protective groups re-enforce the binding of oligonucleotide-containing load molecules to the carrier containing complementary oligonucleotide groups. The oligonucleotide-containing load molecules bind to the complementary oligonucleotide groups in the carrier in the presence or absence of organic solvents. In one the preferred embodiments the oligonucleotide moiety comprises DNA chains such as, but not limited to, antisense DNA of 2-100 mer. Heat, high aqueous salt solution, chaotrophic solvent can be used to elute or extract oligonucleotides from oligonucleotide-core carrier. Higher amounts of salts or chaotrophic solvents (such as guanidine or urea) required to elute load molecules from the carrier is an indication of tight binding. Binding of load molecule to oligonucleotide carrier means the ability to be retained by the carrier after washing with at least 100 fold weight equivalent of aqueous solvent. If a carrier with strong binding to the load molecule is desired, longer oligonucleotide groups and more of them may be used to modify the carrier and load molecule. Tighter binding can also be achieved by using G:C (Guanine: Cytosine) rich sequences to anchor the therapeutic agent. The high affinity binding of oligonucleotide containing load molecules to the carrier comprising oligonucleotide groups will maintain low level of free load molecules (i.e. drugs or therapeutic agents) at any given time, and provide a protected reservoir of oligonucleotide containing load molecule (i.e. carrier bound oligonucleotide-containing load molecule will be a reservoir). This will reduce the frequency of administration of the therapeutic agent This is also beneficial for therapeutic agents that require low concentrations to have therapeutic effects and at the same time are toxic at high concentrations. The invention also provides a method of making and using an oligonucleotide-core carrier for specific therapeutic compounds.

In one example, a composition of the present invention comprises a linear polyamino acid backbone carrier having a degree of polymerization in the range of 2-10,000 to which are covalently linked methoxypolyethyleneglycol (mPEG) protective chains with a mass of 300-20,000 Da, and oligonucleotide groups, wherein the chains and oligonucleotide groups are independently linked to the backbone. In another example, the degree of polymerization of the carrier is in the range of 20-1,000. In still another example, the degree of polymerization of the carrier is in the range of 50 to 300. The oligonucleotide groups of the present invention may include RNA and DNA that may also contain methoxy modification or other tags (fluorophore or chromophore) which may be in the 3'-terminal, 5'-terminal, or in the internal bases. These oligonucleotide-core carrier-protective group compositions will bind load molecules with complementary oligonucleotide. Oligonucleotide such as siRNA or oligonucleotide-containing load molecules added in a purified state will bind to the oligonucleotide portion of the carrier without and in most cases with facilitation by heating (between 60-100° C.) and upon cooling will provide a drug formulation ready for administration, lyophilization and packaging, or packaging. This addition or mixing of the oligonucleotide-core carrier-protective group complexes with the oligonucleotide or oligonucleotide-containing load molecules can be performed in heated aqueous solution and optionally followed by lyophilization. The dried mixture can be turned into ready formulation by dissolving in water, buffer, or pharmaceutically acceptable diluents or excipient for administration. Once in the blood or any biological fluid, the oligonucleotide-containing load molecules in the composition will be released based on equilibrium association- or dissociation-constants of the oligonucleotide load molecules and the oligonucleotide-core carrier. The concentration of free load molecule will be maintained as long as there is reservoir of load molecules in the carrier. The expected acceleration of release by blood proteins will be tempered quite significantly by protective groups. In addition the release of oligonucleotide or oligonucleotide-containing load molecules from the oligonucleotide-core carrier can be slow or fast depending on the number and length of interacting oligonucleotide moieties in the carrier.

The association of oligonucleotide in the load molecules with the oligonucleotide groups in the carrier is controlled by the number of interacting bases and the composition of the interacting bases. G:C (Guanine:Cytosine) rich oligonucleotides will interact stronger than the A:T (Adenine:Thymine) rich oligonucleotides of the same lengths. In general, the longer the oligonucleotide chains up to 15, the stronger the association. In addition, the higher the number of mismatch in complementarity the weaker the association. The affinity of the load molecule for the target receptors on the cells can also be used as a guide for the choice of length and composition of oligonucleotide groups. Ideally the affinity of the load molecule for the oligonucleotide group in the carrier should be lower than the affinity of the load molecule for its biological target. In solution, there will be equilibrium between free load molecules and bound load molecules. The carrier with oligonucleotide groups will be designed along with the oligonucleotide attached to the load molecule such that the free oligonucleotide-containing load molecules equal to the desired therapeutic concentrations.

The oligonucleotide-core carrier provides drug delivery system that allows significant increase in stability, solubility and distribution of the active molecule.

The oligonucleotide-core carrier composition may further include covalently attached targeting molecules to facilitate localization of the carrier to the target tissues and organs and cells in vitro and in vivo. Additionally, the oligonucleotide-core carrier composition containing load molecules can further comprise a semi-permeable membrane enclosing the entire oligonucleotide carrier composition containing load molecules for sub-dermal or oral administration. The semi-permeable membrane may be made up of polymer sheet with pores of sufficient size to allow the load molecule to cross the semi-permeable membrane. Another object of the present invention is to provide a method of making and using the same for the treatment of various diseases.

Carrier

The carrier of the present invention may be any substance capable of supporting oligonucleotide groups which in turn can interact with the load molecule with covalently linked oligonucleotide that is complementary in sequence with the oligonucleotide of the carrier. The carrier of the present invention must have a plurality of derivatisable or modifiable functional groups for the attachment of oligonucleotide groups and/or protective chains. Non-limiting examples of carriers include polymers, co-polymers, nanoparticles, and amphipathic molecules that on occasion form micelles, liposomes, and gels. In one aspect, the carrier is biocompatible.

In certain embodiments, the polymeric or co-polymeric carriers of the subject compositions, e.g., which include repetitive elements shown in any of the subject formulas, have molecular weights ranging from about 500 to about 1,000,000 or more Daltons, or preferably about 5,000; 10,000; 20,000; 30,000; 40,000; or 50,000 Daltons. On rare occasion at least about 100,000 Daltons will be needed. At least about 250,000 Daltons or even at least 500,000 Daltons may also be used. Number-average molecular weight (Mw) may also vary widely, but generally fall in the range of about 500 to about 200,000 Daltons, or even from about 500 to about 100,000 Daltons or even from about 500 to about 50,000 Daltons. In one embodiment, Mw varies between about 8,000 and 45,000 Daltons. Within a given sample of a subject polymer, a wide range of molecular weights may be present. For example, molecules within the sample may have molecular weights which differ by a factor of 2, 5, 10, 20, 50, 100, or more, or which differ from the average molecular weight by a factor of 2, 5, 10, 20, 50, 100, or more.

One method to determine molecular weight is by gel permeation chromatography ("GPC") also known as gel filtration chromatography ("GFC"), e.g., mixed bed columns, $CH_2Cl_2$ solvent, light scattering detector, and offline dn/dc. Other methods are known in the art.

In certain embodiments, the intrinsic viscosities of the polymers generally vary from about 0.01 to about 2.0 dL/g in chloroform at 40° C., alternatively from about 0.01 to about 1.0 dL/g and, occasionally, from about 0.01 to about 0.5 dL/g.

In one embodiment, the carrier may be composed of polyamino acids, preferably non-proteinaceous polyamino acids, polyethyleneimines, polyallyamine, chitosan, natural saccharides, aminated and carboxylated polysaccharides, aminated and carboxylated oligosaccharides, sulfonated polysaccharides, sulfonated oligosaccharides, aminocarboxylated polysaccharides, aminocarboxylated oligosaccharides, carboxymethylated polysaccharides, carboxymethylated oligosaccharides, polyamidoamine, polyacrylic acids, polyalcohols, polyvinyl alcohol, and polythiols. All these carrier polymers have amino, carboxyl, hydroxyl, sulfonate or thiol groups that can be used to attach oligonucleotide groups or protective groups essentially altering their properties and allowing them to be both soluble and specific oligonucleotide binder at the same time.

The carrier may be composed of polymers comprising modifiable functional groups such as, but not limited to polybases, polyalcohols, or polyacids e.g. polylysine, polyserine, polythreonine, polyglycerol, polytyrosine, polyaspartic or polyglutamic acid, or carboxylated polylysine. These reactive or charged functional groups along the backbone are useful since they are capable of forming chemical bonds with the protective- or oligonucleotide-groups or derivatives or analogs thereof.

The polyamino acid may be a polymer of a single species, or at least two different species of amino acid, or may be a block co-polymer. The polyamino acid may include but not limited to polyaminoacid fragments linked by cleavable bonds, e.g., S—S bonds. In particular, the polyamino acid may be poly-(L and/or D)-lysine, poly-(L and/or D)-glutamate, poly-(L and/or D)-glutamate, poly-(L and/or D)-aspartate, poly-(L and/or D)-serine, poly-(L and/or D)-threonine, poly-(L and/or D)-tyrosine, poly-(L and/or D)-arginine, or poly-alpha,beta-(2-aminoethyl)-(L and/or D)-aspartamide. All of these polymers have amino, carboxyl, hydroxyl, or thiol groups that can be used to attach oligonucleotide groups, or protective groups allowing them to be both soluble and specific oligonucleotide binder at the same time. The polyamino acid carrier of the oligonucleotide-core composition preferably has 5-560 amino acid units, a molecular weight of 500-100,000 Daltons, and is preferably non-proteinaceous.

Examples of aminated polysaccharide or oligosaccharides carrier include but are not limited to polyglucosamine (chitosan), and polygalactosamine.

Examples of carboxylated polysaccharide or oligosaccharides carrier include but are not limited to of polyglucuronic acid and polygalacturonic acid.

Further examples of polymeric carriers include carboxylated or carboxymethylated linear poly-L-lysine (PL) or poly-D-lysine; carboxylated or carboxymethylated polyalpha,beta-(2-aminoethyl)-D,L-aspartamide; poly-L-aspartic acid; poly-L-glutamic acid, copolymers of histidine with positively or negatively charged amino acids, carboxylated polyethyleneimines, i.e. polyethylene imines reacted with derivatives of carbonic acids; natural saccharides or products chemically derived thereof, bearing carboxylic groups, which may be exemplified by: galacturonic acid, glucuronic acid, mannuronic acid, hyaluronic acid, pectic acid, neuraminic acid, alginic acid, carrageenan; oxidized dextrans; aminated, e.g. containing linked amino groups, polysaccharides or oligosaccharides, linear or branched; polycarboxylated, carboxymethylated, sulfated or phosphorylated polysaccharides or oligosaccharides, e.g. reacted with derivatives of carbonic, dicarbonic, sulfuric, amino sulfuric, phosphoric acids with resultant linking of carboxylic, amino carboxylic, carboxymethyl, sulfuric, amino or phosphate groups. Such oligosaccharides may be obtained by chemical alteration of, e.g., dextran, mannan, xylan, pullulan, cellulose, chitosan, agarose, fucoidan, galactan, arabinan, fructan, tan, fucan, chitin, pustulan, levan or pectin. In addition these poly- or oligosaccharides may be represented by heteropolymers or homopolymers of monosaccharides such as glucose, galactose, mannose, galactose, deoxyglucose, ribose, deoxyribose, arabinose, fucose, xylose, xylulose, ribulose, polyamidoamine, linear or branched; polyacrylic acid; polyalcohols, e.g. polyvinyl alcohol an polyxylitol, to which carboxylic or amino groups are chemically linked. The molecular weight of a polyaminoacid is preferably larger than 500 and smaller than 100,000. Polyamino acids with narrow molecular weight (MW) distribution are preferred to those with broad MW distribution. Polyaminoacids are prepared by chemical synthesis or by recombinant techniques, such as genetic engineering.

In another embodiment, the polymer acting as the carrier may be poly(ethylene glycol) (PEG) with oligonucleotide groups at the far-end making up the site to which the oligonucleotide-tagged load molecule or the active agent binds. Schematically the embodiment may be represented by the following: PEG-oligonucleotide group-load molecule. Alternatively, PEG may be functionalized along its backbone allowing oligonucleotide moieties to be pendant to the backbone that would allow binding of oligonucleotide-containing load molecule with the pendant complementary oligonucleotide moieties. This functionalization may also allow pendant protective chains as well.

In another embodiment, the polymer acting as the carrier may be polyglycerol with poly(ethylene glycol) of the formula HO-PEG-[-$CH_2CH(OH)CH_2O$-]$_n$-PEG-OH where PEG represents poly(ethylene glycol) and n is an integer from 2 to 1000.

For additional examples of polymers suitable for use in the present invention see U.S. Pat. Nos. 6,509,323; 6,492,560; 6,468,532; 6,521,736; 6,348,069; 5,871,710; and 6,051,549 incorporated herein by reference.

In another embodiment, bulk eroding polymers such as those based on polyesters including poly(hydroxy acids) can be used. For example, polyglycolic acid ("PGA") or polylactic acid ("PLA") or copolymers thereof may be used, wherein the polyester has incorporated therein a charged or functionalizable or modifiable group such as an amino acid as described below. This functionalizable group can be modified to contain oligonucleotide groups capable of binding specific oligonucleotide-containing load molecules.

The use of the poly(lactic acid) copolymer, and polylysine is advantageous since it biodegrades into lactic acid and lysine, which can be processed by the body.

Oligonucleotides and Their Synthesis

Oligonucleotides are short sequences of nucleotides such as ribonucleic acid (RNA) or deoxyribonucleic acid (DNA), typically with twenty or fewer bases but can be up to up to 160 to 200 bases. These can easily be made synthetically and the length of a synthesized base is usually denoted by 'mer' (from 'Greek' meros "part"). Oligonucleotides are chemically synthesized using nucleotides, called phosphoramidites, normal nucleotides which have protection groups added to its reactive amine, hydroxyl and phosphate groups. These protection groups prevent unwanted side reactions and force the formation of the wanted product during synthesis. One phosphoramidite is added at the time, the product's 5' phosphate is deprotected and a new base is added and so on (backwards), at the end, all the protection groups are removed. Nevertheless, being a chemical process, several incorrect reactions may lead to some defective products. The longer the oligonucleotide sequence that is being synthesized, the more defects there are, thus this process is only efficient and accurate for producing short sequences of nucleotides which is ideal source of for the purpose of enablement of the present invention. HPLC can be used to isolate products with the proper sequence.

In solid-phase synthesis, the 3' end of the oligonucleotide is bound to a solid support column on which all reactions take place. The 3' group of the first base is immobilized via a linker onto a solid support (polystyrene beads, controlled pore glass beads (CPG), or similar). This allows for easy addition and removal of reactants. In each step, the solutions with the nucleotides for the next reaction are pumped through the column from an attached reagent delivery system and washed out before the next nucleotide is added. In modern synthesizers, reagent delivery and washing steps are controlled via computer based on the wanted sequence. At the end of the synthesis program, the oligonucleotide is cleaved off the solid support and eluted from the column. Essentially, oligonucleotide synthesis is done via a cycle of four chemical reactions that are repeated until all desired bases have been added: Step 1—De-blocking (detritylation): The dimethoxttrityl (DMT) is removed from 5' hydroxy with an acid, such as trichloroacetic acid (TCA), and washed out, resulting in a free 5' hydroxyl group on the first base. Step 2—Base condensation (coupling): A phosphoramidite nucleotide (or a mix) is activated by tetrazole which removes the iPr2N group on the phosphate group. After addition, the deprotected 5' OH of the first base and the phosphate of the second base react to join the two bases together in a phosphite linkage. These reactions are not done in water but in tetrahydrofuran or in DMSO. Unbound base and by-products are washed out. Step 3—Capping: About 1% of the 5' OH groups do not react with the new base and need to be blocked from further reaction to prevent the synthesis of oligonucleotides with an internal base deletion. This is done by adding a protective group in the form of acetic anhydride and 1-methylimidazole which react with the free 5' OH groups via acetylation. Excess reagents are washed out. Step 4—Oxidation: The phosphite linkage between the first and second base needs to be stabilized by making the phosphate group pentavalent. This is achieved by adding iodine and water which leads to the oxidation of the phosphite into phosphate. This step can be substituted with a sulphorylation step for thiophosphate nucleotides. After synthesis is complete, the oligonucleotides are cleaved off the column and deprotected (base and phosphate) by base hydrolysis using ammonium hydroxide at high temperature. This removes all remaining protection groups, resulting in a reaction mixture containing the wanted product. For some applications, additional reporter groups are added post-synthesis. The oligonucleotide can be purified further from this mix by desalting through ethanol precipitation, size exclusion chromatography, or reversed-phase chromatography. To eliminate unwanted truncation products, the oligonucleotides can be purified via polyacrylamide electrophoresis or HPLC.

To obtain terminally modified oligonucleotides, the last 5' nucleotide introduced during solid phase synthesis is modified in such a way to contain amino, carboxyl, or thiol groups. A primary amine can be used to covalently attach oligonucleotide to a variety of chemicals including fluorescent dyes (Connolly and Rider, 1985 Nucleic Acids Res. 13:4485-

4502; Zuckerman et al., 1987 Nucleic Acids Res. 14:5305-5321), biotin (Sproat et al, 1987 Nucleic Acids Res. 15:4837-4848), alkaline phosphatase (Li et al., 1987 Nucleic Acids Res. 15:5275-5287), or EDTA (Dreyer and Dervan 1985 Proc. Natl. Acad. Sci. USA 82:968-972) and attachment to the carrier in the present invention is no different. An amino modifier can be place at the 5'-end, 3'-end or internally using and amino-dC or amino-dT modified base.

5' Amino Modifiers

Various amino-modifiers can be added to the 5'-terminus of a target oligonucleotide. Because conventional automated synthesis proceeds from 3' to 5', addition of the 5'-amino-modifiers is the last step in synthesis. As a result, truncated "capped" failure products will not receive the 5'-amino-modification and will not participate in subsequent chemical reactions involving the primary amine. 5' amino modifiers are β-cyanoethyl phosphoramidites which, when activate with 1H tetrazole, can couple to the 5' terminus of the oligonucleotide in the same time frame and with similar efficiency as nucleoside phosphoramidites. A number of 5' amino modifiers are available from IDT (Coralville, Iowa), these include simple amino groups with a six or twelve carbon spacers, a Uni-Link Amino modifier or amino modified thymidine or cytosine. The shorter carbon chain linkers (Amino C6 and Uni-Link) may be used to attach compounds where proximity to the oligonucleotide poses no problem. The longer carbon chain linker (Amino C12) is recommended to avoid steric or charge hindrance. Sometimes even greater distance is needed than is offered by the amino-C12 modifier. In this case, one or more internal spacer modifiers (such as the S18 spacer) can be used to further separate the 5'-terminal amino-modifier from the oligo.

3' Amino Modifiers

3'-amino-modifiers contain branched linkers in which the amino group is protected with the fluorenylmethoxycarbonyl (Fmoc) group which was originally popularized for use in peptide chemistry (Nelson et al., 1989 Nucleic Acids Res. 17:7179-7186, 1992 Nucleic Acids Res. 20:6253-6259). The Fmoc group is stable yet can be removed specifically from the support to allow solid-phase addition of an amino linked modification. However, during handling some Fmoc groups can be lost; in this setting the free amino group is capped with acetic anhydride during synthesis and results in decreased yields. 3'-Amino-Modifier CPG otherwise supports oligo synthesis with the same efficiency as a standard nucleoside CPG. After deprotection, the finished oligonucleotide has a free primary amine at the 3'-terminus. An oligo with a 3'-amino-modification can be labeled at the 5'-end to the carboxyl containing carrier. Alternatively, the oligo can be left with a free 5'-OH, which can later be labeled with 32P using polynucleotide kinase. The 3'-amino-modifier eliminates the native 3'-OH group from the oligo, which functionally blocks this oligo from participating as a primer in DNA synthesis, sequencing, or PCR. Internal Amino Modification Amino-modifier C6 dT and the recently introduced amino-modifier C6 dC are available for internal labeling. Addition of the amino-modifier itself does not adversely affect oligo hybridization characteristics, however subsequent addition of a carrier can potentially lower Tm or interfere with primer function. It is therefore preferable to attach large bulky groups to the 5'-end of the oligo, separated by spacers as needed. Amino-modifier dT and dC couple with similar efficiency as normal phosphoramidite monomers and their trifluoroacetyl-protecting group is removed during the standard ammonium hydroxide deprotection step.

5' Thiol Modifier and 3' Thiol Modifier

The incorporation of a thiol group at the 5' end of an oligo is achieved with S-trityl-6-mercaptohexyl derivatives (Connolly and Rider, 1985 Nucleic Acids Res. 13:4485-4502; Sinha and Cook 1988 Nucleic Acids Res. 16:2659-2669). It is recommended to purify thiol-modified oligonucleotides by HPLC.

The 3'-thiol modifier C3 S—S CPG is used to introduce a thiol group to the 3'-terminus of a target oligonucleotide. A 3' thiol group can be particularly useful for post synthesis modification in cases where a second 5' modification is already in place. Special precautions are taken during the oxidation steps of the synthesis to avoid oxidative cleavage of the disulfide linkage. Deprotection with a cocktail containing DTT is used to remove the base protecting groups and cleave the disulfide linkage to generate the reactive 3'-thiol. Oligos stored disulfide form spontaneously cleavage to some variable fraction of the molecules. This is normal and disulfide dimers will accumulate over time. All thiol-oligos need to be reduced in preparation prior to conjugation with the carrier, load molecules or protective groups immediately before use.

5' carboxyl Modifier and 3' carboxyl Modifier

Addition of carboxyl functionality to the 5' of oligonucleotide can be accomplish by activating the phosphate group at pH of around 6 using carbodiimide such as EDC which can then be reacted to amino group or hydroxyl group of hetero bifunctional reagent with one end protected such as amino caproic acid or 8-hydryxy caproic. Addition of carboxyl functionality to the 3' of oligonucleotide can be accomplished by using a modified attachment to the solid phase resin during synthesis where the first nucleotide is attached to the resin using a cleavable spacer that will have free carboxyl group once clipped or will have a functional group that can easily be activated to react with a spacer that will give free carboxyl once attached.

The descriptions above outlining various ways to prepare nucleotides for use in the present invention are by no means limiting the scope of the invention. It is understood that other functional groups can be introduced to oligonucleotides at sites that includes the internal bases by those skilled in the art. Such modification can be tailored in such a way that will facilitate covalent attachment of the oligonucleotide to the carrier, load molecules and protective chains of the present invention without altering the ability of oligonucleotide to base pair or hydrogen bond with its complementary oligonucleotide. The modification can be design to attach functional groups useful for attaching oligonucleotide to the carrier or protective chains of the present invention. The functional groups that can be used include activated or non-activated carboxyl groups, amino groups, thiol groups activated or non-activated hydroxyl groups.

The 1-ethyl-3-(3'-dimethylaminopropyl)carbodiimide (EDC)-induced modification of the carboxyl group in a synthetic oligodeoxyribonucleotide is quite efficient. Treatment of a carboxyl-containing oligonucleotide with EDC in water or aqueous buffer solutions leads to the rapid formation (with an 80-90% yield) of the corresponding ureido derivabve, which can easily be isolated by PAGE. These derivatives are stable in neutral and weakly acid aqueous solutions, whereas under weakly basic conditions they efficiently (50-90%) acylate amino groups. Reagents of this type can be used for modification of amino containing carrier or load molecules such as proteins and peptide drugs.

Amino Modified Oligonucleotides and Chemistry of Attachment

Attaching an amino modified oligonucleotide to a carrier, protective groups, or load molecules requires an acylating reagent that forms carboxamides, sulfonamides, ureas or thioureas upon reaction with the amine moiety. The kinetics of the reaction depends on the reactivity and concentration of both the acylating reagent and the amine. Buffers that contain free amines such as Tris and glycine must be avoided when using any amine-reactive reagent. The most significant factors affecting an amine's reactivity are its class and its basicity. Oligonucleotides with an amino modification have a free aliphatic amine that is moderately basic and reactive with most acylating reagents (activated carboxyl groups of polyglutamic or polyaspartic acid are examples). However, the concentration of the free base form of aliphatic amines below pH 8 is very low; thus, the kinetics of acylation reactions of amines by isothiocyanates, succinimidyl esters and other reagents are strongly pH dependent. A pH of 7.3-9.5 is usually optimal for oligonucleotide conjugation into materials with activated carboxyl groups. Aromatic amines, present within each base, are very weak bases and thus are not protonated at pH 7 or above. Most attachment chemistries currently in use for amino modified oligonucleotides utilize a carbodiimide mediated acylation as illustrated in FIG. 2.

Figure 2:
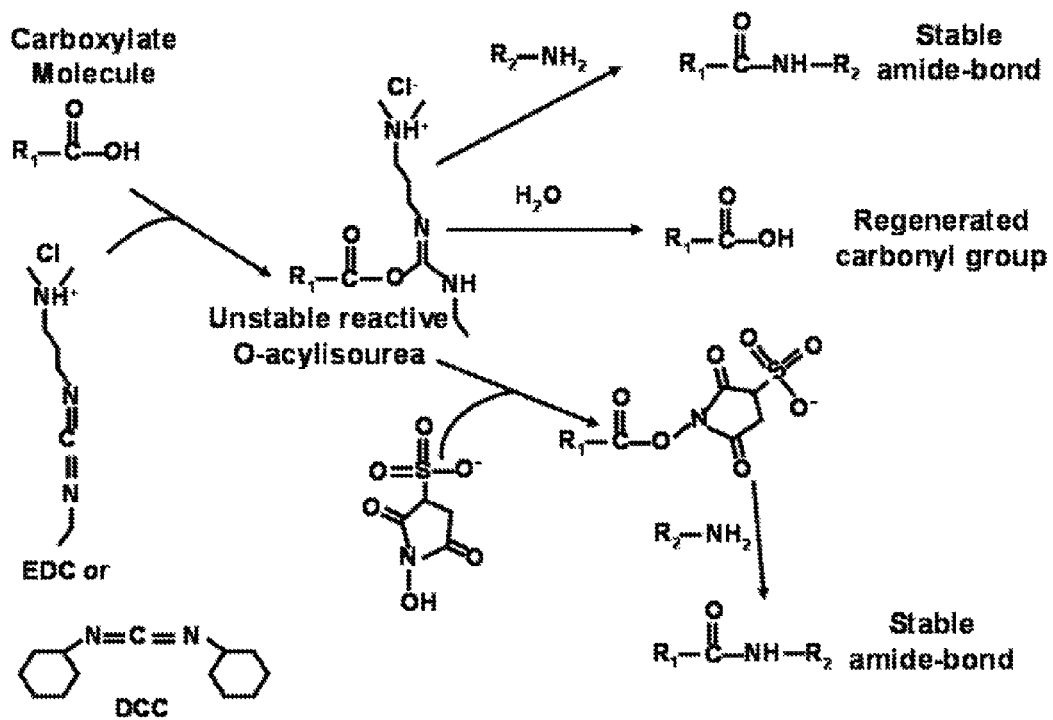
FIG. 2 depicts a diagram of various chemical reactions for making amide bonds that are useful in making the composition of the invention; $R_1$ can be oligonucleotide and $R_2$ can be polylysine, or polylysine-PEG; or $R_1$ can be PEG-carboxyl and $R_2$ can be polylysine, oligo-polylysine; or $R_1$ can be polyglutamate or polyaspartate and $R_2$ can be PEG-amine, oligonucleotide-amine; or $R_1$ can be polyglutamate-PEG or polyaspartate-PEG and $R_2$ can be oligonucleotide-amine. EDC is a water soluble version of DCC; both can be used to carry out the reactions.
Figure 3:
FIG. 3 depicts a diagram of various chemical reactions for attaching 5'- or 3'-amino containing oligonucleotides ($R^2$) to carrier ($R^1$) containing functional groups such as isothiocyanate, succinimidyl ester, or sulfonyl chloride. The carrier $R^1$ can be any polymers, amphipathic molecules, or oligonucleotide molecules. Polymer $R^1$ can be polyglutamate, polyaspartate, polyglutamate-PEG or polyaspartate-PEG.
Figure 3:
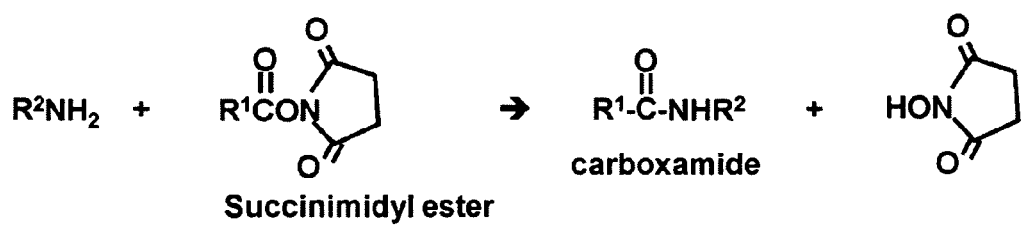
Figure 3:
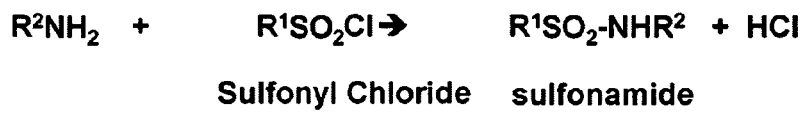

Acylation with carboxyl group generates a stable amide carbonyl as illustrated in FIG. 2. Isothiocyanates containing carrier, load molecules or protective chains form thioureas upon reaction with amines that are relatively stable covalent attachments (FIG. 3). Another example of the linking reaction is the coupling of polyglutamate or polyaspartate (with or without PEG) with amino-labeled oligos to form an oligonucleotide core (with and without PEG protection) of the present invention. Succinimidyl esters (NHS-esters) are excellent reagents for amine modification because the amide bonds they form (FIG. 3) are very stable. These reagents are can be stored long term if frozen or desiccated. NHS-esters are very reactive with primary amines and have low reactivity with secondary amines, alcohols, phenols (including tyrosine) and histidine. Succinimidyl esters will also react with thiols in organic solvents to form thioesters. Succinimidyl ester hydrolysis can compete with conjugation, but this side reaction is usually slow below pH 9 and the preferred reaction is pH 7.3.

Sulfonyl chloride containing carrier, protective chains, or load molecules are also reactive with primary amines of the oligonucleotides. However, these reagents are quite unstable in water, especially at the higher pH required for reaction with aliphatic amines, and as such are not commonly used in oligonucleotide attachment protocols (FIG. 3). Once conjugated, however, the sulfonamides that are formed are extremely stable. Sulfonyl chlorides can also react with phenols (including tyrosine), aliphatic alcohols (including polysaccharides), thiols and imidazoles.

Another method for attachment of amino-modified oligonucleotides to the carrier, protective groups or load molecules involves using an epoxide opening reaction to generate a covalent linkage between amino-modified oligonucleotides and epoxy (FIG. 6, line 3, except instead of oligo epoxide, it is carrier epoxide and the receiving alcohol is Amino-Modified Oligonucleotides) (Lamture et al., 1994 Nucleic Acids Res. 22:2121-2125); Beattie et al., 1995 Mol. Biotechnol. 4; 213-225). Attachment of amino-modified oligonucleotides on epoxy derivatized carrier is relatively thermostable, and the sensitivity of the epoxy ring to moisture is a major drawback and can lead to reproducibility problems (Adessi et al., 2000 Nucleic Acids Res. 28:e87). More commonly, attachment of amino-modified oligos involves reacting the receiving amino groups with excess pphenylene 1,4 diisothiocyanate (PDC) to convert the receiving primary amines to aminoreactive phenylisothiocyanate groups. Coupling of aminomodified oligos reaction to the phenylisothiocyanate groups follows, resulting in the covalent attachment of the oligonucleotide (Guo et al., 1994 Nucleic Acids Res. 22:2456-5465).

Modifications of the amino groups in the carrier, load molecule, or protective chain using homobifunctional crosslinking agents such as disuccinimidylcarbonate (DCS), disuccinimidyloxalte (DSO), and dimethylsuberimidate (DMS) to convert them into reactive isothiocyanates, N-hydroxysuccimimidy-esters (NHSesters) or imidoesters, respectively can easily be done. The chemistry of 1-ethyl-3-(3-dimethylaminopropyl)-carbodiimide hydrochloride (EDC, FIG. 2) can be employed with various carriers polyamino acids and polysaccharides to activate them.

Thiol-Modified Oligonucleotides and Chemistry of Attachment

The thiol (SH) modifier enables covalent attachment of an oligo to a variety of carriers, load molecules, and protective groups. A SH-modifier can be placed at either the 5'-end or 3'-end of an oligo. It can be used to form reversible disulfide bonds (ligand-S—S-oligo) or irreversible bonds with a variety of activated accepting groups in the carrier, load molecules, and/or protective groups. Options include active esters or isothiocyanate derivatives, as are commonly used for tagging free amino-modified oligonucleotides. Maleimide, bromide, iodide, or sulphonyl derivatives are suitable for attaching thiol-linked oligonucleotides to the carrier or load molecules essentially similar to that described for attaching thiol-linked oligonucleotides fluorescent dyes (Connolly and Rider, 1985 Nucleic Acids Res. 13:4485-4502, Zuckerman et al., 1987 Nucleic Acids Res. 15:5305-5321), biotin (Sproat, et al. 1987 Nucleic Acids Res. 15:4837-4848) and alkaline phosphatase (Li, et. al. 1987 Nucleic Acids Res. 15:5275-5287). Conjugation of oligonucleotides to enzymes, such as alkaline phosphatase or horseradish peroxidase, is commonly employed in commercial probe systems and thus the level of skill in the art to enable the present invention is not high. Enablement will use the existing conjugation chemistry for oligonucleotides conjugation to therapeutic peptides and proteins. The thiol modification also enables attachment to carrier (e.g. CPG-SH; Pierce) via a disulphide bond (Bischoff et al., 1987) or maleimide linkages. Thiol-modifiers can be incorporated at the start of oligonucleotide synthesis, placing the reactive SHgroup at the 3'-end using a thiol-CPG; thiol-modifiers can also be incorporated as the last step of synthesis using a thiol-phosphoramidite, placing the reactive SH-group at the 5'-end of the oligo and these are well known in the art.

Thiol-modified oligonucleotides are ideally stored frozen. Over time, SH-modified oligos will dimerize and will need to be reduced prior to use. Alternatively, oligos can be stored in 10 mM DTT (which will need to be removed prior to use). To ensure full reactivity, thiol-modified oligos should be reduced immediately attachment to the carrier, load molecules or protective chains.

In general, the oligo is treated with a reducing agent (like DTT) and this agent is fully removed prior to coupling. DTT is available immobilized on acrylamide resin (Reductacryl, Calbiochem Inc. Cat. No. 233157). The Reductacryl reagent can be used in a batch technique to reduce the disulfide bonds. The protocol to activate thiol containing oligonucleotide is as follow: Resuspend oligo plus resin in TE (Tris-EDTA) or similar buffer which is neutral or slightly alkaline such as pH 7.5. Use a ratio of 1 mg oligo with 50 mg resin to ensure complete reduction. Stir or agitate at room temperature for 15 minutes. Remove Reductacryl™ by filtration (e.g., pass through a syringe filter). Activated oligo is then added directly into the coupling reaction containing carrier, load molecules or protective groups or can be stored for brief periods of time before use. Thiol containing oligonucleotide can also be activated by liquid DTT. The oligo can be treated with liquid DTT or stored in DTT, which must be removed immediately before use. Solution of oligonucleotide in TE plus DTT with 100 uM oligo in 10 mM DTT in 1×TE is pass through a large bed volume Sephadex column to remove DTT. Note that small bed volume spin columns can allow trace DTT to remain with the oligo, which can interfere with subsequent coupling reactions. Thiol containing oligonucleotide can also be activated by bulk reduction by reconstituting the oligonucleotide (up to 1 mg of oligo can be used) in 100 ul of 2% TEA (triethylamine), 50 mM DTT and allow to stand at room temperature for 10 min. Remove DTT using one of the 3 methods: 1) Extraction: extract 4× using 400 ul of ethyl acetate (layers readily separate and the DTT will partition with the ethyl acetate and the oligonucleotide will partition in the aqueous phase). 2) Recover oligo by acetone precipitation. Add five volumes of acetone solution (2% LiClO4 w/w in acetone) to one volume of the oligo solution in a 14 mL tube. Chill the resulting solution at −20° C. for 15 minutes and centrifuge the sample at 2500-5000 RPM for 10-5 minutes, respectively. Remove the supernatant and dry the sample under vacuum to remove trace acetone. To remove LiClO4 and other salts, the sample can be washed with 2-3 mL of n-butanol centrifuged again followed by removal of the butanol supernatant. 3) Size exclusion or gel filtration chromatography: load the sample of oligonucleotide on a Sephadex G25F column that has been thoroughly washed with distilled water. Elute the column with water by gravity flow and collect fractions. Measure the UV absorbance at 260 nm. The first eluting peak in the void volume is the oligonucleotide. Concentrate fractions using a SpeedVac evaporator. Any oligonucleotide that is not used immediately should be stored frozen. Over time, the oligo will oxidize and the above procedure will need to be repeated before coupling.

As a class the cross-linkers that can be used to attach thiol-modified oligonucleotides to carriers, load molecules or protective groups are hertobifunctional, meaning that they possess functional groups capable of reaction with two chemically distinct functional groups, e.g. amines and thiols. The linkers serve two purposes: to covalently bind two distinct chemical entities which otherwise would remain unreactive toward each other and as a physical spacer which provides greater accessibility and or freedom to each of the linked biomolecules (Chrisey et al., 1996 Nucleic Acids Res. 24:3031-3039). A number of heterobifunctional cross linkers have been developed for covalent attachment of thiol-modified DNA oligomers to amino groups (Chrisey et al., 1996 Nucleic Acids Res. 24:3031-3039). These cross linkers combine groups reactive toward amines such as N-hydroxy-succinimidyl esters and groups reactive toward thiols such as maleimide or alpha-haloacetyl moieties. The use of one such cross linker, succinimidyl 4-[maleimidophenyl]butyrate (SMPB) to link a thiol-modified oligo to an amine derivatized solid support is well known and can be applied to make the present invention. The use of SMPB to cross link thiol modified oligos and polylysine, amino PEG, or peptide with free amino groups is straight forward and the chemistry is well known in the art.

Spacer or Linking Groups

The spacer or linking groups that can be used to covalently assemble the component of the oligonucleotide-core composition can be selected from any number of homobifunctional or heterobifunctional crosslinkers widely available commercially (Pierce Chemicals/Biotechnology; Rockford, Ill.). Crosslinker will ideally have two reactive functional groups that are reactive to any of amino, carboxyl, hydroxyl, or thiol groups or their activated analogs. In some cases each of the functional group in the spacer is pre-activated to react spontaneously and specifically to amino, carboxyl, hydroxyl, or thiol groups. In some cases, the functional groups that will be receiving one end of the spacer will need to be activated. Ideally, the spacer will have length appropriate for specific oligonucleotide or protective groups to provide sufficient freedom for the oligonucleotide to base pair or hydrogen bond with its complement. Ideally, the distance between the two end of the spacer or linking groups will be between 1 to 100 Angstrom in distance and more preferably from 2 to 50 Angstrom and more preferably between 3 to 25 Angstrom in distance. Non-limiting example of the simplest spacer is 8-hydroxy octanoic acid wherein the hydroxyl group on one end (C8) is linked to the 5'-phosphate group of the oligonucleotide and the carboxyl group (C1) is reacted to the amino group of the carrier to form amide bond which provides a distance of about 10-12 Angstrom. In most cases the spacer will be incorporated during oligonucleotide synthesis described above and is known to those skilled in the art. A number of heterobifunctional reagents from commercial sources (like Pierce Chemicals/Biotechnology, Rockford, Ill.) are used to link the two components to form a functional oligonucleotide-core carrier composition. Non-limiting examples of spacers or linkers from Pierce are Succinimidyl 4-(maleimidomethyl) cyclohexane-1-carboxylate (SMCC), N-Succinimidyl 3-(2-pyridyl dithio) propionate (SPDP), N-Succinimidyl (4-iodoacetyl) aminobenzoate (SIAB), Succinimidyl 4-(p-maleimidophenyl) butyrate (SMPB), and the like. These reagents are adapted to link the carrier and oligonucleotide and/or protective chains by separate reaction of the two components with each other.

Protective Chains or Groups

The subject oligonucleotide-core carrier compositions, and methods of making and using the same, may achieve a number of desirable results and features provided by the protective chains, one or more of which (if any) may be present in any particular embodiment of the present invention. The protective chain of the composition is preferably a polymer of ethylene oxide (poly(ethylene glycol), i.e. PEG or a mono-methoxy ether of poly(ethylene glycol) i.e. MPEG. A protective chain is useful because: 1) it ensures the solubility the composition while maintaining a high drug payload; 2) a protective chain assists in the formation of a steric barrier which can prevent oligonucleotide-containing load molecules (peptides, proteins and other therapeutic agents) from binding or interaction with other macromolecules, enzymes and cells in the body; 3) a protective chain provides load molecules (peptides and proteins and drugs) with long circulation times or biological half-lives in vivo (e.g. for decreasing glumerular filtration in kidneys, decreasing kidney and liver uptake, decreasing macrophage uptake . . . etc.) and thereby make the composition to function as a circulating depot; 4) a protective chain decreases undesirable immunogenicity of the carrier or its load molecules such as a RNA, siRNA, DNA, peptide or protein drug; 5) the abnormal permeability of tumor vessels assists accumulation of the carrier with load molecules in a tumor or inflammation site by delivering the load molecules or anti tumor compounds to the tumor which is especially useful for treating tumors; 6) a protective chain may also provide additional binding strength; and 7) a protective chain may provide binding to the surface, such as to a mucosal surface by interaction with mucosa.

The protective chain of the oligonucleotide-core carrier composition may be, e.g., polyethylene glycol, methoxypolyethylene glycol, methoxypolypropylene glycol, a co-polymer of polyethylene glycol, methoxypolyethylene glycol, or methoxypolypropyleneglycol, or derivatives thereof. In addition, the protective chain may be a block co-polymer of polyethyleneglycol and one of the group of polyamino acids, polysaccharides, polyamidoamines, polyethyleneamines, or polynucleotides. The protective chain may also be a co-polymer of polyethylene glycol including a monoester of a dicarboxylic acid. The protective chain may also be an ethoxylated or methoxylated polysaccharides. The protective chain preferably has a molecular weight of 500-10,000 Daltons.

In another related aspect, the oligonucleotide-core carrier composition includes a protective chain which is polyethylene glycol, polypropylene glycol, a co-polymer of polyethylene glycol and polypropylene glycol; or a alkoxy derivative thereof, preferably methoxypolyethylene glycol, methoxypolypropylene glycol, or a co-polymer of methoxypolyethylene glycol and methoxypolypropyleneglycol; the protective chain may be polyethylene glycol monoamine, methoxypolyethylene glycol monoamine, methoxy polyethylene glycol hydrazine, methoxy polyethylene glycol imidazolide or a polyethylene glycol diacid; the protective chain is a block co-polymer of polyethylene glycol and one of the group of polyamino acids, polysaccharides, alkoxylated polysaccharides, polyamidoamines, polyethyleneamines, or polynucleotides; the protective chain may be a co-polymer of polyethylene glycol comprising a monoester of a dicarboxylic acid; and the protective chain has a molecular weight of 500-10,000 Daltons.

Further examples of protective chains include methoxy poly(ethylene glycol) imidazolide block-copolymer of poly(ethylene glycol) and one or several polymers represented by polyaminoacid, poly-lactideglycolide co-polymer, polysaccharide, polyamidoamine, polyethyleneimine or polynucleotide (see polymeric carrier) where these blocks are preferably alternated to give a preferably linear block-copolymer. Overall molecular weight of a protective chain is preferentially larger than 300 but preferably not exceeding 10,000. A protective chain or chains are linked to the polymeric carrier by preferably a single linkage.

Attachment of Protective Chains to the Carrier

The present invention also relates to an oligonucleotide-core carrier composition comprising a polymeric carrier with pendant oligonucleotide groups or wherein oligonucleotide group is covalently linked (by a linker or spacer) to any one of 1) amino groups 2) carboxyl groups, 3) hydroxyl groups, or 4) thiol groups exposed along the polymeric carrier and further comprising of protective chains covalently linked (by a linker or spacer) to any one of 1) amino groups 2) carboxyl groups, 3) hydroxyl groups, or 4) thiol groups exposed along the polymer or the oligonucleotide groups. A non-limiting example of these modification along the polymeric carrier is 1) amide, ester, ether, and disulfide attachment of protective chains comprising polyoxyethyleneglycol (PEG). Other examples of protective chains which are not intended to limit the scope of this invention are an alkoxyPEG, polyoxypropyleneglycol, alkoxy polyoxypropyleneglycol and analog or derivative thereof. In a further embodiment, the protective side chain comprises poly(ethylene glycol). In a further embodiment, the protective side chain comprises alkoxy poly(ethylene glycol). In a further embodiment, the protective side chain comprises methoxy poly(ethylene glycol) (MPEG). In a further embodiment, the protective side chain comprises ethoxylated or methoxylated polysaccharides such as dextran, hyaluronan or polysialic acid. These can be attached to the polymeric carrier using any of the chemical bonds mentioned above.

Another object of the present invention is to provide a method of attaching protective chains to the carrier. The modifications can be done by amide bond formation. As an example that is not intended to limit the scope of this invention, the carboxyl containing protective molecule can be attached to the amino group of the carrier using carbodiimide containing reagent such a 1-ethyl-3-(3-dimethylaminopropyl)-carbodiimide or dicyclohexylcarbodiimide. A carbodiimide reagent contains a functional group consisting of the formula N=C=N. During the process of coupling reaction, the activated carboxyl group O-acylisourea-intermediate can be stabilized by forming N-hydroxysuccinimide ester using N-hydroxysuccinimide. This relatively stable intermediate can react with the amino group of carrier such as polylysine or chitosan to form amino-acyl bond or amide bond. Similar result can also be accomplished by reacting aldehyde containing protective group to the amino group along the carrier. The aldehyde can react with the amino group of carrier such as polylysine or chitosan to form amino-acyl bond or amide bond.

The modification of the carboxyl groups in the polymeric carrier is the amide covalent attachment of an amino group containing protective chains comprising amino polymethoxyoxyethyleneglycol. As an example that is not intended to limit the scope of this invention, the protective chain can be an amino PEG which can be represented by formula $-NH(CH_2)_n NHCOCH_2-A-OR_3$, $-NH(CH_2)_n NHCO(CH_2)_n COOCH_2CH_2-A-OR_3$, where n is 2-22; A is $[OCH_2CH_2]_x$ or $[OCHCH_3CH_2]_x$, where x is 17-250, or various combinations of $[OCH_2CH_2]$, $[OCH_2CH_2]$, and/or $[OCHCH_3CH_2]$ with total of 17-250 units, $R_3$ is H, $(CH_2)_p CH_3$ or $(CH_2)_p COOH$, and p is 0-7.

The present invention also relates to an oligonucleotide-core carrier composition comprising a polymeric carrier or polymeric carrier with oligonucleotide group comprising modified hydroxyl groups along the polymer. The modification of hydroxyl groups includes ester attachment of protective groups or molecules comprising acyl polymethoxyoxyethyleneglycol. As an example that is not intended to limit the scope of this invention, the protective group can be a PEG with acyl or carbonyl represented by —CO and attached to O of hydroxyl group of carrier to form ester. The acyl PEG or its derivative can be represented by formula $-CO(CH_2)_n NH-COCH_2-A-OR_3$, $-COCH_2CH_2-A-OR_3$, or $-COCH_2-A-OR_3$, where n is 2-22; A is $[OCH_2CH_2]_x$ or $[OCHCH_3CH_2]_x$, where x is 17-250, or various combinations of $[OCH_2CH_2]$, $[OCH_2CH_2]$, and/or $[OCHCH_3CH_2]$ with total of 17-250 units, $R_3$ is H, $(CH_2)_p CH_3$ or $(CH_2)_p COOH$, and p is 0-7.

The present invention also relates to an oligonucleotide-core carrier composition comprising a polymeric carrier or polymeric carrier with oligonucleotide groups that has modified hydroxyl groups along the polymer. In a further embodiment, the present invention relates to the above described composition wherein the carrier comprises protective side chains. In a further embodiment, the protective side chain comprises poly(ethylene glycol). In a further embodiment, the protective side chain comprises alkoxy poly(ethylene glycol). In a further embodiment, the protective side chain comprises methoxy poly(ethylene glycol) (MPEG). In a further embodiment, the protective side chain comprises polysialic acid. In a further embodiment, the protective side chain comprises poly(acrylamide). In a further embodiment, the protective side chain comprises poly(vinylpyrrolidone). These can be attached to the polymeric carrier using any of the chemical bonds mentioned above.

Another object of the present invention is to provide methods of attaching protective chains to the carrier. The modification of hydroxyl group can be facilitated by synthesis of acyl halides of protective molecules. Synthesis of acyl halides can be done by reaction of the carboxylic acid moiety of protective molecules with dichlorosufoxide ($SOCl_2$) or other reagent known to those skilled in the art. The resulting acyl halides are reactive to alcohols including serine, threonine, and tyrosine residue of poly amino acids. The reaction will result in an ester bond formation essentially attaching the protective groups or molecules into the carrier. PEG-epoxide, PEG-isocyanate, PEG-PNC (PEG-nitrophenylcarboxyester) are the PEG analogs that may be used to modify the hydroxyl groups forming ether, ester, and urethane linkage respectively between protective group and the carrier.

Targeting Molecules

Yet another object of the present invention is to provide a pharmaceutical composition comprising oligonucleotide-core composition with protective groups, an oligonucleotide-containing load molecule bound to the complementary oligonucleotide of the carrier by hydrogen bonding, and a targeting molecule covalently linked to the protective groups to facilitate the localization of the pharmaceutical composition to the tissue of interest.

The targeting group may be covalently linked to the load molecule or the protective chain or both by amide, ester, ether, or disulfide bonds. The targeting group may be an antibody, fragment of an antibody, chimeric antibody, where the antibodies are polyclonal or monoclonal; peptides; enzymes; quasi substrates of enzymes; lectins; or saccharide ligands of lectins detachably or non-detachably linked to the composition, enzyme, lectin, saccharide ligand, or peptide fragment. The targeting molecule The role of a targeting moiety or group is to place the compositions of the present invention in close proximity to a target within a patient's body. In this manner, it is envisioned that the present invention can optionally utilize a targeting agent or molecule.

Examples of targeting moieties include: (i) chemotactic proteins and peptides including monocyte chemotactic protein 1 (MCP-I), N-formyl-methionyl-leucyl-phenalanine; (ii) colony stimulating factors including GM-CSF, CSF-1, and receptors and antibodies thereto; and platelet factor 4; (iii) growth factors including TGF-beta and VEGF; (v) adhesive cell-surface glycoproteins including E-selectin, VCAM-1, and VCAM-beta; (iv) carbohydrates including C-deoxy-D-glucose, and IsF-2-fluorodeoxy-D-glucose; (vi) components of a vascular inflammatory response including C1, C1q, C1Ir, C1s, C2, C3, C3a, C3b, C4, C4C2, C4C2C3b, C5a, C5b and C5a; (vii) interleukins including IL-1, IL-1a, IL-10, IL-2, IL-3, IL-6, IL-7, and IL-8; (viii) various interferons including interferon alpha and interferon gamma; (ix) tumor necrosis factor alpha (TNF-a); and (x) lipids including liposomes, polyethylene glycol coated liposomes, cholesterol, esters of cholesterol, lipoproteins including LDL, HDL, oxidized LDL, and lipid receptors.

Load Molecules

The invention also includes oligonucleotide or oligonucleotide-containing load molecule wherein the oligonucleotide in the load molecule (i.e. oligonucleotide covalently linked to the load molecule) is essentially complementary to the oligonucleotide covalently linked to the carrier. The term "essentially complementary" means it is "50-100%" complementary. For the purpose of the present invention, the load molecules are any molecules with covalently linked oligonucleotide or oligonucleotide itself. Also for the purpose of the present invention, when the load molecule is a therapeutic agent, the therapeutic agent is understood to have oligonucleotide covalently linked to the therapeutic agent. The load molecules, for the purpose of the present invention, include one or more of the following: RNA, siRNA, miRNA, DNA, antisense DNA, a nucleotide aptamer, a peptide aptamer, a therapeutic agent or a diagnostic agent. It should be noted that some RNAs, DNAs, siRNAs, miRNAs, antisense DNAs, antisense RNAs, nucleotide aptamers, and peptide aptamers are also classified as therapeutic agent. Therapeutic agents that can be made into load molecules by attaching oligomers can be peptide and proteins and include cytokines, lymphokines, hormones, hormone agonists, hormone antagonists, antibiotics, analgesics, toxins, photo-toxins, cytostatics, cytotoxics, psychotropics, immunosuppressive agents, antibacterial agents, anti-viral drugs, and anti-fungal drugs. These load molecules can be under the classification of proteins, antibody, antibody fragments, peptides, recombinant peptides, peptides isolated from plants, peptides isolated from fungi, peptides isolated from animals, peptide isolated from bacteria, peptide isolated from viruses, peptides isolated from cells in culture, synthetic peptides, peptidomimetic, deoxyribonucleic acid, ribonucleic acid, oligonucleotide, other nucleic acid, oligosaccharide, carbohydrates; lipids; photo-sensitive organic compounds, and proteoglycan.

Non-limiting examples of therapeutic agent load molecules in which oligonucleotide can be attached to facilitate loading into the present invention are glucagon-like-peptide, glucagon-like-peptide derivatives, exenatide, glucagon-like-peptide-1, glucagon-like-peptide-2, leptin fragment, Gastric inhibitory polypeptide(GIP), Epidermal Growth Factor (EGF) receptor ligand, EGF, Tranforming Growth Factor alpha (TGF-alpha), Betacellulin, Gastrin/Cholecystokinin receptor ligand, Gastrin, Cholecystokinin, lysostaphin, interferon, interferon gamma, interferon beta (e.g., interferon-beta 1, interferon-beta 2), interferon alpha (e.g., interferon alpha-2a or interferon alpha-2b), interleukin-1, interleukin-2, interleukin-4, interleukin-6, interleukin-8, interleukin-10, interleukin-12, tumor necrosis factor (TNF), tumor necrosis factor alpha (TNF-alpha), tumor necrosis factor beta (TNF-beta), auristatin, nisin, insulin, insulin-like growth factor, insulin-like growth factor 1 (IGF1), growth hormone, human growth hormone, growth hormone releasing hormone (GHRH), nerve growth factor (NGF), brain-derived neurotrophic factor (BDNF), enzymes, endostatin, angiostatin, trombospondin, urokinase, streptokinase, blood clotting factor VII (Factor-VII), blood clotting factor VIII (FactorVIII), granulucyte-macrophage colony-stimulating factor (GMCSF), granulucyte colony-stimulating factor (GCSF), thrombopoetin, calcitonin, parathyroid hormone (PTH) and its fragments, erythropoietin, atrial natriuretic factor (ANF), monoclonal antibodies, monoclonal antibody fragments, somatostatin, protease inhibitors, ziconotide, teriparatide, Hematide, tissue factor pathway inhibitor (TFPI), desferroxamine (DFO), oxytocin, cyclosporine, and Integrilin (eptifibatide).

The load molecules also includes siRNA against Ghrelin and NPY for the treatment of Obesity/Type 2 diabetes; siRNA against Cathepsin L and Myostatin for the treatment of muscular dystrophy; siRNA against TSLP (thymic stromal lymphopoetin), Interleukin(IL)-4, IL-13; IL-4, IL-13, STAT-6 (signal transducer and activator of transcription-6), MIP-1 alpha (macrophage inflammatory 1 alpha), RANTES (Regulated on activation, normal T-cell expressed and secreted chemokine), CCR1 (chemokine receptor 1), and CCR3 (chemokine receptor 3) for the treatment of Asthma/Airway inflammation/ectopic dermatitis; siRNA against INF-gamma (interferon gamma), TNF-alpha (tumor necrosis factor alpha), Interleukin(IL)-12, IL-8, CXCR1 (CX variant chemokine receptor 1), MCP-1 (monocyte chemotactic protein 1), and CCR2 (CX variant chemokine receptor 2) for the treatment of Psoriasis and rheumatoid arthritis; siRNA against CCR4-8 (chemokine receptor 1 to 8) and CXCR3-5 (CX variant chemokine receptor 3 to 5) for the treatment of various inflammatory diseases; siRNA against CCR5 (chemokine receptor 5) and vital virus proteins like gp120, gp41, p17, p24, RT (reverse transcriptase), proteases for the treatment of HIV infection; siRNA against FAS (CD95), FAS-L, FADD, Caspase-8, IL-1, IL-6, Bak (Bcl-2 associated protein k), Bax (Bcl-2 associated protein x), and Bid (Bcl-2 associated protein d) for the treatment of sepsis;

siRNA against Bcl-2 (B-cell chronic lymphatic leukemia associated protein 2), Bcl-XL (Bcl-2 related gene xl), HLA-G (Human leukocyte antigen class G), IGF-1 (Insulin-like growth factor-1), EGF (epidermal growth factor), FGF (fibroblast growth factor), VEGF (vascular endothelial growth factor), VEGFR (vascular endothelial growth factor receptor), IGFR (insulin-like growth factor receptor), EGFR (epidermal growth factor receptor), FGFR (fibroblast growth factor receptor), TGF-beta (transforming growth factor beta), Caspase 3, CEACAM6 (Carcinoembryonic antigen-related cell adhesion molecule 6), HPV-E6 (human papiloma virus protein E6), HPV-E7 (human papiloma virus protein E7), H-Ras gene, P100a gene, CREB (cAMP response element binding), BRAF gene, ATF2 (activating transcription factor 2), HER2 (Human EGF-like Receptor No. 2), and N-myc gene for the treatment of cancer; siRNA against Cox1 or 2 (cyclooxygenase 1 or 2), GluR2 (glutamate receptor 2), and DAT (Dopamine active transporter) for the treatment of CNS disorder; siRNA against VEGFR1 (vascular endothelial growth factor receptor 1) and TGF-b-RII (Transforming growth factor beta receptor II) for the treatment of ophthalmic disorder; siRNA against TNF-alpha (tumor necrosis factor-alpha for rheumatology) and IL-1-beta (interleukin beta for liver mediated lung inflammation) for the treatment of inflammation; siRNA against Facipain-1,2 protein (malaria), Fas gene (hepatitis), Capsid (Poliovirus), CCR5 (HIV), NS5A (Hepatitis), NP (influenza), PA (influenza), and HBV for the treatment of infection.

The load molecules also includes anti-cancer siRNA against HRAS (v-Ha-ras Harvey rat sarcoma viral oncogene homolog), NRAS (neuroblastoma RAS viral (v-ras) oncogene homolog), KRAS (v-Ki-ras2 Kirsten rat sarcoma viral oncogene homolog), MYC (v-myc myelocytomatosis viral oncogene homolog, avian), MYCN (v-myc myelocytomatosis viral related oncogene, neuroblastoma derived, avian), MYB (v-myb myeloblastosis viral oncogene homolog, avian), Jun-oncogene, FOS (v-fos FBJ murine osteosarcoma viral oncogene homolog), Oncogenic ABL1 (v-abl Abelson murine leukemia viral oncogene homolog 1 (this gene is an oncogene only if the SH3 domain is truncated, as happens regularity in certain leukemias), SRC (v-src sarcoma (Schmidt-Ruppin A-2) viral oncogene homolog, avian), FES (Feline sarcoma oncogene), RAF1(v-raf-1 murine leukemia viral oncogene homolog 1), REL (v-rel reticuloendotheliosis viral oncogene homolog, avian), RELA (v-rel reticuloendotheliosis viral oncogene homolog A, nuclear factor of kappa light polypeptide gene enhancer in B-cells 3, p65, avian), RELB (v-rel reticuloendotheliosis viral oncogene homolog B, nuclear factor of kappa light polypeptide gene enhancer in B-cells 3, avian), FGR (Gardner-Rasheed feline sarcoma viral (v-fgr) oncogene homolog), and KIT (v-kit Hardy-Zuckerman 4 feline sarcoma viral oncogene homolog).

The biologically active therapeutic agents with suitable oligonucleotide attachment site can be used as load molecules in the present invention. These include compounds which by themselves do not pass (or which pass only a fraction of the administered dose) through the gastrointestinal mucosa and/or are susceptible to chemical and/or enzymatic cleavage by acids and enzymes in the gastrointestinal tract; or any combination thereof. These include proteins, polypeptides; peptides; hormones; polysaccharides, and particularly mucopolysaccharides and mixtures thereof.

In a further embodiment, the present invention relates to the above described composition wherein more than one type of load molecule is bound to the oligonucleotide group of the polymeric carrier.

In a further embodiment, the present invention relates to the above described composition wherein the load molecule is a diagnostic agent. These include fluorescent molecules, paramagnetic molecules, and radioactive molecules.

Yet another object of the present invention is to provide a method of loading the a oligonucleotide-core carrier composition of the invention with load molecule by mixing sufficient amount of load molecule and the oligonucleotide-core carrier in suitable solvent and optionally co-lyophilizing both the load molecule and the oligonucleotide-core carrier. Sufficient amount of load molecule may vary depending on the load molecule but preferably between 1 to 100% of the weight of the oligonucleotide-core carrier.

It is the intention of the present invention to provide a method of treatment of various diseases described in the "The Merk Manual of Diagnosis and Therapy" (published 1992 by Merck Laboratories which is a division of Merck & Co., Inc, Rahway, N.J.) using compositions described in the present invention along with appropriate oligonucleotide-containing load molecule selected from that described in PDR or Physician Desk Reference (published 2001 by Medical Economics Company, Inc. Montvale, N.J.) and modified to contain oligonucleotide. The Merk Manual of Diagnosis and Therapy and the PDR are hereby incorporated by reference. The appropriateness of a load molecule for particular disease can be ascertained by checking "The Merk Manual of Diagnosis and Therapy" or the PDR.

The Oligonucleotide-Core Carrier Composition

Figure 1:
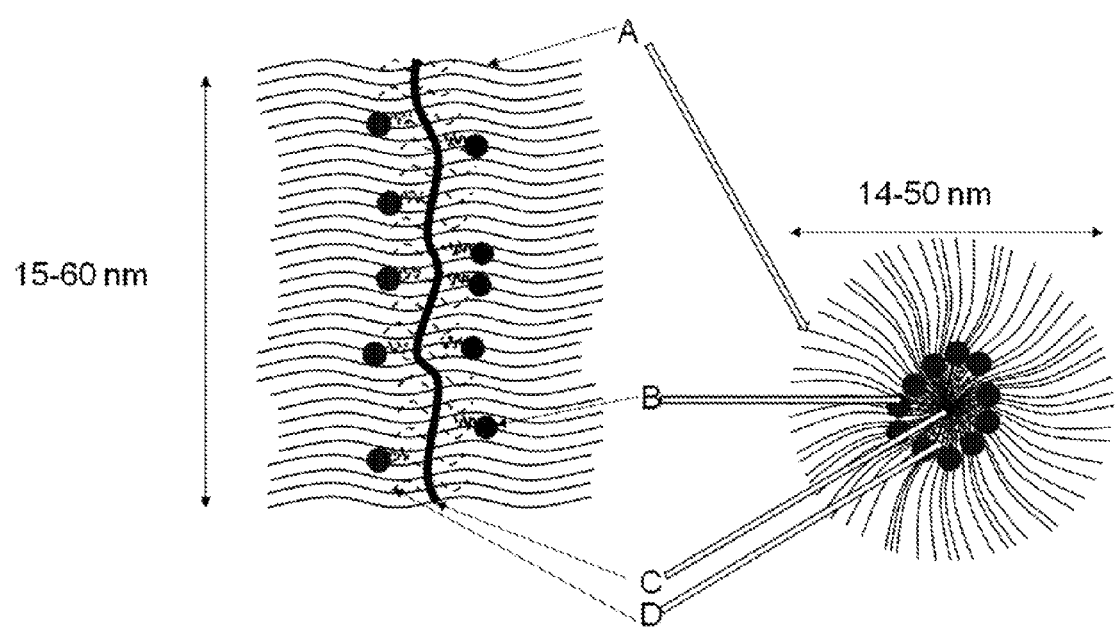
FIG. 1 depicts a schematic representation of one embodiment of the oligonucleotide-core composition of the invention: A) protective side chains; B) oligonucleotide-containing load molecule with diameter of 3 nm; C) polymeric core; and D) oligonucleotide covalently linked to polymeric core. The dimension of the carrier is also shown to emphasize that it is greater than the 4 nm glumerular filtration cut off, whereas oligonucleotide and oligonucleotide containing load molecules are below this cut off. The followings are example of proteins and their diameter: albumin hydrated (diameter=7.2 nm); growth hormone hydrated (diameter=3 nm); glumerular filtration diameter<4 nm; beta-2 macroglobulin (diameter=3.2 nm); myoglobin (diameter=3.9 nm); hemoglobin (diameter=6.5 nm); gamma globulin (diameter=11.1 nm); and Bence-Jones protein (diameter=5.5 nm).

One embodiment of the oligonucleotide-core carrier compositions with complementary oligonucleotide-containing load molecules is represented in FIG. 1. This representation is not intended to limit the scope of the invention but rather to show some important features of the invention. The scale of the sizes of the components of the oligonucleotide-core carrier composition and load molecules are estimated based on the length of chemical bond present in the composition. In this representation, the oligonucleotide covalently linked to the load molecules will be hydrogen bonded to the complementary oligonucleotide component of the carrier and will be protected by the linear protective chains radiating from the carrier. The protective chains may be attached independently to the carrier or may be attached to the end of the oligonucleotide group of the carrier. In the former, the protective chain may be attached to the carrier in various ways, preferably by amide bond, ester bond or disulfide bond. In the latter, the protective chain may be attached to the oligonucleotide group, preferably to the terminal portion of the oligonucleotide group of the carrier. The oligonucleotide group of the carrier is preferably attached to the carrier by an amide bond, ester bond, of disulfide bond. The load molecules are reversibly bound to the oligonucleotide portion of the oligonucleotide-core carrier by base paring or hydrogen bonding interaction which can be strengthened by lengthening the interacting oligonucleotides. The loading of load molecules to the oligonucleotide-core carrier can be accomplished by simply mixing the load molecule with the oligonucleotide-core carrier in the ratio of oligonucleotide-core carrier to load molecule of between about 1:0.1 to 1:10; weight to weight.

The mixing is preferably done in water or phosphate buffered saline depending on the properties of the load molecule, followed optionally by lyophilization. Other excipients can optionally be added to the complex to control pH, tonicity, and viscosity. The oligonucleotide-core carrier-load molecule complex can be lyophilized in portions of known amounts for administration to a patent needing treatment with the particular load molecule in the complex. The lyophilized complex can be reconstituted in saline or water for administration to patient to treat diseases such as, for example, insulin-insufficient diabetes, obesity, vascular diseases, heart diseases, stroke, blood clot in the vessel, cancers, cancer of the liver, cancer of the kidney, cancer of the colon, cancer of the pancreas, cancer of the lung, cancer of endocrine glands, pituitary tumor, soft tissue tumor, cancer of the tongue, cancer of the bone, leukemia, melanoma, lymphomas, Hodgkin lymphoma, non-Hodgkin lymphoma, hepatitis, hepatitis A, hepatitis B, hepatitis non-A non-B, hepatitis C, Alzheimer's disease, Parkinson's disease, psychiatric disorders, schizophrenia, bipolar disorder, endocrine disorder, hypertension, hypotension, clotting factor deficiency, parasitic diseases, fungal infection, bacterial infection, staphylococcal infection, bacillus infection, necrotizing infection, gangrene, poisoning, poisoning with bacterial toxins, and poisoning with venom.

The affinity of load molecules to the oligonucleotide-core carrier can be adjusted by changing the length of the oligonucleotide chains and increasing the proportion of G:C content. It is understood that a 15 mer polyG covalently linked to the carrier will have strong interaction with load molecule covalently linked to 15 mer polyC than the 15 mer polyA covalently linked to the carrier with load molecule covalently linked to 15 mer polyA. This is because G:C pairing has 3 hydrogen bonding each and A:T pairing has only 2 hydrogen bonding each. In addition, a mismatch (only partially complementary) will decrease the strength of the binding. The oligonucleotide-core carrier of the present invention can have a protective chain for every oligonucleotide group resulting in an oligonucleotide group every 0.3 nm. If there are less protective groups (one protective group per two or more oligonucleotide groups) a distance of 0.15 nm between every oligonucleotide group can be achieved, which is quite high. Since each oligonucleotide group can have between 2 to 100 nucleotides, inclusive, the number of hydrogen bonding that determines the binding of complementary oligonucleotide in the load molecules to the oligonucleotide-core carrier can be very high if desired. High affinity oligonucleotide-core carriers can be design by increasing the length of oligonucleotide groups attached to the carrier and that attached to the load molecules and using mainly G and C bases. In the case of siRNA load molecules, only the length of the carrier can be controlled up to the length of siRNA. The base content cannot be controlled since siRNA needs it native sequence to have biological activity. The maximum number of oligonucleotide groups can be placed on all of the available sites on the polymeric carrier and since there will be no site left for the protective group, the protective groups can be attached to the terminal ends of the oligonucleotide groups. This can increase the capacity of the carrier to handle large number of load molecules carrying complementary sequence.

There has been a long felt need to have a drug or therapeutic drug delivery system that has properties such as protection from degradation, slow release, and control of the amount that is free at any given time. The amount of drug that is free will be determined by a binding equilibrium defined by the dissociation constant of the carrier to the load molecule. The dissociation constant can be determined between a specific load molecule and a carrier with a defined composition.

Determination of Dissociation Constant Between the Oligonucleotide Core Carrier and the Load Molecule The oligonucleotide-core carrier reversibly bind load molecule with complemetary oligo nucleotide by complementary hydrogen bonding to give a defined association constant (Ka) or its inverse which is also called dissociation constant (Kd). This will determine the release of load molecule from the carrier which will only occur to satisfy the Kd. The formation of hydrogen bonding is by complementation to either form a duplex or on occasion a triplex. To determine the dissociation constant for oligonucleotide-core carriers with a molecular weight greater than 100 kDa, place 100 ul aliquots of oligonucleotide-core carrier (1 mg/ml in phosphate buffered saline, PBS; 50 mM Phosphate, 150 mM NaCl, pH 7.4) in 10 tubes in triplicate. As controls, prepare another set of 10 tubes in triplicate without oligonucleotide-core carrier but with 100 ul of PBS. Place triplicate-100 ul-aliquots of 1000 nM, 500 nM, 100 nM, 50 nM, 10 nM, 5 nM, 1 nM, 0.5 nM, 0.1 nM, and 0 nM solution of load molecule dissolved in phosphate buffered saline into all the tubes including controls. Mix by vortex and incubate the solution for 1 hr at 37° C., filter all the solution through a 100 kDa cut-off membrane (from Millipore, Bedford, Mass.) by centrifugation. The load molecules that go through the filter are the concentration of free load molecule in solution. The control tubes without the oligonucleotide-core carrier will be the total amount of load molecules available for binding. The bound load molecules can be calculated by subtracting the free from the corresponding control that received the same concentration of load molecules but without the oligonucleotide-core carrier. Graph the bound/free load molecules along the y-axis against bound load molecule (nM) along the x-axis. The slope of the graph of bound/free on the Y axis and bound (nM) x-axis will be the $-1/Kd$ where Kd is the dissociation constant. The quantification of load molecules that went through the filter can be done by means such as, PCR, Elisa (Enzyme-linked Immunosorbent assay), HPLC, or HPLC/MS.

Maintenance of Free Load Molecule Concentration

The free load molecule concentration over time can be predicted from the equilibrium constant between the free load molecule and load molecule bound to the oligonucleotide-core carrier. This can be determined in an isotonic saline solution. The equilibrium constant can be adjusted by changing the length and amount of oligonucleotide moieties within the carrier and the size and amount of protective groups. The smaller the size and amount of oligonucleotide moieties, the higher free load molecule concentration at any given time up until the load molecule reservoir is depleted. The longer the sequence and amount of oligonucleotide moieties, the lower the free load molecule concentration at any given time up until the load molecule reservoir is depleted. In the latter scenario, the reservoir will take longer to deplete and the release of load molecule will be prolonged. Such a release profile may result in prolonged delivery if preferred (over, say 3 to about 4,000 hours, or alternatively about 10 to about 1500 hours) of effective amounts (e.g., about 0.00001 mg/kg/hour to about 10 mg/kg/hour) of the load molecule or any other material associated with the biocompatible composition. It should be noted that the oligonucleotide-core carrier and the load molecule will have affinity for each other which can be defined by an affinity constant (Ka) or dissociation constant (Kd). This affinity can be adjusted by changing the length and amount of oligonucleotide moieties within the carrier. Since Kd or Ka represents an equilibrium constant, they define the amount of free load molecule at any given time. If the concentration of free load molecule decreases, due to utilization by the body, there will be automatic release of load molecule from the carrier to restore the equilibrium. The release rate will be determined by the speed of utilization of the free load molecule. The total capacity of the carrier will also determine the length of time the carrier can maintain a given concentration of free load molecule or therapeutic agent before it runs out of load molecule to release.

A variety of factors may affect the Kd of the load molecule to oligonucleotide-core carrier and thus the release rate. These include density of oligonucleotide moieties in the carrier, the length of oligonucleotide moieties, density of protective moieties in the carrier, size of protective chains in the carrier, the overall size of the oligonucleotide-core carrier, the environment around the oligonucleotide-carrier-load molecule complex, and rate of utilization or elimination of free load molecule by cells and organs of the body. The surrounding environmental conditions include temperature, polarity of the solvent which may be determined by ionic strength, protein and organic molecule concentrations, and osmolality. Proteins and organic molecules may also displace the load molecules from the carrier depending on the density of protective chains and the lengthy oligonucleotide moiety responsible for anchoring the load molecule.

To illustrate further, a wide range of dissociation rates may be obtained by adjusting the length of oligonucleotide moieties of the carrier or side chains of the polymers (spacer) while still maintaining sufficient biodegradability for the use intended for any such polymer. Such a result may be achieved by varying both the oligonucleotide groups and the protective groups of the polymer.

One protocol generally accepted in the field to determine the equilibrium constant of any load molecule in an aqueous environment, or other material, involves dissociation of the load molecule or other material in a PBS solution (50 mM $PO_4$, 150 mM NaCl, pH 7.4) at 37° C. For purposes of the present invention, the term "PBS protocol" is used herein to refer to such protocol.

In certain instances, the free load molecule concentration maintained by different oligonucleotide-core carriers of the present invention may be compared by subjecting them to such a protocol. In certain instances, it may be necessary to process several different oligonucleotide-core carriers in the same fashion to allow direct and relatively accurate comparisons of different oligonucleotide-core carriers to be made. Such comparisons may indicate that any one oligonucleotide-core carrier may maintain the active agent at a concentration of from about 2 nM or less to about 1000 nM or more, inclusive, than another oligonucleotide-core carrier. Alternatively, a comparison may reveal a concentration difference of about 3, 5, 7, 10, 25, 50, 100, 250, 500 or 750 nM. Even higher free load molecule concentration differences are contemplated by the present invention and Kd protocols.

In certain embodiments, the equilibrium constant may represent a mono- or bi-phasic system (or a two site-system, with two Kds). Release of load molecules may be characterized in certain instances by an initial increased release rate or high free load molecule concentration, which may release from about 5 to about 50% or more of the load molecule until that site with high Kd is depleted, or alternatively about 10, 15, 20, 25, 30 or 40%, followed by a much lower free load molecule concentration in which the site with low Kd is responsible.

The release rate of the load molecule may also be characterized by the amount of such material released per day per mg of carrier. For example, in certain embodiments, when the carrier is a polymer, the release rate may vary from about 1 ng or less of load molecule per day per mg of polymeric system to about 5000 or more ng/day/mg. Alternatively, the release rate may be about 10, 25, 50, 75, 100, 125, 150, 175, 200, 250, 300, 350, 400, 450, 500, 600, 700, 800 or 900 ng/day/mg. In still other embodiments, the release rate of the load molecule may be 20,000 ng/day/mg or even higher. In certain instances, active agents characterized by such release rate protocols may include therapeutic agents, antigens, diagnostics, targeting moieties and other substances.

a. In another aspect, the rate of release of the load molecule may be presented as the half-life of load molecule in the oligonucleotide-core carrier.

In addition to the embodiment involving protocols for in vitro determination of release rates, in vivo protocols, whereby in certain instances release rates of active agents from the carrier may be determined in vivo, are also contemplated by the present invention. Other assays useful for determining the release of load molecules from the carriers of the present invention may be envisioned.

Synthesis of the Compositions

The compositions of this invention may be synthesized using any one of the following methods. An example of a synthesis of an oligonucleotide-core carrier composition using poly lysine as a polymeric carrier, MPEG as a protective chain, and an oligonucleotide group is provided. This synthetic composition is especially suitable as an oligonucleotide-core carrier for oligonucleotide drugs, peptide/protein therapeutic agents, or contrast agents.

Scheme1:

The compositions may be prepared in two stages by first reacting a polyamino acid with activated MPEG analogs, and then reacting this reaction mixture with an activated oligonucleotide with or without spacer. This procedure is preferred when polylysine is used as the polymeric carrier.

Figure 4:
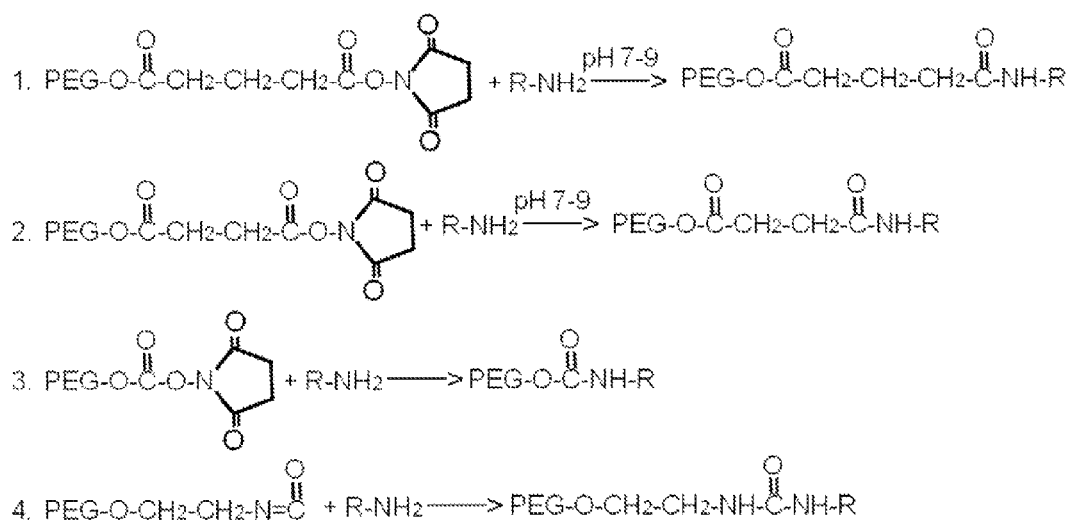
FIG. 4 depicts some of the chemical reactions that may be used to add PEG protective groups, analogs or derivatives thereof, to amino group containing carriers.
Figure 5:
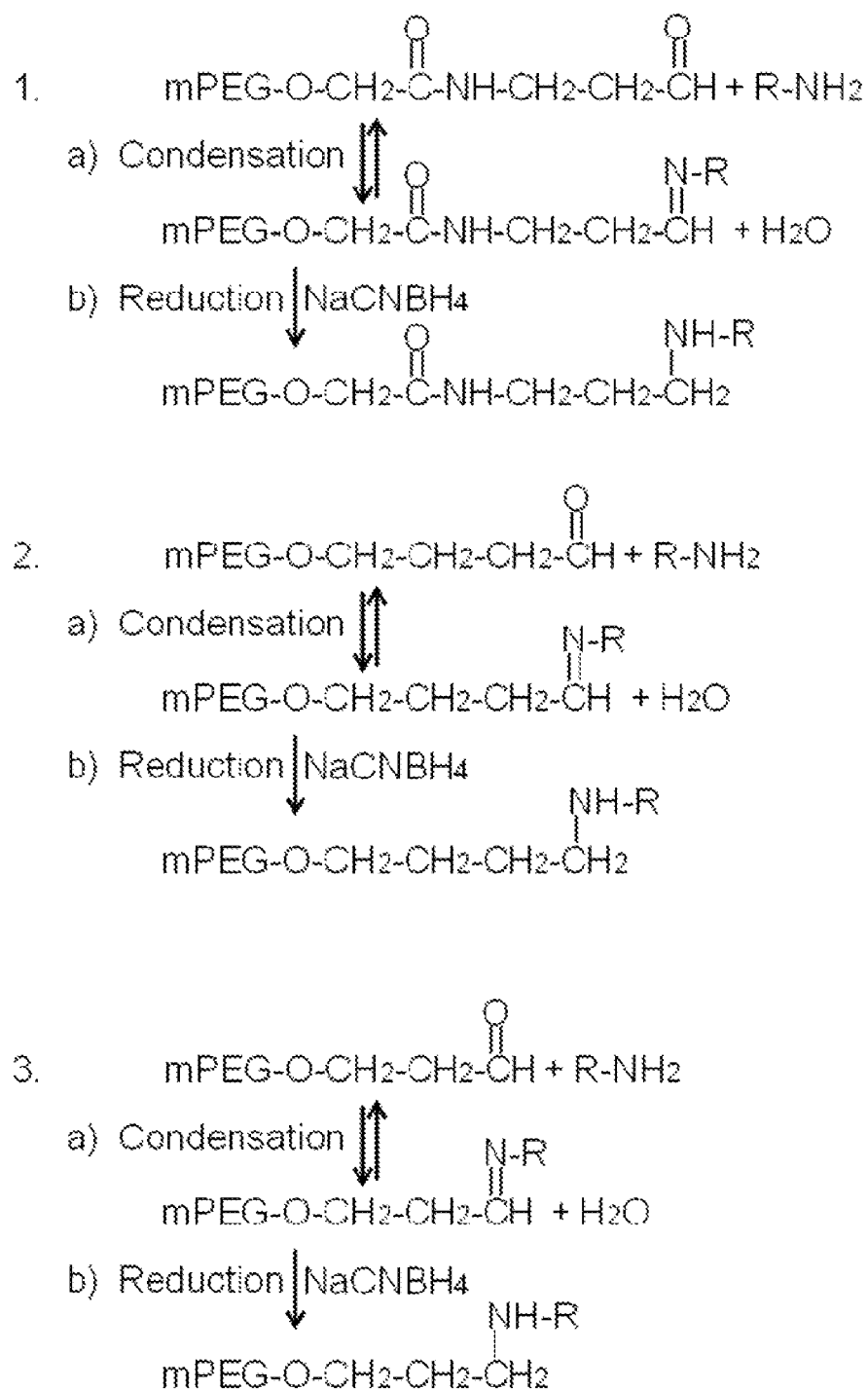
FIG. 5 depicts some of the chemical reactions that may be used to add aldehyde PEG derivatives to amino group containing carriers. These are two step condensation-reduction reactions (a & b).

Epsilon-amino groups of poly lysine are reacted with activated derivatives of carboxylated MPEG, e.g., acid chlorides, anhydrides, mixed anhydrides, nitrenes, isothiocyanates and imidazolides, and activated esters, e.g. N-hydroxysuccinimide, N-hydroxysulfosuccinimide, p-nitrophenyl, benzotriazolide. There are other ways of attaching PEGs, their analogs, or their derivatives to amino groups along the polymeric carrier as illustrated in FIG. 4, and FIG. 5, where R represent the carrier.

The oligonucleotide molecule is brought into reaction with the remaining amino groups, either in activated form, e.g., anhydride, mixed anhydride, or isothiocyanate, or in a non-activated form. If the carboxyl-containing oligonucleotide molecule is in the non-activated form, it can be activated in the presence of N-hydroxy-succinimide or N-hydroxy-sulfo-succinimide and carbodiimide to obtain an activated ester, and then brought into reaction with the remaining amino groups. The reaction may be preceded by an additional chemical modification of the polyamino acid backbone or MPEG chains which is not limited to reactions resulting in the formation or elimination of at least one chemical bond. There are other ways of attaching oligonucleotide groups, their analogs, or their derivatives to amino groups along the polymeric carrier. These ways are illustrated in FIG. 4 and FIG. 5, except that in this case PEG or mPEG will be the oligonucleotide groups and R remains a carrier.

The sequence of chemically linking the protective chains and a oligonucleotide group to a polymeric carrier may be reversed, i.e., linking the oligonucleotide groups first and then linking protective chain(s) to the polymeric carrier, but preferably, the oligonucleotide group is used as a mono-functional activated analog, i.e., one molecule of activated oligonucleotide group forms only one covalent linkage with a polymeric carrier.

Scheme 2:

The compositions also may be synthesized using standard peptide synthesis protocols with modified amino acid precursors such as MPEG-amino acid and oligonucleotide-amino acid. In this case, oligonucleotide groups and PEG may be alternated in a controllable manner.

Scheme 3:

Oligomers of PEG-polyamino acids may be conjugated with blocks of oligonucleotide-polyamino acids to form a block-co-polymer.

All three schemes will result in predictable compositions with highly predictable molecular weight distributions.

Linking MPEG to the polymeric carrier first prevents possible cross-linking of the poly-amino acid in the subsequent reaction. MPEG chains prevent the formation of by-products because they create a steric barrier against cross-linking the reagent. Therefore, the formation of high-molecular weight products can be controlled, which makes the synthetic steps predictable. As a result, a homogenous preparation is obtained with a narrow molecular weight distribution.

When carboxylated carriers are used, such as carboxylated saccharides, or polyaminoacids with carboxyl groups in their side chains, such as polyaspartic acid or polyglutamic acid, the polymeric carrier is preferably activated in the presence of carbodiimide and sulfosuccinimide, and then reacted with aminated protective chains and aminated oligonucleotide groups either simultaneously or in sequence, such as MPEG monoamine at pH 7-9 (FIG. 2).

Figure 6:
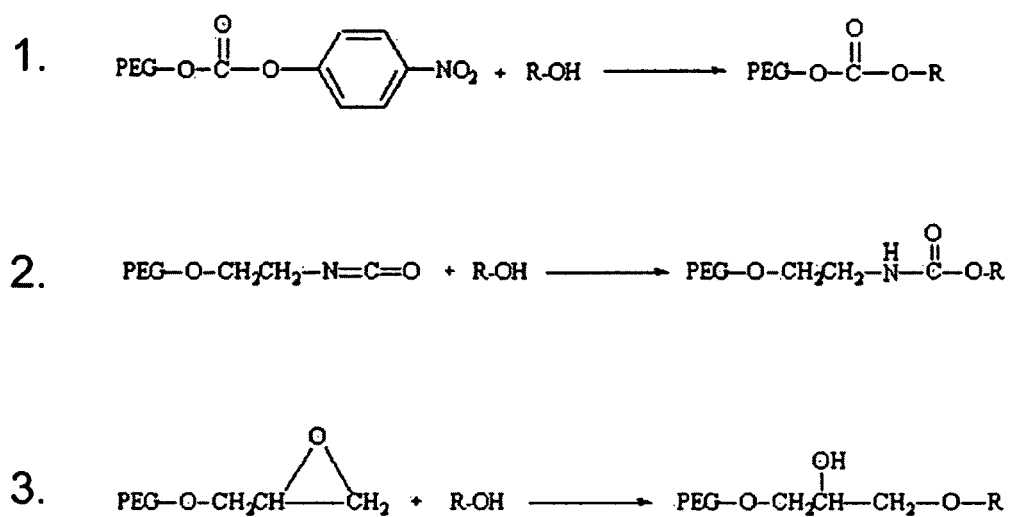
FIG. 6 depicts some of the chemical reactions that may be used to add PEG protective groups, analogs or derivatives thereof, to hydroxyl containing carriers.
Figure 7:
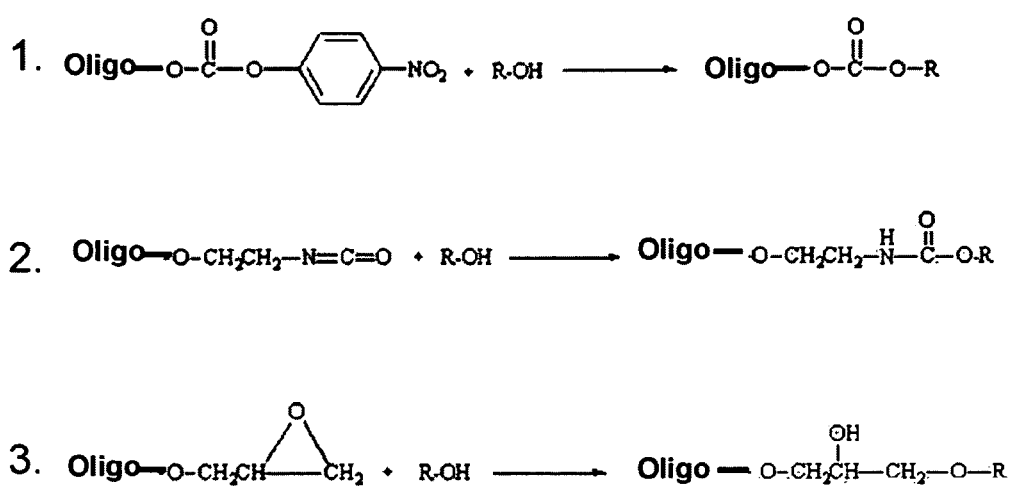
FIG. 7 depicts some of the chemical reactions that may be used to add oligonucleotide groups to hydroxyl containing carriers.

When hydroxylated carriers are used, such as polyserine or polythreonine, or any polymers with hydroxyl groups in their side chains, the protective groups, such as PEG, are preferably activated as illustrated in FIG. 6. Similarly the oligonucleotide groups are also preferably activated as illustrated in FIG. 7.

The polymeric carriers preferably contain peptide bonds. The same bonds are involved in conjugating an oligonucleotide molecule with reactive groups of the amino acid side chains. The compositions, therefore, are potentially biodegradable by various animal non-specific peptidases. To assist in vivo elimination of the polymeric carrier, protective chains, and oligonucleotide groups, elements of the polymeric carrier, protective chains, or oligonucleotide groups could be linked together by a semi-stable linkage, such as S—S bonds. Small amounts of trapped compositions may be removed from the body by degradation to smaller fragments. However, a variety of activated PEG derivatives may be used for the preparation of the compositions resulting in them ranging from virtually undegradable to labile. However, labile compositions are undesirable, since detaching MPEG will result in more extensive accumulation of the load molecule compositions in the reticuloendothelial system.

The protective chains of this invention do not activate the C3 component of complement. The C3 is a component of the complement pathways in the blood which upon activation will lead to a formation of membrane attack complex (MAC) that destroy cells by puncturing hole through the cell membrane. The complete description of these pathways is described in The Merk manual of diagnosis and therapy which is hereby incorporated by reference. This is the distinct advantage of polyethyleneglycol protective chains and their derivatives over previously known agents, e.g. dextran, which are known to activate the C3 component of complement. Similarly the oligonucleotide component of this composition is not likely to be immunoactive because of its small size and the fact that once they are exposed, they are also degraded quite rapidly. Protective chains prevent the exposure of large amounts of load molecules to receptor cells e.g., glomerulonephral phagocytes, capable of recognizing them if concentration is high enough. However, low concentrations will be recognized by high affinity receptors for the specific load molecule. Protective chains also form a steric barrier which prevents larger serum proteins from displacing the load molecules which would otherwise increase their release. The compositions of this invention also prevent possible toxicity resulting from high concentrations of free load molecules by preventing rapid accumulation of the load molecule in the liver and spleen. Without the load molecule, no expected acute toxicity of the oligonucleotide-core carrier compositions of this invention is expected since PEG is known to be non-toxic and the oligonucleotides are quite small and degraded quite rapidly once released or exposed.

Administration of the Oligonucleotide-Core Composition to the Patient

The oligonucleotide-core carrier composition containing load molecule can be administered to patients along with pharmaceutical excipients or diluents. Non-limiting examples of suitable pharmaceutical excipients or diluents include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol, buffered water, phosphate buffered saline and the like. These compositions can take the form of solutions, suspensions, tablets, pills, capsules, powders, sustained-release formulations and the like. In another preferred embodiment oligonucleotide core composition in any form could be further modulated using suitable, excipients and diluents including lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide even more sustained or delayed release of the load molecule or active ingredient from the carrier after administration to the patient. The compositions are preferably formulated in a unit dosage form, each dosage containing from about 1 to about 1000 mg of the oligonucleotide core composition containing 1 ug to 500 mg of load molecule or active ingredient. However, it will be understood that the therapeutic dosage administered will be determined by the physician in the light of the relevant circumstances including the clinical condition to be treated and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical diluents or excipients. These may be administered to humans, domestic pets, livestock, or other animals with a pharmaceutically acceptable diluents or excipients, in unit dosage form. Administration may be topical, parenteral, intravenous, intraarterial, subcutaneous, intramuscular, intracranial, intraorbital, ophthalmic, intraventricular, intracapsular, intraspinal, intracistemal, intraperitoneal, intranasal, aerosol, by suppositories, or oral administration. Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

The active therapeutic formulation of the invention can be provided in lyophilized form for reconstituting, for instance, in isotonic, aqueous, or saline buffers for parental, subcutaneous, intradermal, intramuscular or intravenous administration. The subject composition of the invention may also be administered to the patient in need of a therapeutic agent by liquid preparations for orifice, e.g. oral, nasal, sublingual, administration such as suspensions, syrups or elixirs. The subject composition of the invention may also be prepared for oral administration such as capsules, tablets, pills, and the like, as well as chewable solid formulations. The subject composition of the invention may also be prepared as a cream for dermal administration such as liquid, viscous liquid, paste, or powder. The subject composition of the invention may also be prepared as powder for deed lung administration with or without aerosolizing component.

Figure 8:
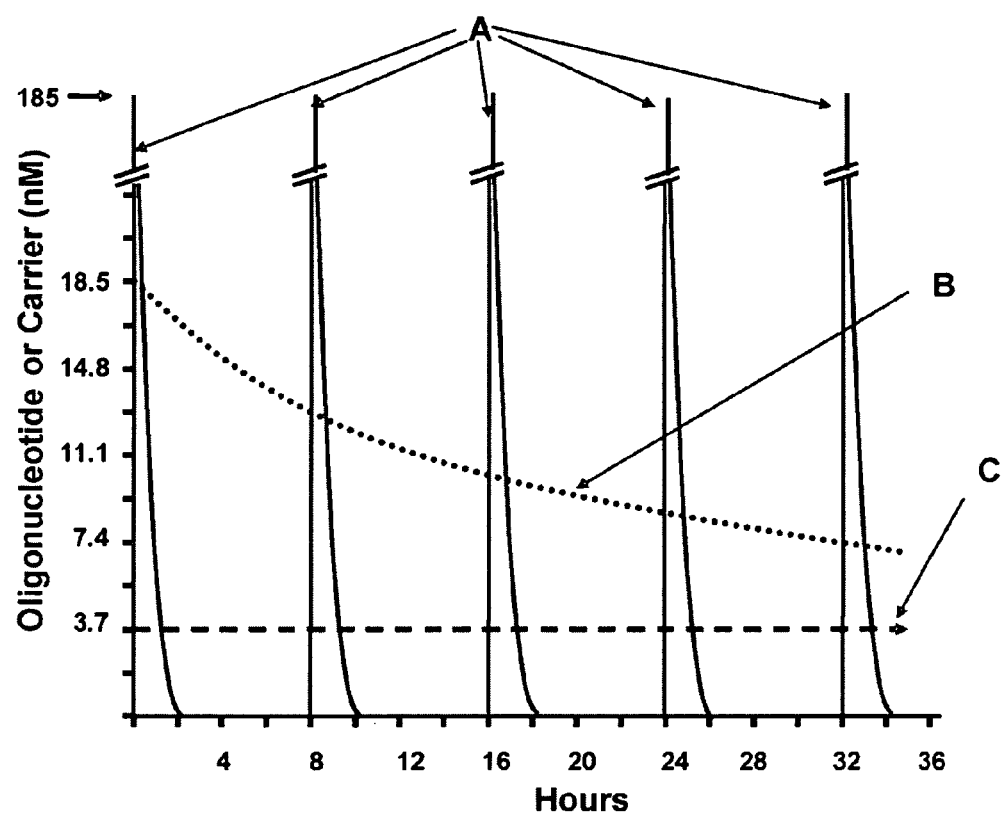
FIG. 8 is the hypothetical free oligonucleotide-containing load molecule in the blood with a natural half-life of 20 minutes. There is significant fluctuation in the concentration of free oligonucleotide-containing load molecule without the oligonucleotide-carrier. With the carrier, the free oligonucleotide-containing load molecule will be maintained at therapeutic concentration. The nM concentration of oligonucleotide-carrier decreases with a half-life of 20 hrs. A) Oligonucleotide-containing load molecule level resulting from injection 5 mg/kg, 3 times a day without a Oligonucleotide-carrier of the instant invention, this load molecule has a blood half-life of 20 minutes; B) oligonucleotide-carrier loaded with load molecule has a half-life of 20 hours; C) therapeutic level of free load molecule maintained by oligonucleotide-carrier.

The presently disclosed compositions are design to deliver active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems as well as being able to traverse the blood-brain barrier. Administration of an active agent bound to oligonucleotide-core carrier composition of the present invention results in an increased bioavailability of the active agent compared to administration of the active agent alone, as shown in hypothetical scenario in FIG. 8. One of the embodiments of the present invention is an oligonucleotide carrier that is expected to have a half-life of 20 hours and to accumulate at sites with increased vascular permeability. This is based on previous study of nanocarrier with similar size protected by poly(ethylene glycol). Such embodiment will be ideal in prolonging the exposure of the body to load molecules with very short biological half-life as illustrated in FIG. 8. This, therefore result in increase bioavailability.

Preferred Compositions of the Invention

The invention also features a composition having polyamino acid carrier with the formula:

$$[[-\overset{O}{\underset{\|}{C}}-NH-\underset{R_1}{\overset{|}{CH}}-]\ [-\overset{O}{\underset{\|}{C}}-NH-\underset{R_2}{\overset{|}{CH}}-]]_k$$

wherein the groups can be linked in any order, e.g., the oligonucleotide group $R_1$ unit can be repeated several times in the chain before a protective chain containing group $R_2$ unit occurs, and vice versa, wherein k is 50-560;

The oligonucleotide group $R_1$ is selected from a group comprising but not limited to:

a) a modified lysine R group ($-(CH_2)_4NH-$) with an oligonucleotide molecule covalently attached by a spacer to the epsilon amino group of lysine (in bold below) with the formula:

$-(CH_2)_4NH$-(Spacer)-(Ymer), where,

Y is integer from 2-100 representing the number of nucleotide or mer; and Spacer is any chain of atoms that provides covalent linking and space of 2-50 Angstroms distance between the oligonucleotide and the epsilon aminogroup of lysine side chain.

b) a modified aspartate R group [$-CH_2CO-$] with an oligonucleotide molecule covalently attached by a spacer to the carbonyl group of aspartate (in bold below) with the formula:

$-CH_2CO$-(Spacer)-(Ymer), where,

Y is integer from 2-100 representing the number of nucleotide or mer; and Spacer is any chain of atoms that provides covalent link and space of 2-50 Angstroms distance between the oligonucleotide and the carbonyl group of aspartate side chain.

c) a modified glutamate R group [$-(CH_2)_2CO-$] with an oligonucleotide molecule covalently attached by a spacer to the carbonyl group of glutamate (in bold below) with the formula:

$-(CH_2)_2CO$-(Spacer)-(Ymer), where,

Y is integer from 2-100 representing the number of nucleotide or mer; and Spacer is any chain of atoms that provides covalent link and space of 2-50 Angstroms distance between the oligonucleotide and the carbonyl group of glutamate side chain.

d) a modified serine R group [$-CH_2O-$] with an oligonucleotide molecule covalently attached by a spacer to the hydroxyl group of serine (in bold below) with the formula:

$-CH_2O$-(spacer)-(Ymer), where,

Y is integer from 2-100 representing the number of nucleotide or mer; and Spacer is any chain of atoms that provides covalent link and space of 2-50 Angstroms distance between the oligonucleotide and the hydroxyl group of serine side chain.

e) a modified threonine R group [$-CH_2[CH_3]O-$] with an oligonucleotide molecule covalently attached by a spacer to the hydroxyl group of threonine (in bold below) with the formula:

$-CH_2[CH_3]O$-(Spacer)-(Ymer), where,

Y is integer from 2-100 representing the number of nucleotide or mer; and Spacer is any chain of atoms that provides covalent link and space of 2-50 Angstroms distance between the oligonucleotide and the hydroxyl group of threonine side chain.

f) a modified tyrosine R group [$-(C_6H_4)O-$] with an oligonucleotide molecule covalently attached by a spacer to the hydroxyl group of tyrosine (in bold below) with the formula:

$-(C_6H_4)O$-(Spacer)-(Ymer), where,

Y is integer from 2-100 representing the number of nucleotide or mer; and Spacer is any chain of atoms that provides covalent link and space of 2-50 Angstroms distance between the oligonucleotide and the hydroxyl group of tyrosine side chain.

The protective chain containing group $R_2$ is selected from a group comprising but not limited to:

a) a modified lysine R group [$-(CH_2)_4NH-$] with protective chain with or without an oligonucleotide group covalently linked by a spacer to the epsilon amino group of lysine (in bold below) with the formula:

—(CH$_2$)$_4$NH-(Spacer)-(Ymer)-(Spacer)-A-B—OR$_3$,
or

—(CH$_2$)$_4$NH-(Spacer)-A-B—OR$_3$,

Where,

Y is integer from 2-100 representing the number of nucleotides or mer;

R$_3$ is H, (CH$_2$)$_p$CH$_3$ or (CH$_2$)$_p$COOH, p is 0-7;

A is a protective group [OCH$_2$CH$_2$]$_x$ and B is a protective group selected from [OCH$_2$CH$_2$]$_z$ or [OCHCH$_3$CH$_2$]$_z$, where x+z is 17-250, or -A-B— is various combinations of [OCH$_2$CH$_2$], [OCH$_2$CH$_2$], and/or [OCHCH$_3$CH$_2$] with total of 17-250 units;

Spacer is any linear chain of atoms that provides covalent link and space of 3-50 Angstroms distance between the oligonucleotide and the protective group and/or the oligonucleotide and the carbonyl group of glutamate side chain or between protective group A and the carbonyl group of glutamate side chain.

b) a modified aspartate R group [—CH$_2$CO—] with protective chain with or without an oligonucleotide group covalently linked by a spacer to the carbonyl group of aspartate (in bold below) with the formula:

—CH$_2$CO-(Spacer)-(Ymer)-(Spacer)-A-B—OR$_3$,or

—CH$_2$CO-(Spacer)-A-B—OR$_3$,

Where,

Y is integer from 2-100 representing the number of nucleotides or mer;

R$_3$ is H, (CH$_2$)$_p$CH$_3$ or (CH$_2$)$_p$COOH, p is 0-7;

A is a protective group [OCH$_2$CH$_2$]$_x$ and B is a protective group selected from [OCH$_2$CH$_2$]$_z$ or [OCHCH$_3$CH$_2$]$_z$, where x+z is 17-250, or -A-B— is various combinations of [OCH$_2$CH$_2$], [OCH$_2$CH$_2$], and/or [OCHCH$_3$CH$_2$] with total of 17-250 units;

Spacer is any linear chain of atoms that provides covalent link and space of 3-50 Angstroms distance between the oligonucleotide and the protective group and/or the oligonucleotide and the carbonyl group of aspartate side chain or between protective group A and the carbonyl group of aspartate side chain.

c) a modified glutamate R group [—(CH$_2$)$_2$CO—] with protective chain with or without an oligonucleotide group covalently linked by a spacer to the carbonyl group of glutamate (in bold below) with the formula:

—(CH$_2$)$_2$CO-(Spacer)-(Ymer)-(Spacer)-A-B—OR$_3$,
or

—(CH$_2$)$_2$CO-(Spacer)-A-B—OR$_3$,

Where,

Y is integer from 2-100 representing the number of nucleotides or mer;

R$_3$ is H, (CH$_2$)$_p$CH$_3$ or (CH$_2$)$_p$COOH, p is 0-7;

A is a protective group [OCH$_2$CH$_2$]$_x$ and B is a protective group selected from [OCH$_2$CH$_2$]$_z$ or [OCHCH$_3$CH$_2$]$_z$, where x+z is 17-250, or -A-B— is various combinations of [OCH$_2$CH$_2$], [OCH$_2$CH$_2$] and/or [OCHCH$_3$CH$_2$] with total of 17-250 units;

Spacer is any linear chain of atoms that provides covalent link and space of 3-50 Angstroms distance between the oligonucleotide and the protective group and/or the oligonucleotide and the carbonyl group of glutamate side chain or between protective group A and the carbonyl group of glutamate side chain.

d) a modified serine R group [—CH$_2$O—] with protective chain with or without an oligonucleotide group covalently linked by a spacer to the hydroxyl group of serine (in bold below) with the formula:

—CH$_2$O-(Spacer)-(Ymer)-(Spacer)-A-B—OR$_3$,or

—CH$_2$O-(Spacer)-A-B—OR$_3$,

Where,

Y is integer from 2-100 representing the number of nucleotides or mer;

R$_3$ is H, (CH$_2$)$_p$CH$_3$ or (CH$_2$)$_p$COOH, p is 0-7;

A is a protective group [OCH$_2$CH$_2$]$_x$ and B is a protective group selected from [OCH$_2$CH$_2$]$_z$ or [OCHCH$_3$CH$_2$]$_z$, where x+z is 17-250, or -A-B— is various combinations of [OCH$_2$CH$_2$], [OCH$_2$CH$_2$] and/or [OCHCH$_3$CH$_2$] with total of 17-250 units;

Spacer is any linear chain of atoms that provides covalent link and space of 3-50 Angstroms distance between the oligonucleotide and the protective group and/or the oligonucleotide and the hydroxyl group of serine side chain or between protective group A and the hydroxyl group of serine side chain.

e) a modified threonine R group [—CH$_2$[CH$_3$]O—] with protective chain with or without an oligonucleotide group covalently linked by a spacer to the hydroxyl group of threonine (in bold below) with the formula:

—CH(CH$_3$)O-(Spacer)-(Ymer)-(Spacer)-A-B—OR$_3$,
or

—CH(CH$_3$)O-(Spacer)-A-B—OR$_3$,

Where,

Y is integer from 2-100 representing the number of nucleotides or mer;

R$_3$ is H, (CH$_2$)$_p$CH$_3$ or (CH$_2$)$_p$COOH, p is 0-7;

A is a protective group [OCH$_2$CH$_2$]$_x$ and B is a protective group selected from [OCH$_2$CH$_2$]$_z$ or [OCHCH$_3$CH$_2$]$_z$, where x+z is 17-250, or -A-B— is various combinations of [OCH$_2$CH$_2$], [OCH$_2$CH$_2$], and/or [OCHCH$_3$CH$_2$] with total of 17-250 units;

Spacer is any linear chain of atoms that provides covalent link and space of 3-50 Angstroms distance between the oligonucleotide and the protective group and/or the oligonucleotide and the hydroxyl group of threonine side chain or between protective group A and the hydroxyl group of threonine side chain.

f) a modified tyrosine R group [—(C$_6$H$_4$)O—] with protective chain with or without an oligonucleotide group covalently linked by a spacer to the hydroxyl group of tyrosine (in bold below) with the formula:

—(C$_6$H$_4$)O-(Spacer)-(Ymer)-(Spacer)-A-B—OR$_3$,or

—(C$_6$H$_4$)O-(Spacer)-A-B—OR$_3$,wherein:

Where,

Y is integer from 2-100 representing the number of nucleotides or mer;

R$_3$ is H, (CH$_2$)$_p$CH$_3$ or (CH$_2$)$_p$COOH, p is 0-7;

A is a protective group [OCH$_2$CH$_2$]$_x$ and B is a protective group selected from [OCH$_2$CH$_2$]$_z$ or [OCHCH$_3$CH$_2$]$_z$, where x+z is 17-250, or -A-B— is various combinations of [OCH$_2$CH$_2$], [OCH$_2$CH$_2$], and/or [OCHCH$_3$CH$_2$] with total of 17-250 units;

Spacer is any linear chain of atoms that provides covalent link and space of 3-50 Angstroms distance between the oligonucleotide and the protective group and/or the oligonucleotide and the hydroxyl group of tyrosine side chain or between protective group A and the hydroxyl group of tyrosine side chain.

It is also the object of the present invention that the composition may only have $R_2$, with none or very few $R_1$ especially when $R_2$ already contains the oligonucleotide groups flanking the carrier and protective groups. The subject of the invention also features a composition having polyamino acid carrier with the formula:

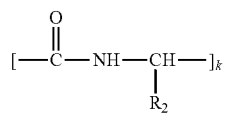

wherein k is 50-560 and $R_2$ represents an oligonucleotide groups with protective groups with the formula:

-(Spacer)-(Ymer)-(Spacer)-A-B—$OR_3$, wherein;

Y is integer from 2-100 representing the number of nucleotides or mer;

$R_3$ is H, $(CH_2)_p CH_3$ or $(CH_2)_p COOH$, p is 0-7;

A is a protective group $[OCH_2CH_2]_x$ and B is a protective group selected from $[OCH_2CH_2]_z$ or $[OCHCH_3CH_2]_z$, where x+z is 17-250, or -A-B— is various combinations of $[OCH_2CH_2]$, $[OCH_2CH_2]$ and/or $[OCHCH_3CH_2]$ with total of 17-250 units;

Spacer is any linear chain of atoms that provides covalent link and space of 3-50 Angstroms distance between the oligonucleotide and the protective group and/or the oligonucleotide and the carrier.

Non-Immunogenicity

Prevention of the non-target cell surface from exposure to high concentrations of load molecules is accomplished by using load molecules with high binding affinities to the oligonucleotide core, resulting in only nanomolar to picomolar concentrations of free load molecule at any given moment. In addition, the PEG protecting groups will protect the concentrated bound load molecule from being in contact with the cell surface. This will prevent stimulation of immune response which occurs at much higher concentrations of free antigen (microgram to milligram/ml). Because of PEG protection, there is no binding of the oligonucleotide-core carrier with cells capable of opsonin recognition, e.g., antigen presenting phagocytes, or with immunocompetent antigen presenting phagocytes, or with immunocompetent blood cells, e.g., resting B-cells. As a result, an immune response to the load molecule itself is less likely and the production of host antibodies to the load molecule can be avoided. This allows the repetitious use of the composition if necessary.

The combination of long-blood half-life and lack of immunogenicity is an important feature of this invention.

Dosages

The dosage of any compound of the present invention will vary depending on the symptoms, age and body weight of the patient, the nature and severity of the disorder to be treated or prevented, the route of administration, and the form of the supplement. Any of the subject formulations may be administered in a single dose or in divided doses. Dosages for the compounds of the present invention may be readily determined by techniques known to those of skill in the art or as taught herein. Also, the present invention contemplates mixtures of more than one subject compound, as well as other therapeutic agents.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular load molecule of the present invention. This may be accomplished by routine experiment as described herein, using one or more groups of animals (preferably at least 5 animals per group), or in human trials if appropriate. The effectiveness of any compound and method of treatment or prevention may be assessed by administering the supplement and assessing the effect of the administration by measuring one or more indices associated with the neoplasm of interest, and comparing the post-treatment values of these indices to the values of the same indices prior to treatment.

The precise time of administration and amount of any particular compound that will yield the most effective treatment in a given patient will depend upon the activity, pharmacokinetcs, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several compounds of the present invention, or alternatively other chemotherapeutic agents, may reduce the required dosage for any individual component because the onset and duration of effect of the different components may be complimentary. In such combined therapy, the different active agents may be delivered together or separately, and simultaneously or at different times within the day.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. Although compounds that exhibit toxic side effects may be used, care should be taken to design a delivery system that targets the compounds to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the $ED_{50}$, with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography (HPLC).

Formulations

The oligonucleotide core carrier compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. The oligonucleotide-core composition with specific load molecule can also be administered into deep long by aerosolizing the composition into 1-5 um particle using standard techniques known in the art either with or without addition of aerosolizing excipient. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject oligonucleotide carrier compositions may be suitable for oral, nasal, topical (including buccal and sublingual), rectal, vaginal, aerosol and/or parenteral administration. The formulations of oligonucleotide carrier compositions may conveniently be presented in unit dosage form and may be prepared by any methods well known in the art of pharmacy. The amounts of composition that may be combined with other excipients to produce a single dose may vary depending upon the subject being treated, and the particular mode of administration.

Methods of preparing these oligonucleotide-core carrier-load molecule formulations include the step of bringing into association oligonucleotide-core carrier of the present invention with the load molecule and, optionally, one or more accessory ingredients. In general, the formulations are prepared by uniformly and intimately bringing into association load molecules with oligonucleotide carriers, or finely divided solid oligonucleotide-core carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject oligonucleotide carrier-load molecule composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethyl cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the oligonucleotide carrier-load molecule compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. The liquid dosage oligonucleotide carrier-load molecule formulation may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspension dosage of oligonucleotide carrier-load molecule formulation may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Oligonucleotide carrier-load molecule formulations for rectal or vaginal administration may be presented as a suppository, which may be prepared by mixing a load molecule with one or more suitable oligonucleotide carriers and other excipients comprising, for example, cocoa butter, polyethylene glycol, a suppository wax or a salicylate, and which is solid at room temperature, but liquid at body temperature and, therefore, will melt in the body cavity and release the oligonucleotide carrier with load molecule. Formulations which are suitable for vaginal administration also include pessaries, tampons, creams, gels, pastes, foams or spray formulations containing excipients as are known in the art to be appropriate.

Oligonucleotide carrier-load molecule dosage formulations for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffin, starch, tragacanth, cellulose derivatives, polyethylene glycols, silicones, bentonite, silicic acid, talc and zinc oxide, or mixtures thereof. Oligonucleotide carrier-load molecule compositions of the present invention may also be in the form of baby wipes.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Oligonucleotide carrier-load molecule compositions of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

EXEMPLIFICATION

Synthetic Method Overview

Oligonucleotide-core carriers of the present invention include a central carrier chain, an oligonucleotide group, a protecting group, and, optionally, a targeting group. Each group is linked together covalently and the oligonucleotide group is capable of forming reversible binding (hydrogen bonding) with complementary oligonucleotide-containing load molecule such as organic molecule, oligosaccharide, peptide, protein, DNA, and RNA therapeutic or diagnostic agent. The reversible linkage between the oligonucleotide-core carrier and a load molecule includes hydrogen bondings between the oligonucleotide of the load molecule and the complementary oligonucleotide of the carrier.

The synthesis of a oligonucleotide-core carrier load molecule complex from a polymeric carrier containing amino, carboxyl, hydroxyl groups, or thiol groups generally involves three synthetic stages: 1) covalent modification of a back bone carrier with protective chains; 2) modification of the product from step 1) with oligonucleotide groups; and 3) incubating the product from step 2) with a load molecule, such as, for example, incubation with siRNA to achieve formation of a oligonucleotide-core carrier-siRNA complex.

EXAMPLE 1

Synthesis of MPEG-Poly-L-Lysine (5000: 40,000: 73%) (40PLPEG573)

Figure 9:
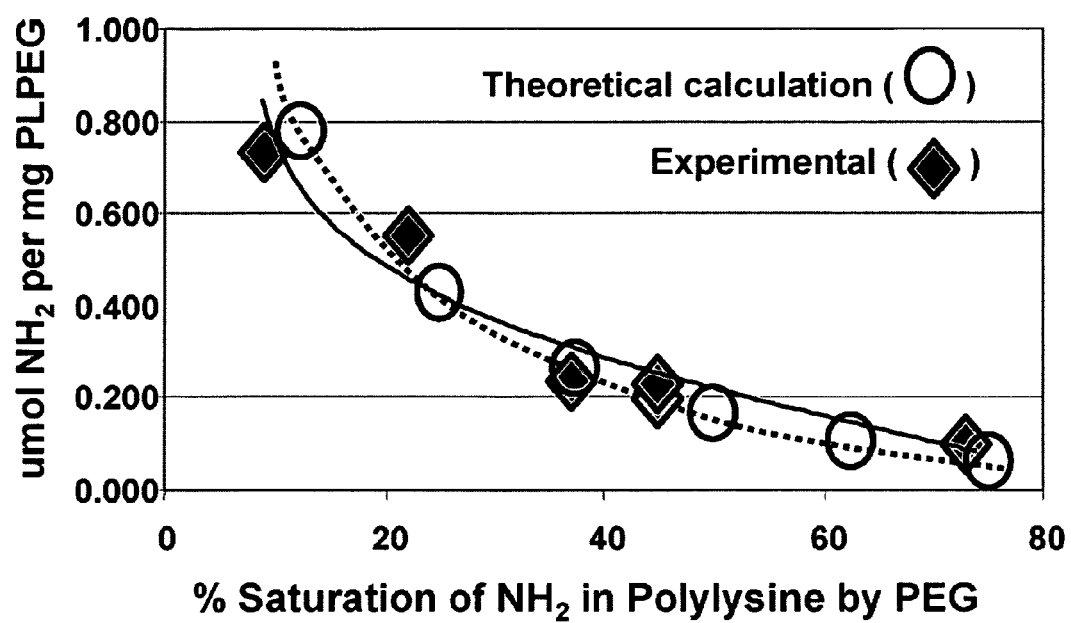
FIG. 9 is a graph showing the theoretical and actual relationship between the amount of amino-group/mg of PLPEG (polylysine-polyethyleneglycol copolymer) and % amino-group saturation of polylysine. This is very useful as secondary confirmation of the composition of PLPEG. This PEGylation process is quite reproducible and adjustable during synthesis by continuing the reaction until the desired % PEGylation is achieved using TNBS amino group assay as a feedback guide during the reaction. The yield is about 50-80% (5-8 gr) of the starting materials. The theoretical prediction was calculated using the following equation: $X=[100\times(C-Y)]/5YC+C]$; where X is the % saturation; Y is the mmol $NH_2$ per gram of PLPEG as determined by TNBS; C is the mmol of $NH_2$ per gram of PL (polylysine) as determined by TNBS. The 5 in the term 5YC in the equation represent the size of PEG used which in this case is 5 kDa, thus 5YC. If 10 kDa PEG is used, this will be 10YC. This is useful because once PLPEG product is formed, the percent saturation of the amino group of polylysine can be determined by a single TNBS assay of the final product to determine Y from which X can be calculated.
Figure 10:
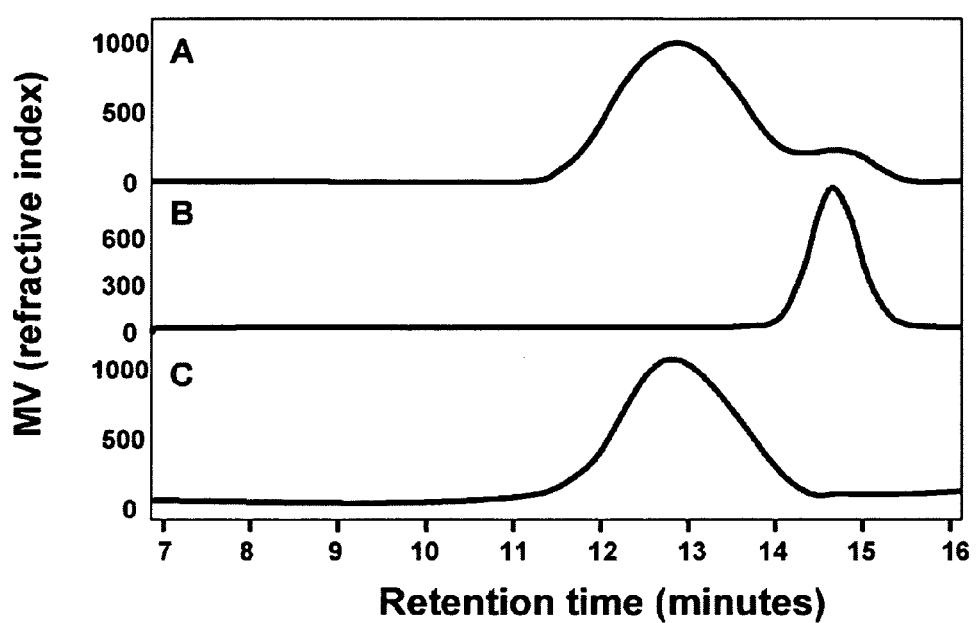
FIG. 10. These are Gel Filtration Chromatograms of the products of the reaction before and after clean up through 100 kDa MWCO membrane (Amersham Biosciences, Needham, Mass.) showing that all unreacted PEG had been removed. The column used was Ultrahydrogel linear (0.78×30 cm, Waters) eluted at flow rate of 0.6 ml/min PBS. The materials were detected using refractive index detector. Panel A is 20PLPEG5-55 (20 kDa polylysine where 55% of the amino groups were reacted with PEG succinate of 5 kDa molecular weight) prior to clean-up from unreacted 5 kDa PEG. Panel B is 5 kDa PEG alone. Panel C is 20PLPEG5-55 after clean up.

The reagents, MPEG-succinimidyl-succinate and polylysine, are commercially available and their syntheses are well known in the art. Poly-L-lysine (200 mg; Polylysine Hydrobromide; Sigma chemical Co.; DPvis: 264; MWvis: 55,200; DPmalls: 190; MWmalls: 39,800; 0.7 mmoles aminogroup by TNBS assay Sparado et al. Anal Biochem 96:317, 1979) was dissolved in 10 ml of 0.1 M carbonate buffer pH 8.35 and 1150 mg of MPEG-succinimidyl-succinate was added, vortexed, and incubated overnight at room temperature. The next day, aliquots were taken and the amount of amino groups remaining was quantified using trinitrobenzenesulfonic acid (Sparado et al. Anal Biochem 96:317, 1979). The result indicated that 73% of amino group had been conjugated to MPEG. To cap the carboxyl terminal of polylysine that can potentially interfere with the next reaction (addition of oligonucleotide group), 600 ul of ethylenediamine and 100 mg EDC was added mixed and incubated at room temperature for 1 hr. The solution (200 ml) was washed by filtration through 100 kDa cut-off filter membrane (Amersham Biosciences Corp, Westborough, Mass.) with five changes of water. The resulting PLPEG complex was lyophilized and weighed giving a yield of 860 mg. The resulting product has an estimated Mw of 730 kDa based on the number of amino groups that had been derivatized by MPEG. The number of free amino groups per mg of final product is 0.43 umole/mg (FIG. 9). It should be noted that if MPEG-succinimidyl-succinate used is contaminated with free succinate, which is quite common, the amount of PEG will be less than what is expected from the amino group analysis and will be inconsistent with the amount of amino group per mg of final product.

EXAMPLE 2

Synthesis of MPEG-Poly-L-Lysine (5 kDa PEG: 40 kDa PL: 55% Saturation of Amino Groups) (40PLPEG555)

The reagents, MPEG-succinimidyl-succinate and polylysine, are commercially available and their syntheses are well known in the art. Poly-L-lysine (200 mg; Polylysine Hydrobromide; Sigma chemical Co.; DPvis: 264; MVWis: 55,200; DPmalls: 190; MWmalls: 39,800; 0.7 mmoles aminogroup by TNBS assay Sparado et al. Anal Biochem 96:317, 1979) was dissolved in 10 ml of 0.1 M carbonate buffer pH 8.35 and 900 mg of MPEG-succinimidyl-succinate was added, vortexed, and incubated overnight at room temperature. The next day, aliquots were taken and the amount of amino groups remaining was quantified using trinitrobenzenesulfonic acid (Sparado et al. Anal Biochem 96:317, 1979). The result indicated that 55% of the amino groups had been conjugated to MPEG. To cap the carboxyl terminal of polylysine that can potentially interfere with the next reaction (addition of oligonucleotide group), 600 ul of ethylenediamine and 100 mg EDC was added mixed and incubated at room temperature for 1 hr. The solution (200 ml) was washed by filtration through 100 kDa cut-off filter membrane (Amersham Biosciences Corp, Westborough, Mass.) with five changes of water. The resulting PLPEG complex was lyophilized and weighed giving a yield of 860 mg. The resulting product has an estimated Mw of 560 kDa based on the number of amino groups that had been derivatized by MPEG. The number of free amino groups per mg of final product is 0.795 umole/mg (FIG. 9). It should be noted that if MPEG-succinimidyl-succinate used is contaminated with free succinimidyl-succinate, the amount of PEG will be less than what is expected from the amino group analysis and will be inconsistent with the amount of amino group per mg of final product.

EXAMPLE 3

Synthesis of MPEG-Poly-1-Lysine (5 kDa PEG: 40 kDa PL: 22% Saturation of Amino Groups) (40PLPEG522)

The reagents, MPEG-succinimidyl-succinate and polylysine, are commercially available and their syntheses are well known in the art. Poly-L-lysine (200 mg; Polylysine Hydrobromide; Sigma chemical Co.; DPvis: 264; MVWis: 55,200; DPmalls: 190; MWmalls: 39,800; 0.7 mmoles aminogroup by TNBS assay Sparado et al. Anal Biochem 96:317, 1979) was dissolved in 10 ml of 0.1 M carbonate buffer pH 8.35 and 600 mg of MPEG-succinimidyl-succinate was added, vortexed, and incubated overnight at room temperature. The next day, aliquots were taken and the amount of amino groups remaining was quantified using trinitrobenzenesulfonic acid (Sparado et al. Anal Biochem 96:317, 1979). The result indicated that 22% of amino groups had been conjugated to MPEG. To cap the carboxyl terminal of polylysine that can potentially interfere with the next reaction (addition of oligonucleotide group), 600 ul of ethylenediamine and 100 mg EDC was added mixed and incubated at room temperature for 1 hr. The solution (200 ml) was washed by filtration through 100 kDa cut-off filter membrane (Amersham Biosciences Corp, Westborough, Mass.) with five changes of water. The resulting PLPEG complex was lyophilized and weighed giving a yield of 320 mg. The resulting product has an estimated Mw of 250 kDa based on the number of amino groups that had been derivatized by MPEG. The number of free amino groups per mg of final product is 1.14 umole/mg (FIG. 9). It should be noted that if MPEG-succinimidyl-succinate used is contaminated with free succinimidyl-succinate, the amount of PEG will be less than what is expected from the amino group analysis and will be inconsistent with the amount of amino group per mg of final product.

EXAMPLE 4

Synthesis of MPEG-Poly-1-Lysine (5 Kda PEG: 40 kDa PL: 9% Saturation of Amino Groups) (40PLPEG509)

The reagents, MPEG-succinimidyl-succinate and polylysine, are commercially available and their syntheses are well known in the art. Poly-L-lysine (200 mg; Polylysine Hydrobromide; Sigma chemical Co.; DPvis: 264; MVWis: 55,200; DPmalls: 190; MWmalls: 39,800; 0.7 mmoles aminogroup by TNBS assay Sparado et al. Anal Biochem 96:317, 1979) was dissolved in 10 ml of 0.1 M carbonate buffer pH 8.35 and 300 mg of MPEG-succinimidyl-succinate was added, vortexed, and incubated overnight at room temperature. The next day, aliquots were taken and the amount of amino group remaining was quantified using trinitrobenzenesulfonic acid (TNBS) (Sparado et al. Anal Biochem 96:317, 1979). The result indicated that 9% of amino groups had been conjugated to MPEG. To cap the carboxyl terminal of polylysine that can potentially interfere with the next reaction (addition of oligonucleotide group), 600 ul of ethylenediamine and 100 mg EDC was added mixed and incubated at room temperature for 1 hr. The solution (200 ml) was washed by filtration through 100 kDa cut-off filter membrane (Amersham Biosciences Corp, Westborough, Mass.) with five changes of water. The resulting PLPEG complex was lyophilized and weighed giving a yield of 300 mg. The resulting product has an estimated Mw of 125 kDa based on the number of amino groups that had been derivatized by MPEG. The number of free amino groups per mg of final product is 1.5 umole/mg (FIG. 9). It should be noted that if MPEG-succinimidyl-succinate used is contaminated with free succinimidyl-succinate, the amount of PEG will be less than what is expected from the amino group analysis and will be inconsistent with the amount of amino group per mg of final product.

EXAMPLE 5

Preparation of 5' Carboxyl Oligonucleotide 5 nanomoles of phosphorylated oligonucleotide will be dissolved in an aqueous solution containing tenth molar imidazole and tenth molar EDAC (100 microliter, pH 6.0) and will be left 20 to 50 degrees centigrade for 1 to 16 hours. The contents will be passed through a gel filtration column and to the oligonucleotide containing fractions an equal volume of four tenth molar of amino caproic acid spacer/linker will be added. After 1-16 hours the carboxylated oligonucleotide can be isolated by gel filtration.

EXAMPLE 6

Preparation of 5' Amino Oligonucleotide

To a ml of solution containing 5' phosphorylated oligonucleotide, sixteen microliters of N-methyl imidazole and one mL one fourth molar of diaminohexane spacer/linker along with 4 mg EDAC will be added, the pH of the solution will be adjusted to about 6. After an overnight reaction 5' amino oligonucleotide will be isolated by gel filtration.

EXAMPLE 7

Preparation of Carrier with Ester Linked Oligonucleotide

To a ml. of aqueous solution containing 5 nanomoles each of 5' hydroxyl oligonucleotide and carboxyl containing carrier (with or without protective chain with 5 nanomoles equivalent of carboxyl) or 5' carboxyl oligonucleotide and hydroxyl containing carrier (with or without protective chain with 5 nanomoles equivalent of hydroxyl), 5 nmol of NHSS (optional) and 10 mg. of EDAC will be added. The solutions will be left at room temperature overnight after adjusting the pH to 6. The oligonucleotide-containing carrier will isolated by chromatography using beads of dextran gel cross-linked with bisacrylamide having an exclusion volume of about 80,000 Daltons for dextran (SEPHACRYL S-100, Pharmacia, Inc., Piscataway, N.J.). The oligonucleotide-containing carrier will be at the void volume.

EXAMPLE 8

Preparation of Carrier with Amide Linked Oligonucleotide

To a ml. of aqueous solution containing 5 nanomoles of each 5' amino oligonucleotide and carboxyl containing carrier (with or without protective chains with 5 nanomoles equivalent of carboxyl) or 5' carboxyl oligonucleotide and amino containing carrier (with or without protective chain with 5 nanomoles equivalent of amino group), 5 nmol of NHSS (optional) and 10 mg. of EDAC will be added. The solutions will be left at room temperature overnight after adjusting the pH to 6. The oligonucleotide-containing carrier will isolated by chromatography using beads of dextran gel cross-linked with bisacrylamide having an exclusion volume of about 80,000 Daltons for dextran (SEPHACRYL S100, Pharmacia, Inc., Piscataway, N.J.). The oligonucleotide-containing carrier will be at the void volume.

EXAMPLE 9

Preparation of Carrier with Phosphoamide and Phosphodiester Linked Oligonucleotide To a ml. of aqueous solution containing 5 nanomoles each of amino in amino containing carrier (with or without protective chains) or hydroxyl in hydroxyl containing carrier (with or without protective chains) and 5' phosphate oligonucleotide, 10 mg. of EDAC will be added. The solutions will be left at room temperature overnight after adjusting the pH to 6. The oligonucleotide-containing carrier will isolated by chromatography using beads of dextran gel cross-linked with bisacrylamide having an exclusion volume of about 80,000 Daltons for dextran (SEPHACRYL S-100, Pharmacia, Inc., Piscataway, N.J.). The oligonucleotide-containing carrier will be at the void volume.

EXAMPLE 10

Bulk Synthesis (10 g) of Oligonucleotide-Core Carrier

In order to incorporate the complimentary DNA oligonucleotide into the carrier, a 4-100 base oligonucleotide will be prepared by Biosynth Inc. (Naperville, Ill.). This oligonucleotide will be modified by the manufacturer with an NHS activated carboxyl group appended to the 5' site via a phophonate ester and an 12 carbon alkyl chain. Coupling of modified oligonucleotide to the polylysine carrier utilizing similar chemistry described above (Example 1-4). An aqueous solution of 10 grams of pegylated polylysine (PL-PEG) in 200 ml of 200 mM HEPES buffer, pH 7.3 will be treated with an excess of the modified oligonucleotide to effect the saturation of the remaining amino groups of the polylysine backbone with the desired amide coupling. The polymeric material would be purified by ultrafiltration through a hollow fiber membrane with 100,000 molecular weight cutoff. Lyophilization of the resulting filtrate would afford the desired carrier.

EXAMPLE 11

This general procedure can be used to conjugate amino-modified oligonucleotides with active succinimidyl ester or isothiocyanate derivatives of various carriers, such as polyglutamate or poly aspartate and load molecules. At pH 7-9 the conjugation reaction occurs virtually exclusively at the free primary amine and does not involve the exocyclic amino groups of the nucleosides. Example: 1). For a 250 nmole scale synthesis, resuspend the amino-modified oligonucleotide (i.e. approximately 100 nmoles of primary reactive amine) in 0.7 mL of sterile distilled water. 2). Add 100 ul of 10× conjugation buffer (1.0 M NaHCO3)/Na2CO3, pH 9.0 or HEPES buffer at pH 7.3). 3). Freshly prepare a two reactive equivalent solution of succinimidyl ester activated carrier in 200 ul DMF and add to the solution to the reaction mixture. 4). Allow the mixture to stand at least 2 hours. 5). Remove unreacted oligonucleotide by gel filtration (such as Sephadex G-75) alternatively oligo-labeled carrier can be purified from unreacted oligo by ultrafiltration purification. 6). Depending on the reactivity of the NHS-ester used, coupling efficiency can range from 20-80%.

EXAMPLE 12

Synthesis of MPEG-Poly-1-Lysine-Oligonucleotide (40PLPEG522-Oligo)

40PLPEG522-oligo is an oligonucleotide-core carrier containing oligonucleotide groups attached to the epsilon amino group of the remaining lysine residues. Twenty mg of 40PLPEG522 from Example 3 will be dissolved to 2 ml with 0.2 M HEPES ([4-(2-hydroxyethyl)-1-piperazineethanesulfonic acid]) buffer pH 7.3. Fifty mg of oligonucleotide containing carboxyl group will be dissolved 100 ul of 10 mM MES ([2-(N-morpholino)ethanesulfonic acid]) buffer pH4.7 and 25 mg of NHSS (N-hydroxysuccinimide sulfate; Pierce, Rockfor, Ill.) will be added followed by 100 mg of EDC (1-ethyl-3-[3-dimethylaminopropyl]carbodiimide hydrochloride; Pierce, Rockfor, Ill.). This solution will be added drop-wise to the 2 ml solution of P40PLPEG522, and incubated at room temperature. The next day, aliquots will be taken and the amount of amino group remaining will be quantified using trinitrobenzenesulfonic acid (NBS) (Sparado et al. Anal Biochem 96:317, 1979). The protected on the amino group of the bases will be removed by ammonium hydroxide. The remaining soluble oligonucleotide and NHSS are removed by passing the solution through 20 ml Superdex 200 (Amersham Biosciences Corp, Westborough, Mass.) and will be eluted with water and the void volume containing PLPEG-III-oligo will be lyophilized

EXAMPLE 13

Synthesis of 20PLPEG5-55 and Quality Assurance

Figure 11:
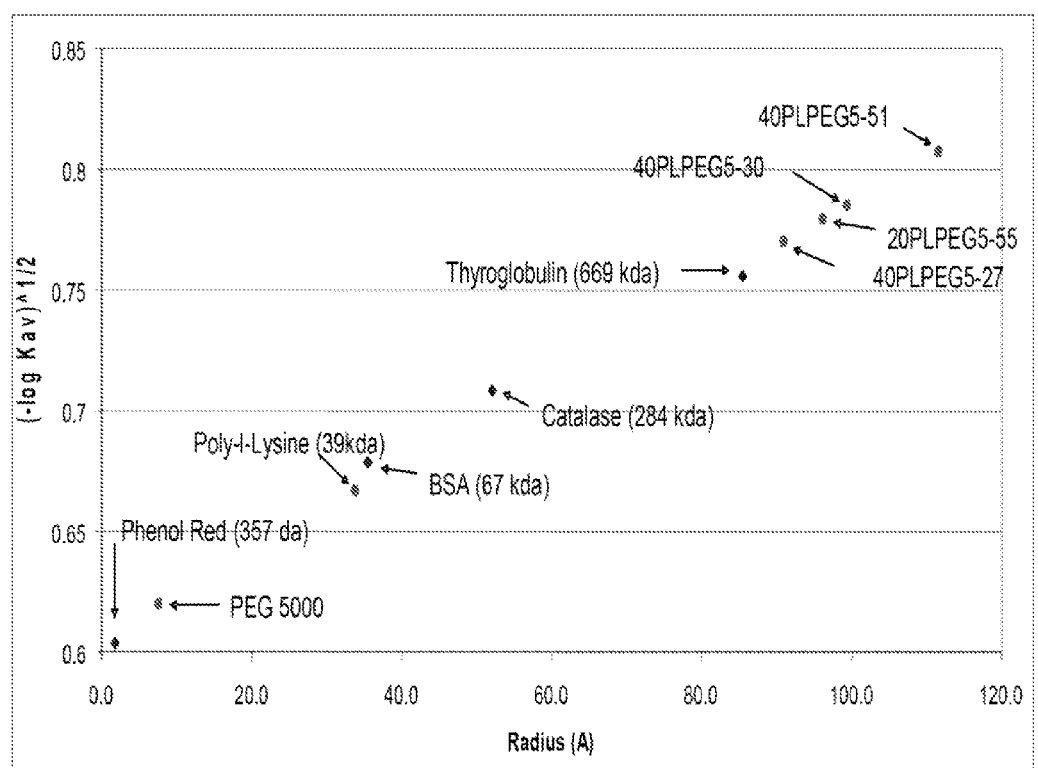
FIG. 11. These are the Stokes radii of various carriers along with proteins of known stokes radii. These were analyzed on the Ultrahydrogel Unear column (0.78 cm diameter×30 cm length) using PBS with 15% Acetonitrile at a flow rate of 0.6 ml/min as mobile phase. The 20PL-PEG5-55 (20 kDa polylysine where 55% of the amino groups were reacted with PEG succinate of 5 kDa molecular weight), 40PL-PEG5-30 (40 kDa polylysine where 30% of the amino groups were reacted with PEG succinate of 5 kDa molecular weight), 40PL-PEG5-51 (40 kDa polylysine where 51% of the amino groups were reacted with PEG succinate of 5 kDa molecular weight), and 40PL-PEG5-27 (40 kDa polylysine where 27% of the amino groups were reacted with PEG succinate of 5 kDa molecular weight) are larger than the glumerular filtration cut off that is above 4 nm (40 Angstrom) in diameter (or 20 Angstrom in radius). Proteins with known stokes radii were used as reference including Thyroglobulin (669 kDa; 85.5 Angstroms stokes radius), Catalase (248 kDa; 52.2 Angstrom stokes radius), and BSA (67 kDa; 35.5 Angstroms stokes radius), Catalase (248 kDa; 52.2 Angstrom stokes radius), and BSA (67 kDa; 35.5 Angstrom stokes radius).
Figure 12:
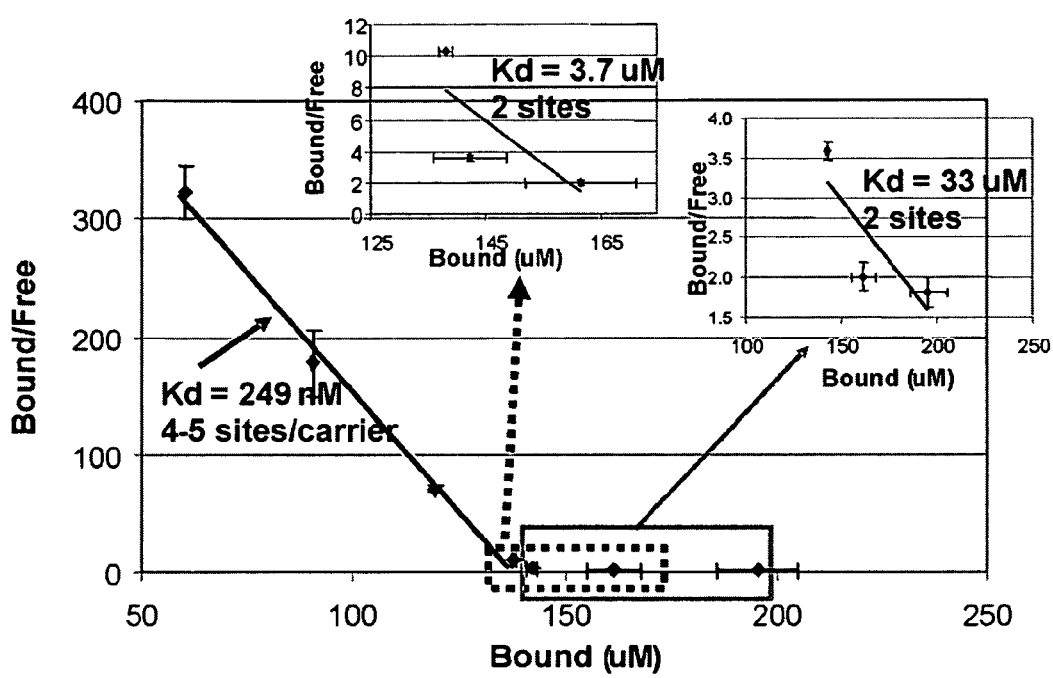

To determine the theoretical and actual relationship between the amount of amino-group/mg of PLPEG (polylysine-polyethyleneglycol copolymer) and % amino-group saturation of polylysine, an equation was developed to predict the saturation of polylysine based on the amino group measured by TNBS reaction expressed per mg of the final PLPEG product. This is useful only if the PEG used in the reaction is 95-100% purity from any carboxyl containing compounds. The equation is very useful as secondary confirmation of the composition of PLPEG. The theoretical prediction was calculated using the following equation: $X=[100\times(C-Y)]/5YC+C]$; where X is the % saturation; Y is the mmol $NH_2$ per gram of PLPEG as determined by TNBS; C is the mmol of $NH_2$ per gram of PL (polylysine) as determined by TNBS. The 5 in the term 5YC in the equation represent the size of PEG used which in this case is 5 kDa, thus 5YC. If 10 kDa PEG is used, this will be 10YC. This is useful because once PLPEG product is formed, the percent saturation of the amino group of polylysine can be determined by a single TNBS assay of the final product to determine Y from which X can be calculated. This equation was tested against experimental data by synthesizing PLPEG using high purity MPEG-succinate as follows. 1 gm of 20PL (thistime 1 gm has 1.7 mmol NH2) was dissolved in 100 ml of 200 mM HEPES. On a separate container 5 g of MPEGSuccinate in 25 ml of 10 mM MES pH=4.7 was activated by adding 250 mg of NHSS, followed by 500 mg EDC dissolved in water. Activation is allowed to proceed for 18-20 minutes. The activated MPEGSuccinate was added to 20PL solution and allowed to react for 4 hrs. After 4 hrs, additional 5 g of MPEGSuccinate was activated and added as above and allowed to incubate overnight with stirring. The next day, amino group was measured and found to be 0.77 mmol indicating 55% saturation of amino group. A small portion of the sample was analyzed by size exclusion chromatography before (FIG. 11 panel A) and after washing by ultrafiltration through 100 kDa molecular cut-off filter (FIG. 11 panel C) and the diameter of the co-polymer was determined (FIG. 12). The washed sample was lyophilized (8 grams; designated 20PLPEG555) and the amount of amino-group per mg of dried final product was determined by TNBS assay (Sparado et al. Anal Biochem 96:317, 1979). Using the equation above the percent PEG saturation was confirmed to be 55% (FIG. 9). Several more syntheses were performed and the theoretical was compared with experimental (FIG. 9).

EXAMPLE 14

Determination of the Dissociation Constant (Kd) Between Oligonucleotide-Core Carrier and Load Molecule Multiple tubes containing 5 mg of carrier/tube will be mixed with 0.50, 0.40, 0.30, 0.25, 0.20, 0.15, 0.1 mg of oligonucleotide-containing load molecule. The amount of oligonucleotide-containing load molecule mixed with carrier in each vial will correspond to 2, 3, 4, 5, 6, 8, and 10% of the carrier weight. Blank tubes containing no carrier will be also prepared and similarly treated in subsequent procedures. The samples will all be in 500 ul of PBS (pH 7.3) and the bound load molecule will be filtered out using 100 MWCO regenerated cellulose filter (Millipore, Bedford, Mass.) by centrifugation at 10,000×g for 12 minutes. The filtrates containing free load molecule will be quantified by reverse phase HPLC. The materials left in the filter will be washed 3 times with 100 ul of high salt buffer (4M guanidine) by centrifugation as above and the liberated load molecule (bound portion) from each sample will be quantified by reverse phase HPLC. The Bound/Free values will be calculated and plotted against bound values. The slopes of the regression line of the linear regions will be −1/Kd from which Kds will be calculated.

Although the foregoing invention has been described in some detail by way of illustration and example for the purposes of clarity of understanding, one skilled in the art will easily ascertain that certain changes and modifications may be practiced without departing from the spirit and scope of the appended claims.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An oligonucleotide-core carrier composition comprising:
   (i) a carrier;
   (ii) at least one of a first single stranded oligonucleotide group covalently linked to the carrier, wherein the oligonucleotide group is less than 100 bases;
   (iii) a plurality of polymeric protective side chains, wherein each protective side chain is covalently linked and pendant to the carrier and/or to the first oligonucleotide group wherein each protective side chain has a molecular weight between about 400 and 20,000 Daltons independent of the carrier weight and the first oligonucleotide group weight; and
   (iv) a load molecule, wherein the load molecule comprises a peptide/protein covalently bonded to a second single stranded oligonucleotide group with an essentially complementary sequence to the first single stranded oligonucleotide group and dissociably linked by nucleotide hydrogen bonding base pairing to the first oligonucleotide group;
   wherein said carrier is a polymer selected from the group consisting of a polyamino acid, a polyethyleneimine, a polyallyamine, a chitosan, a polysaccharide, an oligosaccharide, a natural saccharide, an aminated and carboxylated polysaccharide, an aminated and carboxylated oligosaccharide, a sulfonated polysaccharide, a sulfonated oligosaccharide, an aminocarboxylated polysaccharide, an aminocarboxylated oligosaccharide, a carboxymethylated polysaccharide, a carboxymethylated oligosaccharide, a polyamidoamine, a polyacrylic acid, a polyvinyl alcohol, and a polythiol; and
   further wherein the plurality of polymeric protective side chains comprises polyethylene glycol, polypropylene glycol, or a co-polymer of polyethylene glycol and polypropylene glycol.

2. The oligonucleotide-core carrier composition of claim 1, wherein the first oligonucleotide group comprises various nucleotide monomers selected from the group of monomers consisting of deoxyribonucleotide, 2'-deoxyribonucleotide, ribonucleotide, 2'-O-methylribonucleotide, locked ribonucleotide, N-(2-ethylamino)glycine nucleotide and morpholino nucleotide, wherein each nucleotide is covalently linked to another by a 3'-5' or 2'-5' linkage, wherein the linkage comprises a phosphodiester, phosphorothio, phosphotriester, phosphorodiamidate or a peptide, and wherein the base component of the nucleotide is any one of adenine, thymine, guanine, cytosine, uracil, inosine, thioinosine, thiouridine, xanthosine, pseudouridine, or orotidine.

3. The oligonucleotide-core carrier composition of claim 1, wherein the load molecule is a therapeutic agent.

4. The oligonucleotide-core carrier composition of claim 3, wherein the therapeutic agent is oligonucleotide-bonded peptide/proteins; wherein the peptide/protein is selected from a group consisting of a peptide aptamer, a glucagon-like peptide, a glucagon-like-peptide derivative, exenatide, leptin, a leptin fragment, alpha melanocyte stimulating hormone, adeponectin, Gastric inhibitory polypeptide(GIP), an Epidermal Growth Factor (EGF) receptor ligand, EGF, Transforming Growth Factor alpha (TGF-alpha), Betacellulin, a Gastrin/Cholecystokinin receptor ligand, Gastrin, Cholecystokinin, lysostaphin, interferon, interferon gamma, interferon beta, interferon alpha, interleukin-1, interleukin-2, interleukin-4, interleukin-6, interleukin-8, interleukin-10, interleukin-12, tumor necrosis factor, tumor necrosis factor alpha, tumor necrosis factor beta, insulin, insulin-like growth factor, growth hormone, nerve growth factor, brain-derived neurotrophic factor, enzymes, endostatin, angiostatin, trombospondin, urokinase, streptokinase, blood clotting factor VII, blood clotting factor VIII, granulucyte-macrophage colony-stimulating factor (GMCSF), granulucyte colony-stimulating factor (G-CSF), thrombopoetin, calcitonin, parathyroid hormone (PTH) and its fragments, erythropoietin, atrial natriuretic factor, monoclonal antibodies, monoclonal antibody fragments, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, and filgrastin.

5. The oligonucleotide-core carrier composition of claim 3, wherein the therapeutic agent is oligonucleotide-bonded peptide/proteins; wherein the peptide/protein is selected from a group consisting of Glucagon-like-peptide, Leptin, a Leptin fragment, Peptide YY, an Epidermal Growth Factor (EGF) receptor ligand, EGF, Transforming Growth Factor alpha (TGF-alpha), Betacellulin, a Gastrin/Cholecystokinin receptor ligand, Gastrin, Cholecystokinin, interferon, factor VIII, terlipressin, Gastric inhibitory polypeptide(GIP), and vasoactive intestinal peptide (VIP).

6. The oligonucleotide-core carrier composition of claim 1, further comprising a targeting molecule covalently linked to at least one protective side chain.

7. The oligonucleotide-core carrier composition of claim 6, wherein the targeting molecule is selected from the group consisting of antibodies, fragments of antibodies, chimeric antibodies, lectins, receptor ligands, proteins, enzymes, peptides, saccharides, quasi substrates of enzymes, cell-surface-binding compounds, and extracellular-matrix-binding compounds.

8. The composition of claim 2, wherein the first oligonucleotide group comprises a deoxyribonucleotide monomer.

9. The composition of claim 1, wherein the carrier is 2,000 to 60,000 Daltons.

10. The composition of claim 1, wherein the first single stranded oligonucleotide group is guanine rich and the second single stranded oligonucleotide group is cytosine rich.

11. The composition of claim 1, wherein the first single stranded oligonucleotide group is cytosine rich and the second single stranded oligonucleotide group is guanine rich.

12. The composition of claim 1, wherein the first single stranded oligonucleotide group is adenine rich and the second single stranded oligonucleotide group is thymine rich.

13. The composition of claim 1, wherein the first single stranded oligonucleotide group is thymine rich and the second single stranded oligonucleotide group is adenine rich.

14. A method of increasing the blood circulation half-life of peripherally administered peptide/protein covalently bonded to single stranded oligonucleotide by injecting into a patient a formulation comprising the oligonucleotide-core carrier composition of claim 1.

15. The method of claim 14, wherein the peptide/protein covalently bonded to single stranded oligonucleotide is selected from a group consisting of a peptide, an enzyme, an antibody, and a cytokine.

16. The method of claim 15, wherein the cytokine is an interferon or a tumor necrosis factor.

17. The method of claim 15, wherein the antibody is selected from the group consisting of a monoclonal antibody, an antibody fragment, and a chimeric antibody.

18. The method of claim 14, wherein the peptide/protein covalently bonded to single stranded oligonucleotide is selected from a group consisting of a peptide aptamer, a glucagon-like peptide (GLP), a glucagon-like-peptide derivative, exenatide, leptin, a leptin fragment, alpha melanocyte stimulating hormone, adeponectin, Gastric inhibitory polypeptide(GIP), an Epidermal Growth Factor (EGF) receptor ligand, EGF, Transforming Growth Factor alpha (TGF-alpha), Betacellulin, a Gastrin/Cholecystokinin receptor ligand, Gastrin, Cholecystokinin, lysostaphin, terlipressin, interferon, interferon gamma, interferon beta, interferon alpha, interleukin-1, interleukin-2, interleukin-4, interleukin-6, interleukin-8, interleukin-10, interleukin-12, tumor necrosis factor, tumor necrosis factor alpha, tumor necrosis factor beta, insulin, insulin-like growth factor, growth hormone, nerve growth factor, brain-derived neurotrophic factor, enzymes, endostatin, angiostatin, trombospondin, urokinase, streptokinase, blood clotting factor VII, blood clotting factor VIII, granulucyte-macrophage colony-stimulating factor (GMCSF), granulucyte colony-stimulating factor (G-CSF), Peptide YY, thrombopoetin, calcitonin, parathyroid hormone (PTH) and its fragments, erythropoietin, atrial natriuretic factor, monoclonal antibodies, monoclonal antibody fragments, chimeric antibodies, somatostatin, protease inhibitors, adrenocorticotropin, gonadotropin releasing hormone, oxytocin, leutinizing-hormone releasing-hormone, follicle stimulating hormone, glucocerebrosidase, thrombopoietin, and filgrastin.

* * * * *